(12) United States Patent
Colonna et al.

(10) Patent No.: US 11,066,456 B2
(45) Date of Patent: Jul. 20, 2021

(54) COMPOSITIONS COMPRISING TREM2 AND METHODS OF USE THEREOF

(71) Applicant: Washington University, St. Louis, MO (US)

(72) Inventors: Marco Colonna, St. Louis, MO (US); Yarning Wang, St. Louis, MO (US); Marina Celia, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 16/079,816

(22) PCT Filed: Feb. 24, 2017

(86) PCT No.: PCT/US2017/019480
§ 371 (c)(1),
(2) Date: Aug. 24, 2018

(87) PCT Pub. No.: WO2017/147509
PCT Pub. Date: Aug. 31, 2017

(65) Prior Publication Data
US 2019/0048057 A1    Feb. 14, 2019

Related U.S. Application Data

(60) Provisional application No. 62/299,849, filed on Feb. 25, 2016.

(51) Int. Cl.
| | |
|---|---|
| *A61K 38/17* | (2006.01) |
| *A61P 25/28* | (2006.01) |
| *C07K 14/705* | (2006.01) |
| *C07K 16/28* | (2006.01) |
| *C12Q 1/68* | (2018.01) |
| *C07K 16/46* | (2006.01) |
| *C12N 15/62* | (2006.01) |

(52) U.S. Cl.
CPC .......... *C07K 14/705* (2013.01); *A61K 38/177* (2013.01); *A61P 25/28* (2018.01); *C07K 16/2803* (2013.01); *C07K 16/46* (2013.01); *C12N 15/62* (2013.01); *C12Q 1/68* (2013.01); *C07K 2317/76* (2013.01); *C07K 2319/01* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,173,414 A | 12/1992 | Lebkowski et al. |
| 5,223,409 A | 6/1993 | Ladner et al. |
| 5,403,484 A | 4/1995 | Ladner et al. |
| 5,571,698 A | 11/1996 | Ladner et al. |
| 5,641,870 A | 6/1997 | Rinderknecht et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,878,687 B1 * | 4/2005 | Ruben .................... C07K 14/47 435/252.3 |
| 7,198,951 B2 | 4/2007 | Gao et al. |
| 2010/0310560 A1 | 12/2010 | Colonna et al. |
| 2013/0039888 A1 | 2/2013 | McCarty et al. |

FOREIGN PATENT DOCUMENTS

| | | |
|---|---|---|
| EP | 0404097 B1 | 9/1996 |
| WO | 1993011161 A1 | 6/1993 |
| WO | 1995013365 A1 | 5/1995 |
| WO | 1995013392 A1 | 5/1995 |
| WO | 1996017947 A1 | 6/1996 |
| WO | 1997006243 A1 | 2/1997 |
| WO | 1997008298 A1 | 3/1997 |
| WO | 1997009441 A2 | 3/1997 |
| WO | 1997021825 A1 | 6/1997 |
| WO | 1999011764 A2 | 3/1999 |
| WO | 2001083692 A2 | 11/2001 |
| WO | 2017147509 A1 | 8/2017 |

OTHER PUBLICATIONS

Bezbradica et al., (Nat Immunol. Apr. 2014;15(4):333-342 (Year: 2014).*
Van Vugtetal. Blood. Jul. 15, 1999;94(2):808-817 (Year: 1999).*
Baileyetai., J Biol Chem. Oct. 23, 2015;290(43):26033-26042 (Year: 2015).*
Ahyayauch, H. et al., "Binding of beta-Amyloid (1-42) Peptide to Negatively Charged Phospholipid Membranes in the Liquid-Ordered State: Modeling and Experimental Studies," Biophys. J., Aug. 2012, pp. 453-463, vol. 103.
Altschul, S. et al., "Basic Local Alignment Search Tool," J. Mo. Biol., 1990, pp. 403-410, vol. 215, Academic Press Limited.
Altschul, S. et al., "Gapped BLAST and PSI-BLAST: a new generation of protein database search programs," Nucl. Acid Res., 1997, pp. 3389-3402, vol. 25, No. 17, Oxford University Press.
Bouchon, A. et al., "A DAP12-mediated Pathway Regulates Expression of CC Chemokine Receptor 7 and Maturation of Human Dendritic Cells," J. Exp. Med., Oct. 15, 2001, pp. 1111-1122, vol. 194, No. 8, The Rockefeller University Press.

(Continued)

*Primary Examiner* — Daniel C Gamett
(74) *Attorney, Agent, or Firm* — Polsinelli PC

(57) ABSTRACT

The present invention provides TREM2 constructs. TREM2 constructs of the invention are polynucleotide sequences encoding a polypeptide, wherein the polypeptide comprises at least one TREM2 or fragment thereof and a targeting moiety and optionally comprising a signal peptide and/or a purification moiety. The present invention also provides isolated polypeptides encoded by TREM2 constructs, vectors comprising TREM2 constructs, isolated cells comprising said vectors, and methods of use thereof.

7 Claims, 44 Drawing Sheets
(39 of 44 Drawing Sheet(s) Filed in Color)
Specification includes a Sequence Listing.

(56) References Cited

OTHER PUBLICATIONS

Butovsky, O. et al., "Identification of a unique TGF-beta-dependent molecular and functional signature in microglia," Nat. Neurosci., Jan. 2014, pp. 131-143, vol. 17, No. 1, with Online Methods and Corrigendum, 5 pgs., Nature America, Inc.

Cannon, J. et al., "Specific lipid recognition is a general feature of CD300 and TREM molecules," Immunogenetics, Jan. 2012, pp. 39-47, vol. 64, No. 1.

Carell, T. et al., "A Novel Procedure for the Synthesis of Libraries Containing Small Organic Molecules," Angew.Chem. Int. Ed. Engl., 1994, pp. 2059-2061, vol. 33, No. 20, VCH Verlagsgesellschaft mbH, Weinheim, Germany.

Carter, B., "Adeno-associated virus vectors," Curr. Opin. Biotechnol., Oct. 1992, pp. 533-539, vol. 3, No. 5.

Chitu, V. et al., "Colony-stimulating factor-1 in immunity and inflammation," Curr. Opin. Immunol., Feb. 2006, pp. 39-48, vol. 18, No. 1.

Cho, C. et al., "An Unnatural Biopolymer," Sci., Sep. 3, 1993, pp. 1303-1305, vol. 261, No. 5126.

Clark, K. et al., "A stable cell line carrying adenovirus-inducible rep and cap genes allows for infectivity titration of adeno-associated virus vectors," Gene Ther., Dec. 1996, pp. 1124-1132, vol. 3, No. 12.

Crotti, A. et al., "The choreography of neuroinflammation in Huntington's disease," HHS Public Access Author Manuscript, Jun. 1, 2016, pp. 1-20, published in final edited form as: Trends Immunol., Jun. 2015, pp. 364-373, vol. 36, No. 6.

Cull, M. et al., "Screening for receptor ligands using large libraries of peptides linked to the C terminus of the lac repressor," PNAS, Mar. 1992, pp. 1865-1869, vol. 89.

Cwirla, S. et al., "Peptides on phage: a vast library of peptides for identifying ligands," PNAS, Aug. 1990, pp. 6378-6382, vol. 87.

D'Andrea, M. et al., "The microglial phagocytic role with specific plaque types in the Alzheimer disease brain," Neurobiol. Aging, 2004, pp. 675-683, vol. 25, Elsevier Inc.

Daws, M. et al., "Cloning and characterization of a novel mouse myeloid DAP12-associated receptor family," Eur. J. Immunol., 2001, pp. 783-791, vol. 31, Wiley-VCH Verlag GmbH, Weinheim.

Daws, M. et al., "Pattern Recognition by TREM-2: Binding of Anionic Ligands," J. Immunol., 2003, pp. 594-599, vol. 171.

Del Mar Martinez-Senac, M. et al., "Structure of the Alzheimer beta-amyloid peptide (25-35) and its interaction with negatively charged phospholipid vesicles," Eur. J. Biochem., 1999, pp. 744-753, vol. 265.

Devlin, J. et al., "Random Peptide Libraries: A Source of Specific Protein Binding Molecules," Sci., Jul. 27, 1990, pp. 404-406, vol. 249, No. 4967.

Dewitt, S. et al., "'Diversomers': An approach to nonpeptide, nonoligomeric chemical diversity," PNAS, Aug. 1993, pp. 6909-6913, vol. 90.

Dickson, D., "Microglia in Alzheimer's Disease and Transgenic Models. How Close the Fit?," Am. J. Pathol., Jun. 1999, pp. 1627-1631, vol. 154, No. 6.

Duque, S. et al., "Intravenous Administration of Self-complementary AAV9 Enables Transgene Delivery to Adult Motor Neurons," Mol. Ther., Jul. 2009, pp. 1187-1196, vol. 17, No. 7.

Eckert, G. et al., "Membrane Disordering Effects of beta-Amyloid Peptides," In: Harris J.R., Fahrenholz F. (eds) Alzheimer's Disease. Subcellular Biochemistry, 2005, pp. 319-337, Ch. 16, vol. 38, Springer.

Eimer, W. et al., "Neuron loss in the 5XFAD mouse model of Alzheimer's disease correlates with intraneuronal Abeta42 accumulation and Caspase-3 activation," Mol. Neurodegener., 2013, pp. 1-12, vol. 8, No. 2.

El Khoury, J. et al., "Ccr2 deficiency impairs microglial accumulation and accelerates progression of Alzheimer-like disease," Nat. Med., Apr. 2007, p. 432-438, vol. 13, No. 4.

Erb, E. et al., "Recursive deconvolution of combinatorial chemical libraries," PNAS, Nov. 1994, pp. 11422-11426, vol. 91.

Felici, F., "Selection of Antibody Ligands from a Large Library of Oligopeptides Expressed on a Multivalent Exposition Vector," J. Mol. Biol., 1991, pp. 301-310, vol. 222.

Fodor, S. et al., "Multiplexed biochemical assays with biological chips," Nature, Aug. 5, 1993, pp. 555-556, vol. 364, Nature Publishing Group.

Ford, J. et al., "TREM and TREM-like Receptors in Inflammation and Disease," NIH Public Access, Author Manuscript, Feb. 1, 2010, pp. 1-17, published in final edited form as: Curr. Opin. Immunol., Feb. 2009, pp. 38-46, vol. 21, No. 1.

Foust, K. et al., "Intravascular AAV9 preferentially targets neonatal neurons and adult astrocytes," Nat. Biotechnol., Jan. 2009, pp. 59-65, vol. 27, No. 1.

Frautschy, S. et al., "Microglial Response to Amyloid Plaques in APPsw Transgenic Mice," Am. J. PathoL, 1998, pp. 307-317, vol. 152.

Fric, J. et al., "NFAT control of innate immunity," Blood, Aug. 16, 2012, pp. 1380-1389, vol. 120, No. 7.

Gallop, M. et al., "Applications of Combinatorial Technologies to Drug Discovery. 1. Background and Peptide Combinatorial Libraries," J. Med. Chem., Apr. 29, 1994, pp. 1233-1251, vol. 37, No. 9.

Gao, G. et al., "Clades of Adeno-Associated Viruses Are Widely Disseminated in Human Tissues," J. Virol., Jun. 2004, pp. 6381-6388, vol. 78, No. 12.

GenBank Accession No. BAB78736.1 dated Dec. 8, 2001; 1 pg.

Grathwohl, S. et al., "Formation and maintenance of Alzheimer's disease beta-amyloid plaques in the absence of microglia;" Advance Online Publication, pp. 1-13, Nat. Neurosci., 2009, pp. 1361-1363, vol. 12.

Guerreiro, R. et al., "A novel compound heterozygous mutation in TREM2 found in a Turkish frontotemporal dementia-like family," Neurobiol. Aging, 2013, pp. 2890.e1-2890.e5, vol. 34.

Guerreiro, R. et al., "TREM2 Variants in Alzheimer's Disease," N. Engl. J. Med., 2013, pp. 117-127, vol. 368.

Guerreiro, R. et al., "Using Exome Sequencing to Reveal Mutations in TREM2 Presenting as a Frontotemporal Dementia-like Syndrome Without Bone Involvement," JAMA Neurol., 2013, pp. 78-84, vol. 70, No. 1.

Hamerman, J. et al., "Cutting Edge: Inhibition of TLR and FcR Responses in Macrophages by Triggering Receptor Expressed on Myeloid Cells (TREM)-2 and DAP12," J. Immunol., 2006, pp. 2051-2055, vol. 177.

Heng, T. et al., "The Immunological Genome Project: networks of gene expression in immune cells," Nat. Immunol., Oct. 2008, pp. 1091-1094, vol. 9, No. 10.

Hermonat, P. et al., "Use of adeno-associated virus as a mammalian DNA cloning vector: Transduction of neomycin resistance into mammalian tissue culture cells," PNAS, Oct. 1984, pp. 6466-6470, vol. 81.

Hickman, S. et al., "Microglial Dysfunction and Defective beta-Amyloid Clearance Pathways in Aging Alzheimer's Disease Mice," J. Neurosci., Aug. 13, 2008, pp. 8354-8360, vol. 28, No. 33.

Holliger, P. et al., "'Diabodies': Small bivalent and bispecific antibody fragments," PNAS, Jul. 1993, pp. 6444-6448, vol. 90.

Houghten, R. et al., "The Use of Synthetic Peptide Combinatorial Libraries for the Identification of Bioactive Peptides," Biotechniques, Sep. 1992, pp. 412-421, vol. 13. No. 3.

Hsieh, C. et al., "A role for TREM2 ligands in the phagocytosis of apoptotic neuronal cells by microglia," J. Neurochem., 2009, pp. 1144-1156, vol. 109.

Huang, W-C. et al., "TGF-beta1 blockade of microglial chemotaxis toward Abeta aggregates involves SMAD signaling and down-regulation of CCLS," J. Neuroinflammation, 2010, pp. 1-11, vol. 7, No. 28.

Huang, Y. et al., "Alzheimer Mechanisms and Therapeutic Strategies," Cell,Mar. 16, 2012, pp. 1204-1222, vol. 148.

Hudson, P. et al., "Engineered antibodies," Nat. Med., Jan. 2003, pp. 129-134, vol. 9, No. 1.

International Search Report and Written Opinion dated May 25, 2017 from related Patent Application No. PCT/US2017/019480; 14 pgs.

(56) References Cited

OTHER PUBLICATIONS

Paloneva, J. et al., "Mutations in Two Genes Encoding Different Subunits of a Receptor Signaling Complex Result in an Identical Disease Phenotype," Am. J. Hum. Genet., 2002, pp. 656-662, vol. 71.
Paul, R. et al., "Increased Viral Titer Through Concentration of Viral Harvests from Retroviral Packaging Lines," Hum. Gene Ther., Oct. 1993, pp. 609-615, vol. 4, No. 5, Mary Ann Liebert, Inc. Publishers.
Peng, Q. et al., "TREM2- and DAP12-Dependent Activation of PI3K Requires DAP10 and is Inhibited by SHIP1," Sci. Signal., May 18, 2010, pp. 1-15, vol. 3, No. 122, ra38.
Perlmutter, L. et al., "Morphologic association between microglia and senile plaque amyloid in Alzheimer's disease," Neurosci. Lett., Oct. 30, 1990, pp. 32-36, vol. 119, No. 1, Elsevier Scientific Publishers Ireland Ltd.
Perrin, P. et al., "An experimental rabies vaccine produced with a new BHK-21 suspension cell culture process: use of serum-free medium and perfusion-reactor system," Vaccine, Sep. 1995, pp. 1244-1250, vol. 13, No. 13, Elsevier Science Ltd., Great Britain.
Picco, L. et al., "Blockade of TREM-2 exacerbates experimental autoimmune encephalomyelitis," Eur. J. ImmunoL, May 2007, pp. 1290-1301, vol. 37, No. 5.
Quan, D. et al., "TREM-2 Binds to Lipooligosaccharides of Neisseria gonorrhoeae and is Expressed on Reproductive Tract Epithelial Cells," NIH Public Access Author Manuscript, Jan. 6, 2009, pp. 1-23, published in final edited form as: Mucosal ImmunoL, May 2008, pp. 229-238, vol. 1, No. 3.
Ransohoff, R. et al., "The myeloid cells of the central nervous system parenchyma," Nature, Nov. 11, 2010, pp. 253-262, vol. 468, Macmillan Publishers Limited.
Rayaprolu, S. et al., "TREM2 in neurodegeneration: evidence for association of the p.R47H variant with frontotemporal dementia and Parkinson's disease," Mol. Neurodegener. Jun. 21, 2013, pp. 1-5, vol. 8, No. 19.
Reich, M. et al., "GenePattern 2.0," Nat. Genet., May 2006, pp. 500-501, vol. 38, No. 5, Nature Publishing Group.
Ruffing, M. et al., "Mutations in the carboxy terminus of adeno-associated virus 2 capsid proteins affect viral infectivity: lack of an RGD integrin-binding motif," J. Gen. Virol., 1994, pp. 3385-3392, vol. 75.
Samulski, R. et al., "Cloning of adeno-associated virus into pBR322: Rescue of intact virus from the recombinant plasmid in human cells," PNAS, Mar. 1982, pp. 2077-2081, vol. 79.
Samulski, R. et al., "Helper-Free Stocks of Recombinant Adeno-Associated Viruses: Normal Integration Does Not Require Viral Gene Expression," J. Virol., Sep. 1989, pp. 3822-3828, vol. 63, No. 9.
Schmid, C. et al., "Heterogeneous expression of the triggering receptor expressed on myeloid cells-2 on adult murine microglia," J. Neurochem., 2002, pp. 1309-1320, vol. 83.
Scott, J. et al., "Searching for Peptide Ligands with an Epitope Library," Sci., Jul. 27, 1990, pp. 386-390, vol. 249, No. 4967.
Senapathy, P. et al., "Molecular Cloning of Adeno-associated Virus Variant Genomes and Generation of Infectious Virus by Recombinant in Mammalian Cells," J. Biol. Chem., Apr. 10, 1984, pp. 4661-4666, vol. 259, No. 7.
Sessa, G. et al., "Distribution and signaling of TREM2/DAP12, the receptor system mutated in human polycystic lipomembraneous osteodysplasia with sclerosing leukoencephalopathy dementia," Eur. J. Neurosci., Nov. 2004, pp. 2617-2628, vol. 20, No. 10.
Simard, A. et al., "Bone Marrow-Derived Microglia Play a Critical Role in Restricting Senile Plaque Formation in Alzheimer's Disease," Neuron, Feb. 16, 2006, pp. 489-502, vol. 49.
Singaraja, R., "TREM2: a new risk factor for Alzheimer's disease," Clin. Genet., Jun. 2013, pp. 525-526, vol. 83, No. 6, Blackwell Publishing Ltd., Singapore.
Srivastava, A. et al., "Nucleotide Sequence and Organization of the Adeno-Associated Virus 2 Genome," J. Virol., Feb. 1983, pp. 555-564, vol. 45, No. 2.
Stalder, M. et al., "Association of Microglia with Amyloid Plaques in Brains of APP23 Transgenic Mice," Am. J. Pathol., Jun. 1999, pp. 1673-1684. vol. 154, No. 6.
Stalder, A. et al., "Invasion of Hematopoietic Cells into the Brain of Amyloid Precursor Protein Transgenic Mice," J. Neurosci., Nov. 30, 2005, pp. 11125-11132, vol. 25, No. 48.
Stanley,E. et al., "CSF-1 Receptor Signaling in Myeloid Cells," Cold Spring Harb. Perspect. Biol., 2014, pp. 1-21, 6: a021857.
Strausberg, R. et al., "Generation and initial analysis of more than 15,000 full-length human and mouse cDNA sequences," PNAS, Dec. 24, 2002, pp. 16899-16903, vol. 99, No. 26, with GenBank AAH32362.1 supplement, Oct. 7, 2003, 2 pgs.
Streit, W. et al., "Dystrophic Microglia in the Aging Human Brain," GLIA, 2004, pp. 208-212, vol. 45, Wiley-Liss, Inc.
Streit, W. et al., "Life and Death of Microglia," J. Neuroimmune Pharmacol., Dec. 2009, pp. 371-379, vol. 4, No. 4.
Styren, S. et al., "X-34, A Fluorescent Derivative of Congo Red: A Novel Histochemical Stain for Alzheimer's Disease Pathology," J. Histochem. Cytochem., 2000, pp. 1223-1232, vol. 48, No. 9.
Takahashi, K. et al., "Clearance of apoptotic neurons without inflammation by microglial triggering receptor expressed on myeloid cells-2," J. Exp. Med., Feb. 21, 2005, pp. 647-657, vol. 201, No. 4, The Rockefeller University Press.
Takahashi, K. et al., "TREM2-Transduced Myeloid Precursors Mediate Nervous Tissue Debris Clearance and Facilitate Recovery in an Animal Model of Multiple Sclerosis," PLoS Med., Apr. 2007, pp. 0675-0689, vol. 4. No. 4, e124.
Tanzi, R., "A Brief History of Alzheimer's Disease Gene Discovery," J. Alzheimer's Dis., 2013, pp. pp. S5-S13, vol. 33, Suppl. 1, IOS Press.
Thrash, J. et al., "Developmental Regulation of TREM2 and DAP12 Expression in the Murine Cns: Implications for Nasu-Hakola Disease," Neurochem. Res. 2009, 38-45, vol. 34, Springer.
Tratschin, J-D. et al., "A Human Parvovirus, Adeno-Associated Virus, as a Eucaryotic Vector: Transient Expression and Encapsidation of the Procaryotic Gene for Chloramphenicol Acetyltransferase," Mol. Cell. Biol., Oct. 1984, pp. 2072-2081, vol. 4, No. 10.
Tratschin, J-D. et al., "Adeno-Associated Virus Vector for High-Frequency Integration, Expression, and Rescue of Genes in Mammalian Cells," Mol. Cell. Biol., Nov. 1985, pp. 3251-3260, vol. 5, No. 11.
Turnbull, I. et al., "Cutting Edge: TREM-2 Attenuates Macrophage Activation," J. Immunol., 2006, pp. 3520-3524, vol. 177.
Ulrich, J. et al., "Altered microglial response to Abeta plaques in APPPSl-21 mice heterozygous for TREM2," Mol. Neurodegener, 2014, pp. 1-9, vol. 9, No. 20.
Wang, Z. et al., "Adeno-associated virus serotype 8 efficiently delivers genes to muscle and heart," Nat. Biotechnol., Mar. 2005, pp. 321-328, vol. 23, No. 3.
Wang, Y. et al., "TREM2 lipid sensing sustains microglia response in an Alzheimer's disease model," Manuscript, undated. in an Alzheimer's disease model, Cell, Mar. 2015, pp. 1061-1071, vol. 160, Elsevier Inc.
Wilson, I. et al., "The Structure of an Antigenic Determinant in a Protein," Cell, Jul. 1984, pp. 767-778, vol. 37, No. 3.
Worgall, S. et al., "Treatment of Late Infantile Neuronal Ceroid Lipofuscinosis by CNS Administration of a Serotype 2 Adeno-Associated Virus Expressing CLN2 cDNA," Hum. Gene Ther., May 2008, pp. 1-12, vol. 19, with Supplementary Tables I-V, Mary Ann Liebert, Inc.
Zapata, G. et al., "Engineering linear F(ab')2 fragments for efficient production in *Escherichia coli* and enhanced antiproliferative activity," Protein Eng., Oct. 1995, pp. 1057-1062, vol. 8, No. 10.
Zincarelli, C. et al., "Analysis of AAV Serotypes 1-9 Mediated Gene Expression and Tropism in Mice After Systemic Injection," Mol. Ther., Jun. 2008, pp. 1073-1080, vol. 16, No. 6.
Zou, W. et al., "DAP12 Couples c-Fms Activation to the Osteoclast Cytoskeleton by Recruitment of Syk," Mol. Cell, Aug. 8, 2008, pp. 422-431, vol. 31.
Zuckermann, R. et al., "Discovery of Nanomolar Ligands for 7-Transmembrane G-Protein-Coupled Receptors from a Diverse N-(Substituted)glycine Peptoid Library," J. Med. Chem., 1994, pp. 2685, vol. 37.

(56) References Cited

OTHER PUBLICATIONS

Jiang, T. et al., "Upregulation of TREM2 Ameliorates Neuropathology and Rescues Spatial Cognitive Impairment in a Transgenic Mouse Model of Alzheimer's Disease," NeuropsychopharmacoL, 2014, pp. 2949-2962, vol. 39.
Jonsson, T. et al., "Variant of TREM2 Associated with the Risk of Alzheimer's Disease," N. Engl. J. Med., Jan. 10, 2013, pp. 107-116, vol. 368, No. 2.
Kaku, M. et al., "Amyloid beta protein deposition and neuron loss in osteopetrotic (op/op) mice," Brain Res. Protoc., Oct. 2003, pp. 104-108, vol. 12, No. 2.
Kaplitt, M. et al., "Safety and tolerability of gene therapy with an adeno-associated virus (AAV) borne Gad gene for Parkinson's disease: an open label, phase I trial," Lancet, Jun. 23, 2007, pp. 2097-2105, vol. 369.
Karlin, S. et al., "Methods for assessing the statistical significance of molecular sequence features by using general scoring schemes," PNAS, Mar. 1990, 2264-2268, vol. 87.
Kialainen, A. et al., "Dap12 and Trem2, molecules involved in innate immunity and neurodegeneration, are co-expressed in the CNS," Neurobiol. Dis., Mar. 2005, pp. 314-322, vol. 18, No. 2.
Kim, J. et al., "The Role of Apolipoprotein E in Alzheimer's Disease," Neuron, Aug. 13, 2009, pp. 287-303, vol. 63.
Keinberger, G. et al., "TREM2 mutations implicated in neurodegeneration impair cell surface transport and phagocytosis," Sci. Transl. Med., Jul. 2, 2014, pp. 1-12, vol. 6, Issue 243, 243ra286, with Supplementary Materials, pp. 1-12.
Lam, K. et al., "A new type of synthetic peptide library for identifying ligand-binding activity," Nature, Nov. 7, 1991, pp. 82-84, vol. 354, Nature Publishing Group.
Lam, K., "Application of combinatorial library methods in cancer research and drug discovery," Anti-Cancer Drug Design, 1997, pp. 145-167, vol. 12, No. 3, Oxford University Press.
Laughlin, C. et al., "Cloning of infectious adeno-associated virus genomes in bacterial plasmids," Gene, Jul. 1983, pp. 65-73, vol. 23, No. 1.
Lebkowski, J. et al., "Adeno-Associated Virus: A Vector System for Efficient Introduction and Integration of DNA into a Variety of Mammalian Cell Types," Mol. Cell. Biol., Oct. 1988, pp. 3988-3996, vol. 8, No. 10.
Malm, T. et al., "Bone-marrow-derived cells contribute to the recruitment of microglial cells in response to beta-amyloid deposition in APP/PS1 double transgenic Alzheimer mice," Neurobiol. Dis., Feb. 2005, pp. 134-142, vol. 18, No. 1.
Marks, W. et al., "Safety and tolerability of intraputaminal delivery of CERE-120 (adeno-associated virus serotype 2-neurturin) to patients with idiopathic Parkinson's disease: an open label, phase I trial," Lancet Neurol., May 2008, pp. 400-408, vol. 7.
McGeer, P. et al., "Reactive microglia in patients with senile dementia of the Alzheimer type are positive for the histocompatibility glycoprotein HLA-DR," Neurosci. Lett., 1987, pp. 195-200, vol. 79, Elsevier Scientific Publishers Ireland Ltd.
McLaughlin, S. et al., "Adeno-Associated Virus General Transduction Vectors: Analysis of Proviral Structures," J. Virol., Jun. 1988, pp. 1963-1973, vol. 62, No. 6.
McLaurin, J. et al., "Membrane Disruption by Alzheimer beta-Amyloid Peptides Mediated through Specific Binding to Either Phospholipids or Gangliosides," J. Biol. Chem., Oct. 25, 1996, pp. 26482-26489, vol. 271, No. 43.
Mildner, A. et al., "Distinct and Non-Redundant Roles of Microglia and Myeloid Subsets in Mouse Models of Alzheimer's Disease," J. Neurosci., Aug. 3, 2011, pp. 11159-11171, vol. 31, No. 31.
Mitrasinovic, O. et al., "Macrophage colony stimulating factor promotes phagocytosis by murine microglia," Neurosci. Lett., Jul. 3, 2003, pp. 185-188, vol. 344, No. 3.
Muzyczka, N. "Use of Adeno-Associated Virus as a General Transduction Vector for Mammalian Cells," Curr. Top. Microbiol. Immunol., 1992, pp. 97-129, vol. 158, Springer-Verlag Berlin-Heidelberg.

Nagarathinam, A. et al., "Membrane-Anchored Alpha-beta Accelerates Amyloid Formation and Exacerbates Amyloid-Associated Toxicity in Mice," J. Neurosci., Dec. 4, 2013, pp. 19284-19294, vol. 33, No. 49.
NCBI Reference Sequence NM_001037832.1 dated May 21, 2018; 2 pgs.
NCBI Reference Sequence NM_001079580.2 dated May 14, 2018; 2 pgs.
NCBI Reference Sequence NM_001106884.1 dated May 30, 2018; 3 pgs.
NCBI Reference Sequence NM_001271821.1 dated Dec. 2, 2018; 4 pgs.
NCBI Reference Sequence NM_001272078.1 dated Dec. 1, 2018; 4 pgs.
NCBI Reference Sequence NM_018965.3 dated Dec. 2, 2018; 4 pgs.
NCBI Reference Sequence NM_031254.3 dated Dec. 1, 2018; 4 pgs.
NCBI Reference Sequence XM_001174108.3 dated Oct. 8, 2014; 2 pgs.
NCBI Reference Sequence XM_001174118.3 dated Oct. 8, 2014; 2 pgs.
NCBI Reference Sequence XM_003511765.1, dated Apr. 30, 2014; 2 pgs.
NCBI Reference Sequence XM_003986128.3 dated Feb. 10, 2015; 2 pgs.
NCBI Reference Sequence XM_004043982.1 dated Dec. 3, 2012; 2 pgs.
NCBI Reference Sequence XM_004043983.1 dated Dec. 3, 2012; 2 pgs.
NCBI Reference Sequence XM_004043984.1 dated Dec. 3, 2012; 2 pgs.
NCBI Reference Sequence XM_005603890.1 dated Sep. 22, 2013; 2 pgs.
NCBI Reference Sequence XM_005603891.1 dated Sep. 22, 2013; 2 pgs.
NCBI Reference Sequence XM_005627313.1 dated Sep. 24, 2013; 2 pgs.
NCBI Reference Sequence XM_006244424.2 dated Aug. 7, 2014; 2 pgs.
NCBI Reference Sequence XM_006244425.2 dated Aug. 7, 2014; 2 pgs.
NCBI Reference Sequence XM_007639783.1 dated Apr. 30, 2014; 2 pgs.
NCBI Reference Sequence XM_008262906.1 dated Jun. 13, 2014; 2 pgs.
NCBI Reference Sequence XM_009299847.1 dated Sep. 24, 2014; 2 pgs.
NCBI Reference Sequence XM_009451226.1 dated Oct. 8, 2014; 2 pgs.
NCBI Reference Sequence XM_010818171.1 dated Dec. 30, 2014; 2 pgs.
NCBI Reference Sequence XM_010818172.1 dated Dec. 30, 2014; 2 pgs.
Oakley, H. et al., "Intraneuronal beta-Amyloid Aggregates, Neurodegeneration, and Neuron Loss in Transgenic Mice with Five Familial Alzheimer's Disease Mutations: Potential Factors in Amyloid Plaque Formation," J. Neurosci., Oct. 4, 2006, pp. 10129-10140, vol. 26, No. 40.
Otero, K. et al., "Macrophage colony-stimulating factor induces the proliferation and survival of macrophages via a pathway involving DAP12 and beta-catenin," Nat. Immunol., Jul. 2009, pp. 734-743, vol. 10, No. 7, with Online Methods, 1 pg.
Otero, K. et al., "TREM2 and beta-Catenin Regulate Bone Homeostasis by Controlling the Rate of Osteoclastogenesis," J. Immunol., 2012, pp. 2612-2621, vol. 188, with Corrections, 1 pg.
Pacak, C. et al., "Recombinant Adeno-Associated Virus Serotype 9 Leads to Preferential Cardiac Transduction In Vivo," Circ. Res., 2006, pp. e3-e9, vol. 99, No. 4.
Takahaski, et al., Clearance of Apoptotic Neurons without Inflammation by Microglial Triggering Receptor Expressed on Myeloid Cells-2, The Journal of Experimental Medicine, The Rockefeller University Press, vol. 201, No. 4 Feb. 21, 2005, pp. 647-657.

(56) References Cited

OTHER PUBLICATIONS

Otero, et al, Macrophage Colony-Stimulating Factor Induces the Proliferation and survival of Macrophages via a Pathway Involving DAP12 and β-catenin, Nature Immunology, vol. 10, No. 7, pp. 734-743.

Peng, et al., Trem2- and DAP12-Dependent Activation of PI3K Required DAP10 and is Inhibited by SHIP1, Cell Biology, www.Sciencesignaling.org, vol. 3, Issue 122, ra38, May 18, 2010.

Wu, et al., TREM-2 Promotes Macrophage Survival and Lung Disease after Respiratory Viral Infection, The Journal of Experimental Medicine, The Rockefeller University Press, J. Exp. Med., vol. 212, No. 5, 2015, pp. 681-697.

Wang, et aL, TREM2 Lipid Sensing Sustains the Microglial Response in an Alzheimer's Disease Model, CellPress, vol. 160, Mar. 12, 2016, pp. 1061-1071.

Zhong, et al., Soluble TREM2 Induces Inflammatory Responses and Enhances Microglial Survival, The Journal of Experimental Medicine, The Rockefeller University Press, J. Exp. Med., vol. 214, No. 3, 2017, pp. 597-607.

Song, et al., Humanized TREM2 Mice Reveal Microglia-Intrinsic and -Extrinsic Effects of R47H Polymorphism, The Journal of Experimental Medicine, The Rockefeller University Press, J. Exp. Med, vol. 215, No. 3 2018, pp. 745-760.

Thong, et al., Soluble TREM2 Ameliorates Pathological Phenotypes by Modulating Microglial Functions in an Alzheimer's Disease Model, Nature Communications, vol. 10, No. 1365, 2019, pp. 1-16.

The Overview of Fc Receptors-Classification, Related Signaling Pathways and Application, Cusabio Technology LLC, 7480, Dec. 25, 2018, p. 1-21.

\* cited by examiner

FIG. 1A
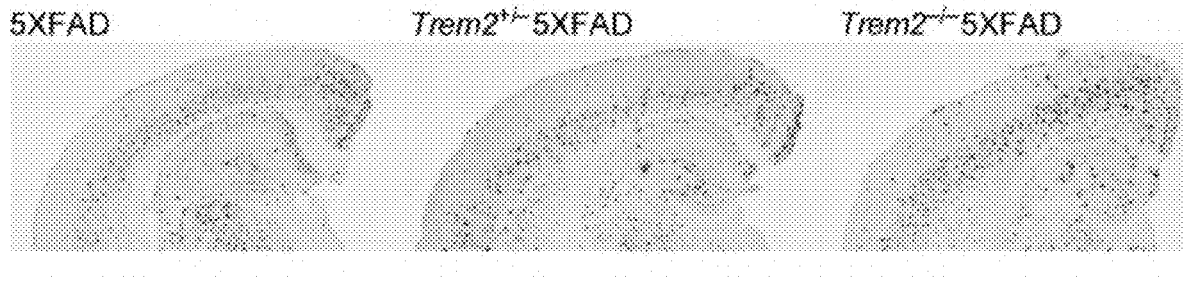
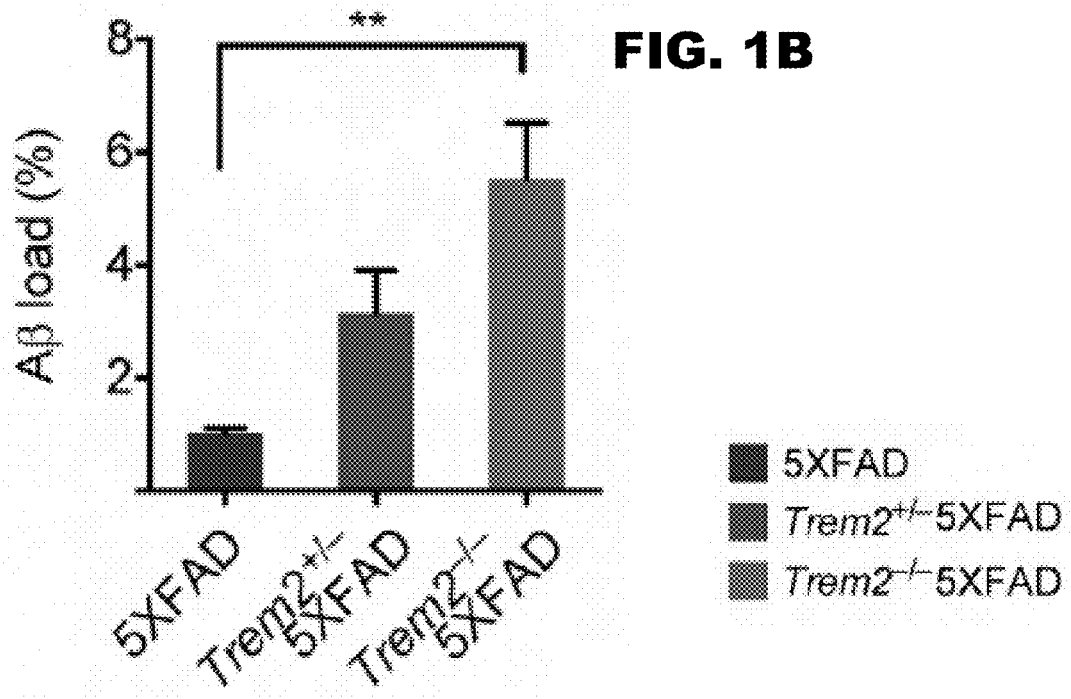
FIG. 1B
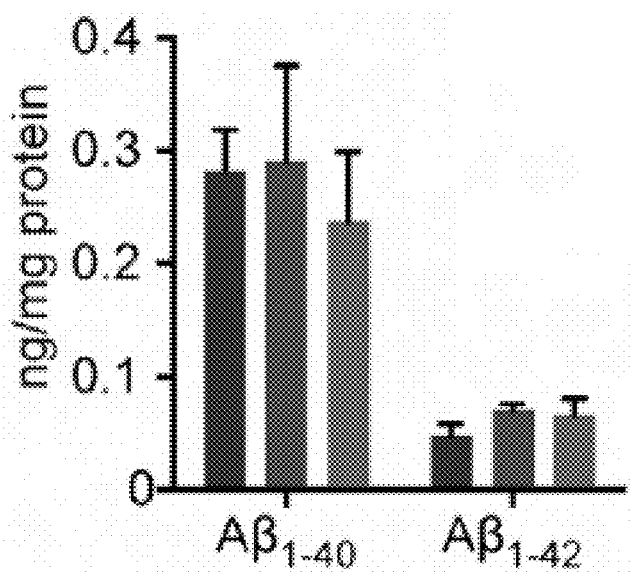
FIG. 1C

FIG. 3C
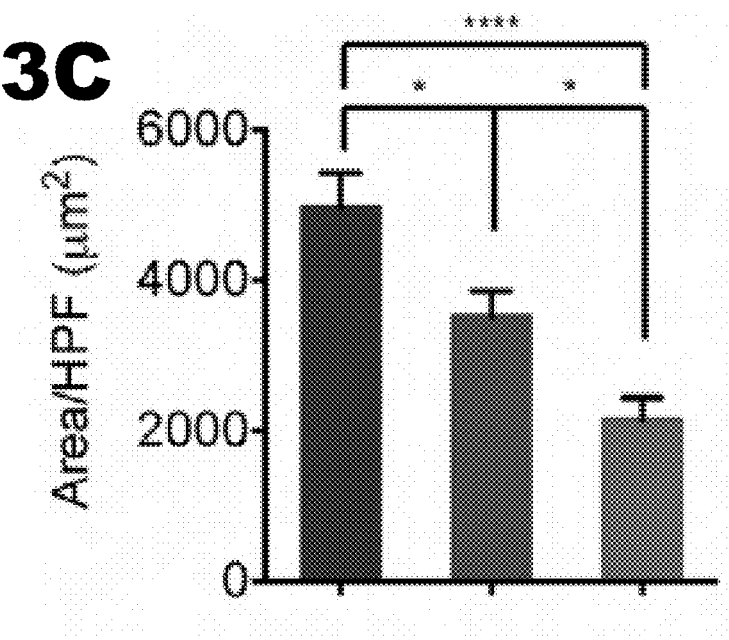
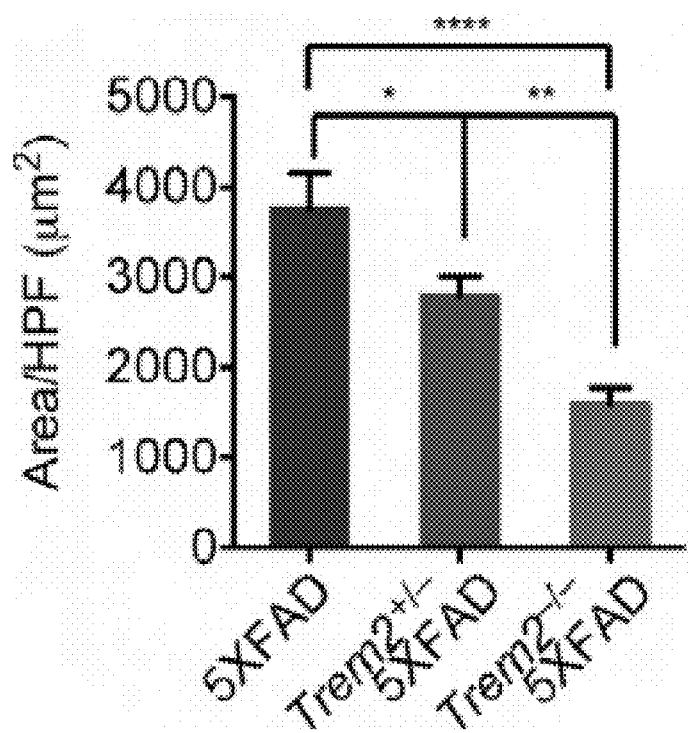
FIG. 3D

FIG. 5A
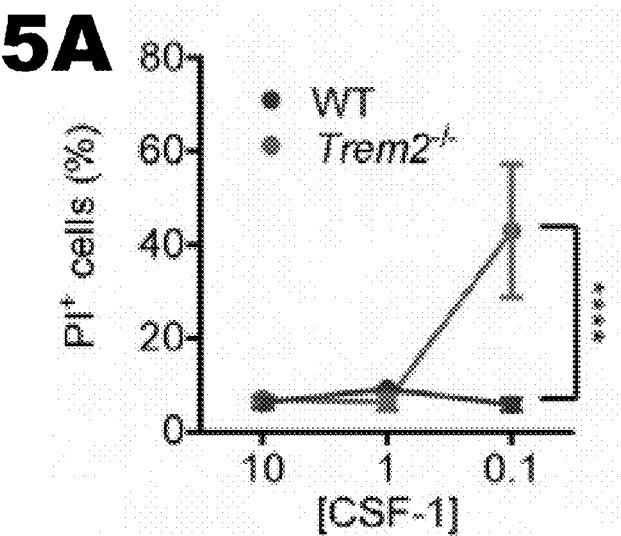
FIG. 5B
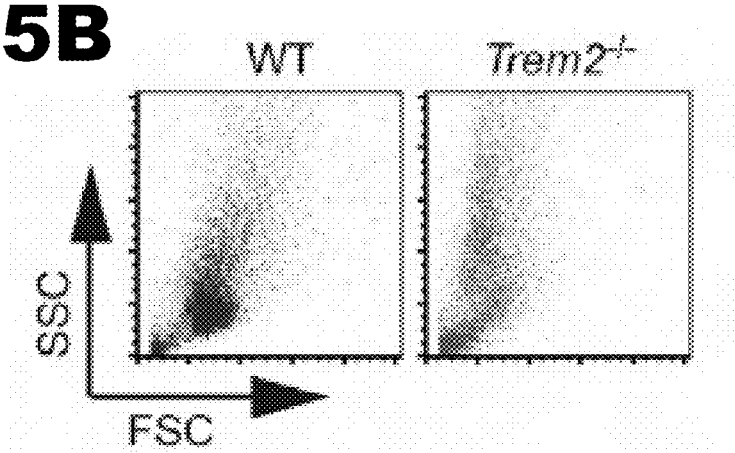
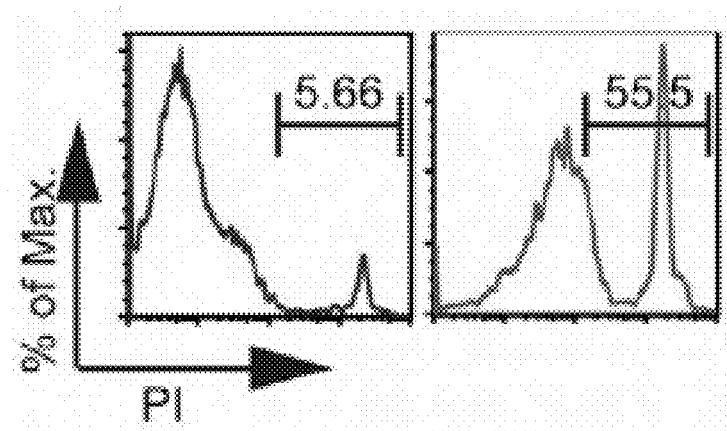
FIG. 5C

FIG. 5E
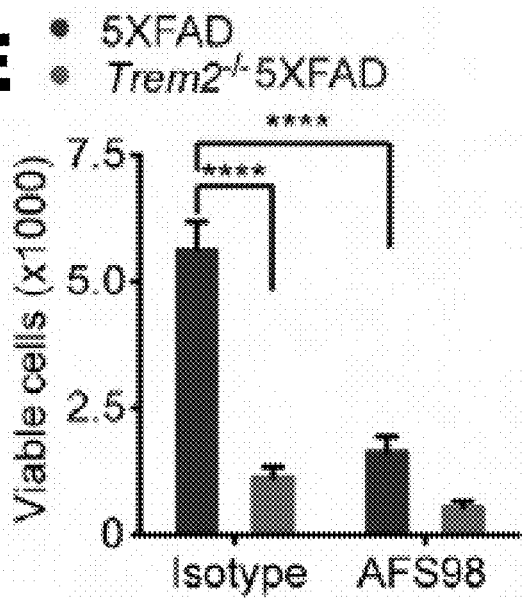
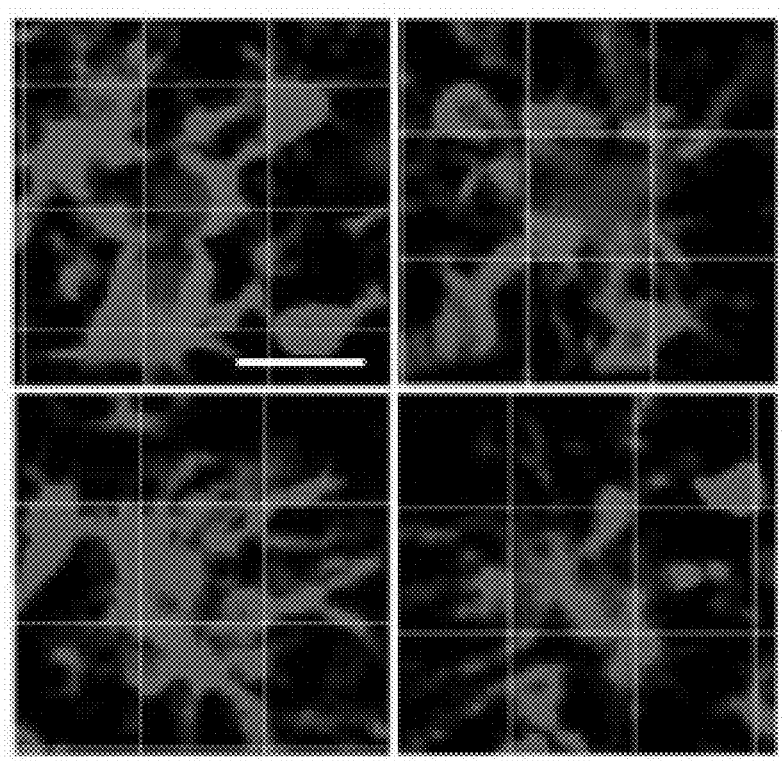
FIG. 5F

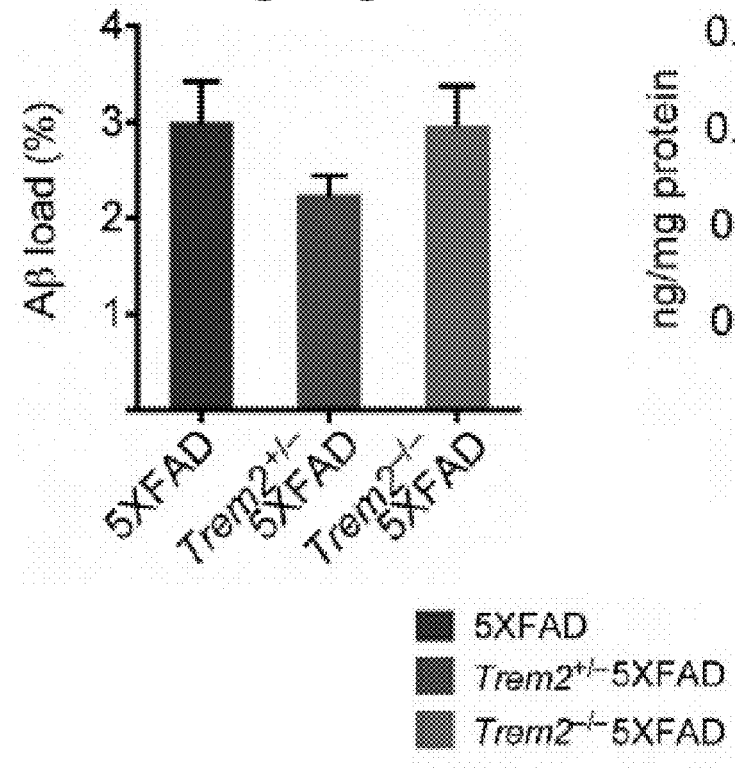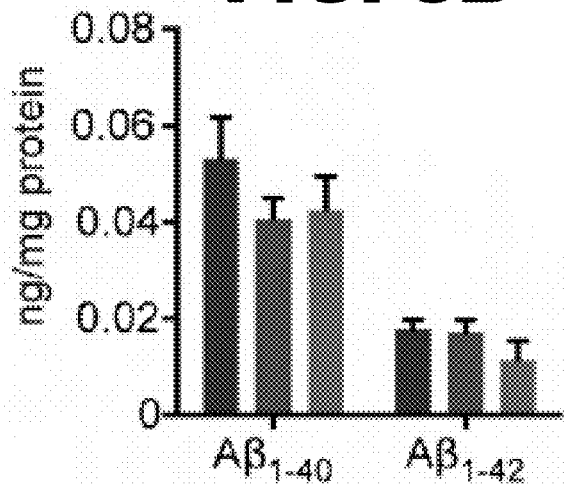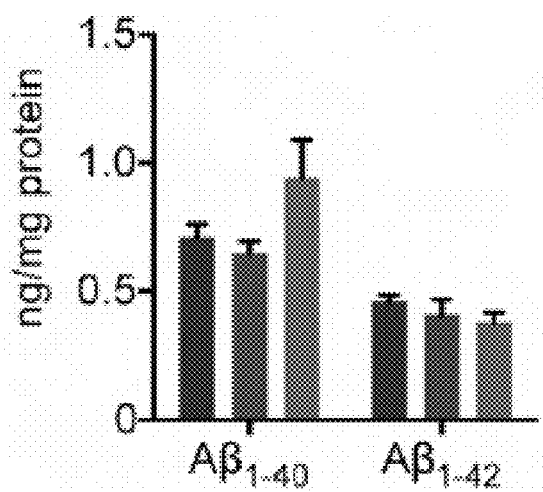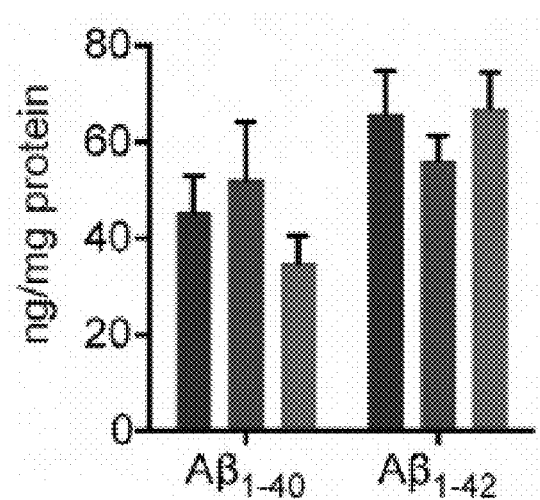
FIG. 8A
FIG. 8B
FIG. 8C
FIG. 8D

● 5XFAD
● Trem2⁻/⁻5XFAD

SEQUENCE LISTING

```
<160> NUMBER OF SEQ ID NOS: 4

<210> SEQ ID NO 1
<211> LENGTH: 172
<212> TYPE: PRT
<213> ORGANISM: Artificial Sequence
<220> FEATURE:
<223> OTHER INFORMATION: SYNTHESIZED

<400> SEQUENCE: 1

Met Glu Pro Leu Arg Leu Leu Ile Leu Leu Phe Val Thr Glu Leu Ser
1               5                   10                  15
```

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
            115                 120                 125

Leu Ala Asp Pro Leu Asp His Arg Asp Ala Gly Asp Leu Trp Phe Pro
        130                 135                 140

Gly Glu Ser Glu Ser Phe Glu Asp Ala His Val Glu His Ser Ile Ser
145                 150                 155                 160

Arg Ala Glu Arg His Val Lys Glu Asp Asp Gly Arg
                165                 170

<210> SEQ ID NO 2
<211> LENGTH: 132
<212> TYPE: PRT
<213> ORGANISM: Artificial Sequence
<220> FEATURE:
<223> OTHER INFORMATION: SYNTHESIZED

<400> SEQUENCE: 2

Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
            115                 120                 125

Leu Ala Asp Pro
        130

<210> SEQ ID NO 3
<211> LENGTH: 1012
<212> TYPE: DNA
<213> ORGANISM: Homo sapiens

<400> SEQUENCE: 3
ccttggctgg ggaagggtgg catggagcct ctccggctgc tcatcttact ctttgtcaca      60
gagctgtccg gagcccacaa caccacagtg ttccagggcg tggcgggcca gtccctgcag     120

```
gtgtcttgcc cctatgactc catgaagcac tgggggaggc gcaaggcctg gtgccgccag    180
ctgggagaga agggcccatg ccagcgtgtg gtcagcacgc acaacttgtg gctgctgtcc    240
ttcctgagga ggtggaatgg gagcacagcc atcacagacg ataccctggg tggcactctc    300
accattacgc tgcggaatct acaacccat gatgcgggtc tctaccagtg ccagagcctc    360
catggcagtg aggctgacac cctcaggaag gtcctggtgg aggtgctggc agacccctg    420 gatcaccggg atgctggaga tctctggttc cccggggagt ctgagagctt cgaggatgcc    480
catgtggagc acagcatctc caggccatct caaggctccc atctgccttc ttgtctctcc    540
aaggagcctc ttggaaggag aaatcccctt cccacccact ccatccttc tcctcctggc    600 ctgcatcttt ctcatcaaga ttctagcagc cagcgccctc tgggctgcag cctggcatgg    660
acagaagcca gggacacatc cacccagtga actggactgt ggccatgacc cagggtatca    720
gctccaaact ctgccagggc tgagagacac gtgaaggaag atgatgggag gaaaagccca    780
ggagaagtcc caccagggac cagcccagcc tgcatacttg ccacttggcc accaggactc    840
cttgttctgc tctggcaaga gactactctg cctgaacact gcttctcctg gaccctggaa    900
gcagggactg gttgagggag tggggaggtg gtaagaacac ctgacaactt ctgaatattg    960
gacattttaa acacttacaa ataaatccaa gactgtcata tttagctgga ta    1012
```

<210> SEQ ID NO 4
<211> LENGTH: 222
<212> TYPE: PRT
<213> ORGANISM: Artificial Sequence
<220> FEATURE:
<223> OTHER INFORMATION: SYNTHESIZED

<400> SEQUENCE: 4

```
Met Glu Pro Leu Arg Leu Leu Ile Leu Leu Phe Val Thr Glu Leu Ser
1               5                   10                  15

Gly Ala His Asn Thr Thr Val Phe Gln Gly Val Ala Gly Gln Ser Leu
            20                  25                  30

Gln Val Ser Cys Pro Tyr Asp Ser Met Lys His Trp Gly Arg Arg Lys
        35                  40                  45

Ala Trp Cys Arg Gln Leu Gly Glu Lys Gly Pro Cys Gln Arg Val Val
    50                  55                  60

Ser Thr His Asn Leu Trp Leu Leu Ser Phe Leu Arg Arg Trp Asn Gly
65                  70                  75                  80

Ser Thr Ala Ile Thr Asp Asp Thr Leu Gly Gly Thr Leu Thr Ile Thr
                85                  90                  95

Leu Arg Asn Leu Gln Pro His Asp Ala Gly Leu Tyr Gln Cys Gln Ser
            100                 105                 110

Leu His Gly Ser Glu Ala Asp Thr Leu Arg Lys Val Leu Val Glu Val
        115                 120                 125

Leu Ala Asp Pro Leu Asp His Arg Asp Ala Gly Asp Leu Trp Phe Pro
    130                 135                 140

Gly Glu Ser Glu Ser Phe Glu Asp Ala His Val Glu His Ser Ile Ser
145                 150                 155                 160

Arg Pro Ser Gln Gly Ser His Leu Pro Ser Cys Leu Ser Lys Glu Pro
                165                 170                 175
```

-continued

```
Leu Gly Arg Arg Asn Pro Leu Pro Thr His Phe His Pro Ser Pro Pro
            180                 185                 190

Gly Leu His Leu Ser His Gln Asp Ser Ser Gln Arg Pro Leu Gly
        195                 200                 205

Cys Ser Leu Ala Trp Thr Glu Ala Arg Asp Thr Ser Thr Gln
        210                 215                 220
```

COMPOSITIONS COMPRISING TREM2 AND METHODS OF USE THEREOF

CROSS REFERENCE TO RELATED APPLICATIONS

This application claims the benefit of PCT Application PCT/US2017/019480, filed Feb. 24, 2017, which claims priority from U.S. Provisional Application No. 62/299,849, filed Feb. 25, 2016, each of the disclosures of which are hereby incorporated by reference in their entirety.

FIELD OF THE INVENTION

The present invention relates to TREM2 fusion proteins and uses thereof.

BACKGROUND OF THE INVENTION

Triggering receptor expressed on myeloid cells 2 (TREM2) is a microglial surface receptor that triggers intracellular protein tyrosine phosphorylation. Recent genome-wide association studies have shown that a rare R47H mutation of TREM2 correlates with a substantial increase in the risk of developing Alzheimer's disease (AD). TREM2 deficiency and haploinsufficiency augments β-amyloid (Aβ) accumulation due to a dysfunctional response of microglia, which fail to cluster around Aβ plaques and become apoptotic. Thus, there is a need in the art to identify compounds and methods to restore function of TREM2 as well as identify agonists that can restore function of mutant TREM2.

SUMMARY OF THE INVENTION

One aspect of the invention encompasses a polynucleotide sequence encoding a polypeptide, wherein the polypeptide comprises at least one TREM2 or fragment thereof and a targeting moiety, and optionally comprising a signal peptide and/or a purification moiety, wherein the targeting moiety binds to an Fc receptor. In another aspect the targeting moiety is an IgG Fc fragment. In another aspect the extracellular domain of TREM2 may comprise the amino acid sequence selected from the group consisting of SEQ ID NO:1 and SEQ ID NO:2. In another aspect, the extracellular domain may have at least 80%, at least 85%, at least 90%, at least 95%, at least 98%, at least 99% or more sequence identity to SEQ ID NO:1 or SEQ ID NO:2.

In another aspect the polypeptide comprises a signal peptide at the N-terminus. In another aspect the polypeptide may comprise a purification moiety at the C-terminus.

In an aspect the invention encompasses an isolated polypeptide sequence encoded by the polynucleotide sequence. In an aspect the invention encompasses a vector comprising a polynucleotide sequence encoding the polypeptide sequence. In another aspect the invention encompasses an isolated cell comprising a polynucleotide sequence encoding the polypeptide sequence. In another aspect the invention encompasses an isolated cell comprising a vector comprising a polynucleotide sequence encoding the polypeptide sequence.

In an aspect the invention encompasses a method of delivering a polynucleotide to a cell, wherein the polynucleotide encodes a polypeptide comprising at least one TREM2 or fragment thereof and a targeting moiety.

In an aspect the invention encompasses a method of delivering or targeting TREM2 to an Fc receptor on a microglial cell in a subject, the method comprising administering to the subject a composition comprising an isolated polypeptide comprising at least one TREM2 or fragment thereof attached to a targeting moiety.

In an aspect the invention encompasses a method of restoring the function of TREM2 in a subject, the method comprising administering to the subject a composition comprising an isolated polypeptide comprising at least one TREM2 or fragment thereof attached to a targeting moiety. In another aspect the TREM2 domain may be the extracellular domain of TREM2. In another aspect the extracellular domain of TREM2 comprises the amino acid sequence selected from the group consisting of SEQ ID NO:1 and SEQ ID NO:2. In another aspect the targeting moiety is an Fc fragment.

In an aspect the invention encompasses a method for preventing, in a subject, a disease or condition associated with aberrant expression or activity of TREM2, the method comprising administering to the subject a composition comprising an isolated polypeptide comprising at least one TREM2 or fragment thereof attached to a targeting moiety.

In an aspect the invention encompasses a method of modulating expression or activity of TREM2 for therapeutic purposes, the method comprising administering to a subject a composition comprising an isolated polypeptide comprising at least one TREM2 or fragment thereof attached to a targeting moiety. In another aspect the disease or condition may be associated with loss-of-function of TREM2. In another aspect the loss-of-function of TREM2 may be due to an R27H mutation relative to SEQ ID NO:4. In another aspect the disease or disorder is a neurodegenerative disease selected from the group consisting of Alzheimer's disease, frontotemporal dementia, Huntington's disease, Parkinson's disease, amyotrophic lateral sclerosis and Nasu-Hakola disease.

In an aspect the invention encompasses a reporter cell, wherein the reporter cell expresses a membrane-bound form of TREM2, or a biologically active portion thereof, on the cell surface, wherein the TREM2 optionally comprises a R47H mutation relative to SEQ ID NO:4 and the cells further comprise a reporter protein operably linked to a promoter that is responsive to a protein that is induced by PLCγ/$Ca^{2+}$.

BRIEF DESCRIPTION OF THE FIGURES

The application file contains at least one drawing executed in color. Copies of this patent application publication with color drawing(s) will be provided by the Office upon request and payment of the necessary fee.

FIG. 1A, FIG. 1B, FIG. 1C, FIG. 1D, FIG. 1E, FIG. 1F, and FIG. 1G, depict graphs and images showing that TREM2-deficient 5×FAD mice have increased hippocampal Aβ burden and accelerated loss of layer V cortical neurons. Aβ burden in 8.5-month-old Trem2$^{-/-}$5×FAD, Trem2$^{+/-}$5×FAD, and 5×FAD mice. (FIG. 1A) Matching coronal hippocampus and cortex sections were stained with an Aβ-specific antibody mHJ3.4. (FIG. 1B) Amounts of Aβ loads in hippocampi. (FIG. 1C, FIG. 1D, and FIG. 1E) Soluble and insoluble A$β_{1-40}$ and A$β_{1-42}$ levels in hippocampi as detected by ELISA. (FIG. 1C) PBS fraction; (FIG. 1D) Triton-X fraction; and (FIG. 1E) Guanidine fraction. (FIG. 1F, and FIG. 1G) Densities of layer V neurons in 8.5-month-old Trem2$^{-/-}$5×FAD, Trem2$^{+/-}$5×FAD, and 5×FAD mice. (FIG. 1F) Matching coronal sections stained with cresyl violet. (FIG. 1G) Summary of densities of layer V neurons. Original magnification: 10×; scale bar, 100 pm. *$p<0.05$, p<0.01, *p<0.001, ****p<0.0001, one-way ANOVA. Data represent analyses total of eight to ten 5×FAD mice, eight to 12 Trem2$^{+/-}$5×FAD mice, and eight to 16 Trem2$^{-/-}$5×FAD mice (FIG. 1B, FIG. 1C, FIG. 1D, FIG. 1E, FIG. 1G). Bars represent mean±SEM.

Figure 2A:
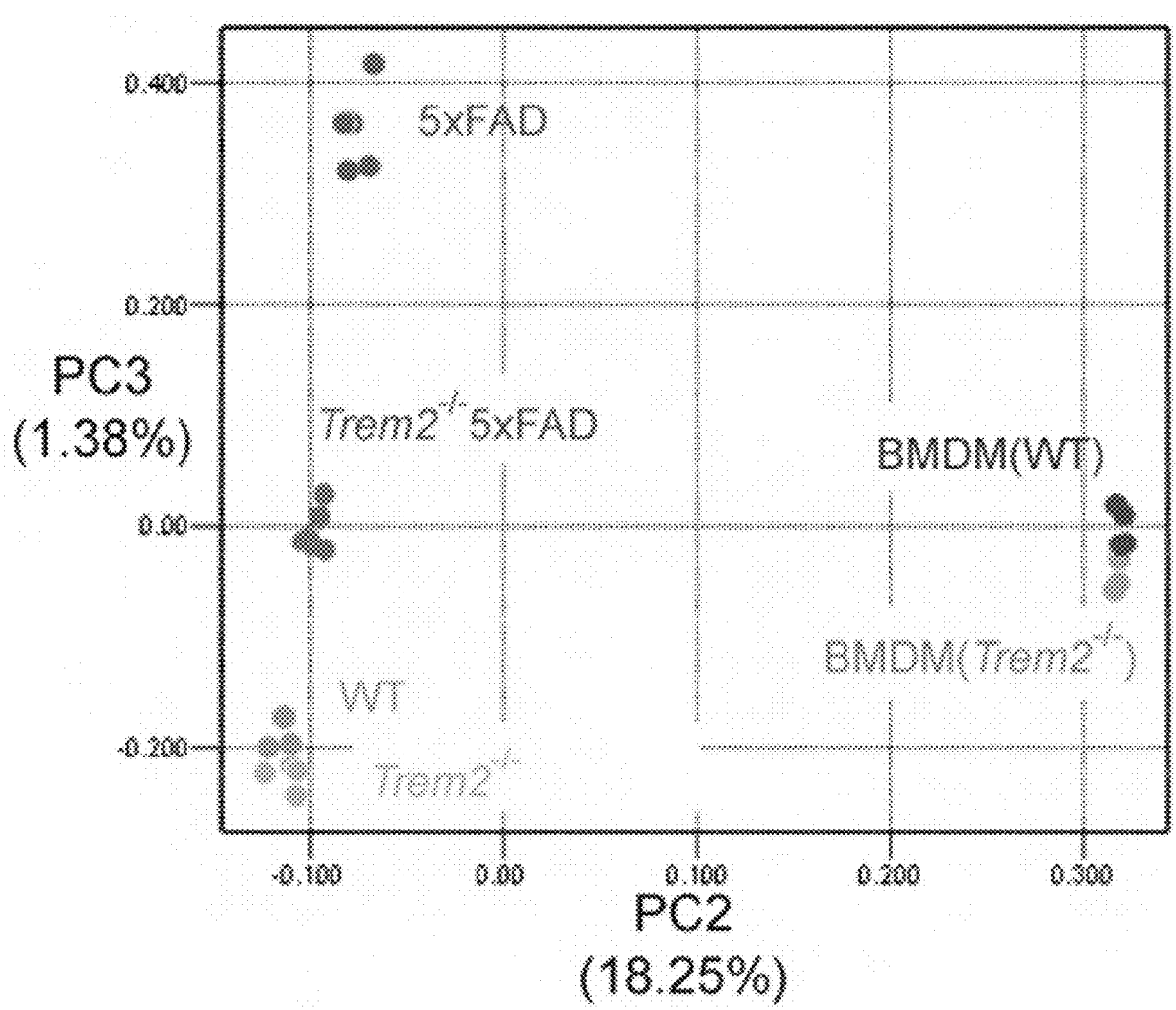
Figure 2B:
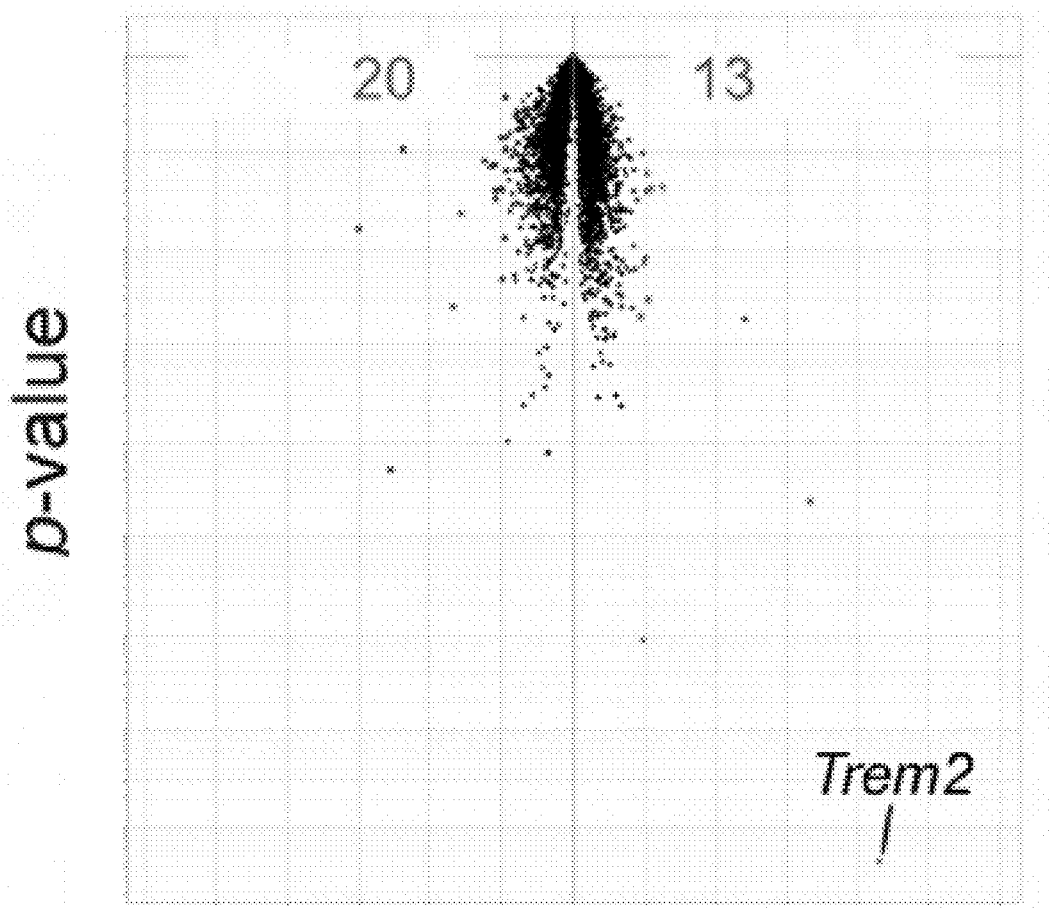
Figure 2C:
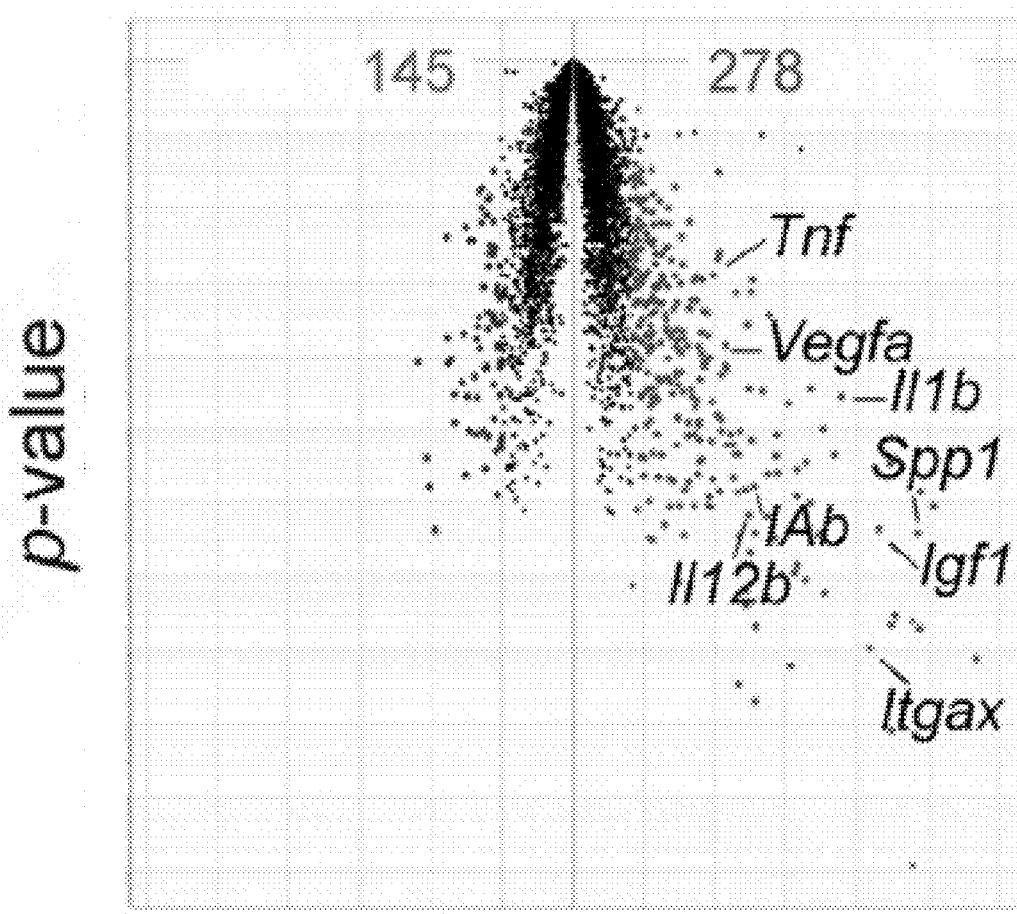

FIG. 2A, FIG. 2B, FIG. 2C, FIG. 2D, FIG. 2E, and FIG. 2F, depict graphs and a heatmap showing that TREM2 deficiency impairs Aβ-induced transcriptional program in microglia. Transcriptional analysis of microglia isolated from hippocampi and cortices of 8.5-month-old Trem2$^{-/-}$5×FAD, 5×FAD, Trem2$^{-/-}$, and WT mice. (FIG. 2A) Top 15% most variable transcripts were subjected to principle component analysis (PCA). Plot shows two-dimensional (PC2 versus PC3) comparison of transcriptional changes in all classes analyzed. WT and Trem2$^{-/-}$ bone marrow-derived macrophages were used as references. (FIG. 2B) Volcano plot comparing microglial transcripts in Trem2$^{-/-}$ and WT mice. Trem2 transcript is indicated. (FIG. 2C) Volcano plot comparing microglial transcripts in 5×FAD and WT mice. Numbers in plots (FIG. 2B) and (FIG. 2C) indicate probes that are significantly upregulated or downregulated (±2-fold, p<0.05, Student's t test). Representative transcripts are indicated. (FIG. 2D, FIG. 2E, FIG. 2F) Visualization of Aβ-induced changes in microglial transcripts from (FIG. 2C). (FIG. 2D, FIG. 2E) A heatmap displays hierarchical clustering of all samples analyzed. (FIG. 2F) A scatterplot compares these transcriptional changes in Trem2$^{-/-}$5×FAD and 5×FAD microglia. Representative transcripts are shown.

Figure 3A:
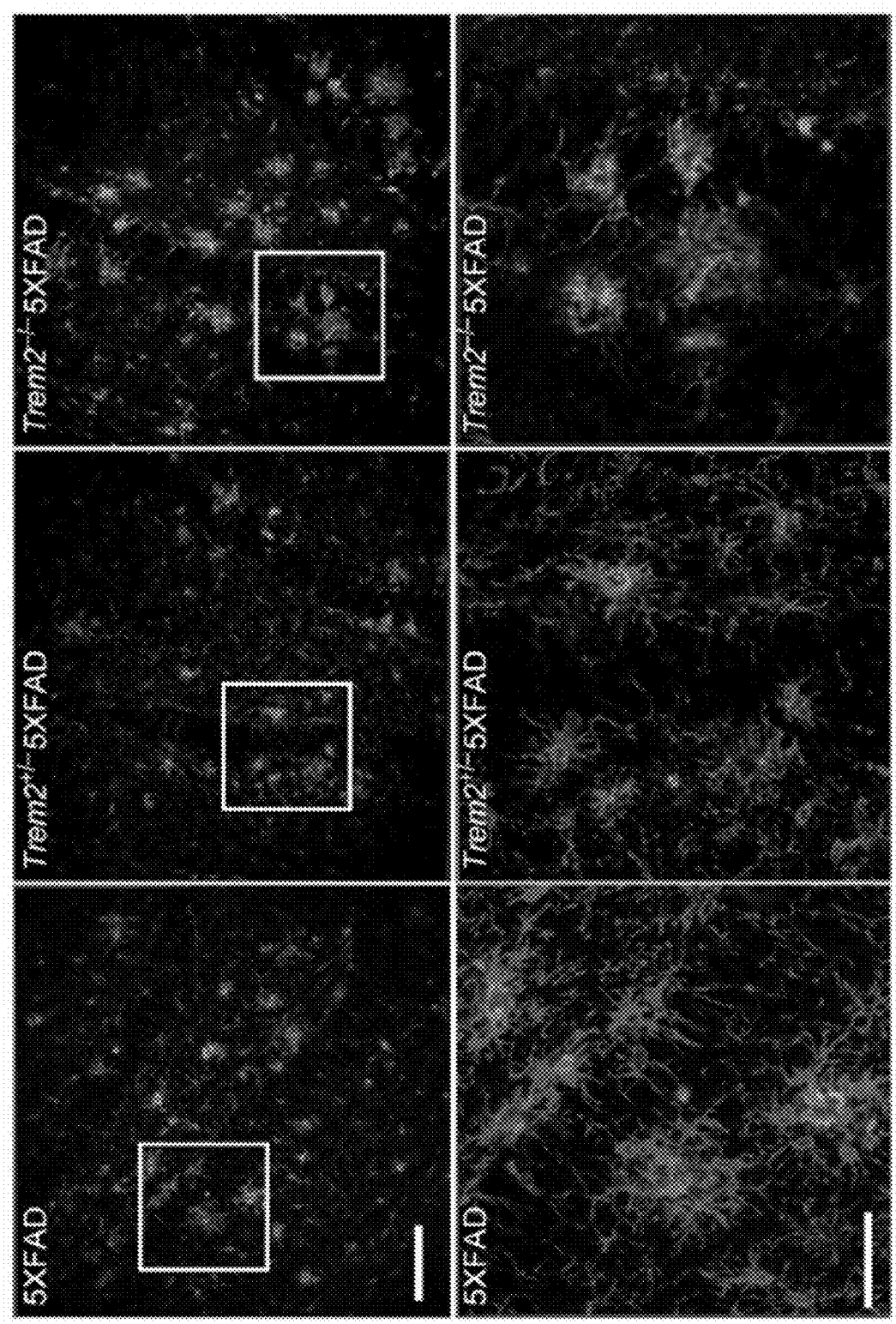
Figure 3B:
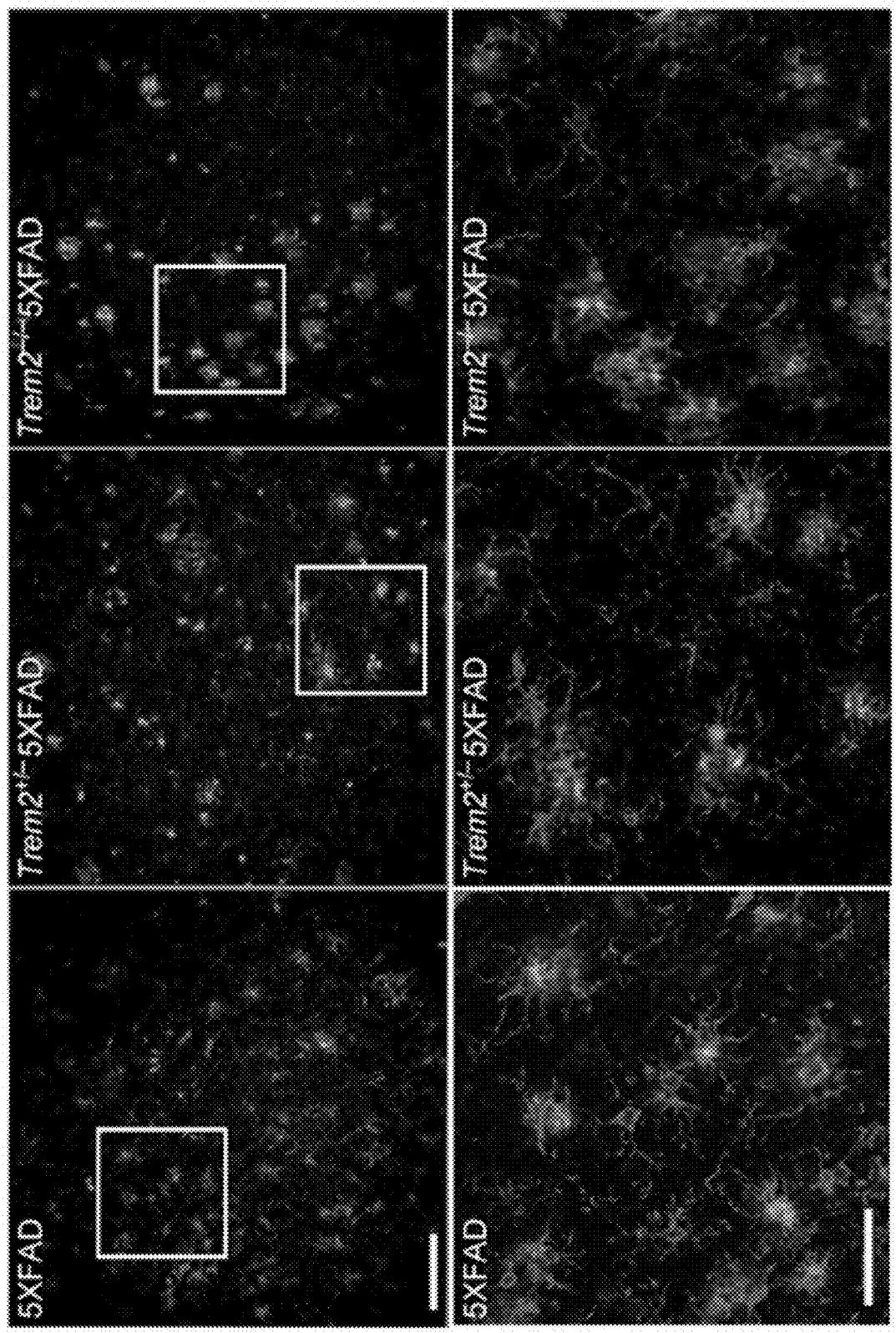
Figures 3E, 3F:
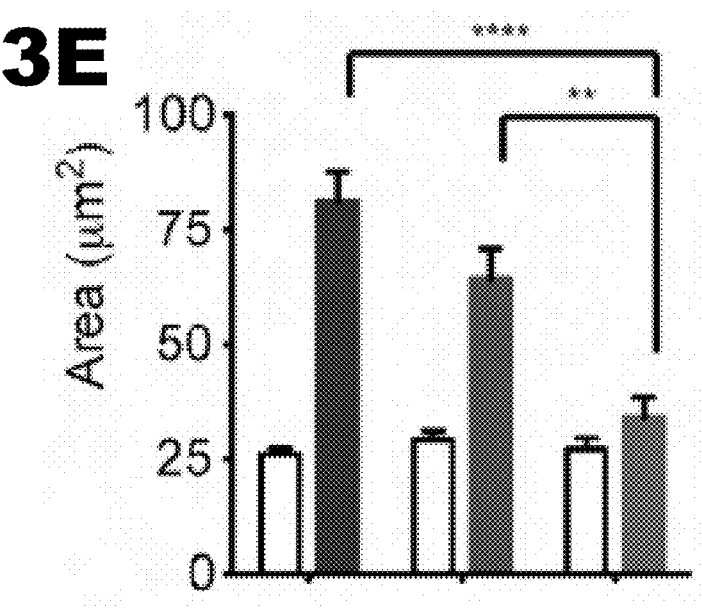

FIG. 3A, FIG. 3B, FIG. 3C, FIG. 3D, FIG. 3E, and FIG. 3F depict images and graphs showing TREM2 deficiency leads to reduced microgliosis in 5×FAD mice. Microgliosis in 8.5-month-old Trem2$^{-/-}$5×FAD, Trem2$^{+/-}$5×FAD, and 5×FAD mice. (FIG. 3A, FIG. 3B) Matching coronal sections were stained with Iba-1 (red) for microglia and X-34 (green) for amyloid plaques. Representative Z-stack images with maximum projection are shown. (FIG. 3C, FIG. 3D) Quantification of total Iba-1 reactivity per high-power field (HPF) in hippocampi (FIG. 3C) and cortices (FIG. 3D). (FIG. 3E, and FIG. 3F) Quantification of microgliosis associated with plaques of similar sizes in hippocampi (FIG. 3E) and cortices (FIG. 3F). Original magnification 20× (FIG. 3A, FIG. 3B, upper panels), 40× (FIG. 3A, FIG. 3B, lower panels); scale bar, 10 μm (FIG. 3A, FIG. 3B, upper panels), 50 μm (FIG. 3A, FIG. 3B, lower panels). *p<0.05, p<0.01, *p<0.0001, one-way ANOVA. Data represent analyses of a total of eight often 5×FAD, eight of 12 Trem2+/−5×FAD mice, and eight of 16 Trem2−/−5×FAD mice. Bars represent mean±SEM.

Figure 4A:
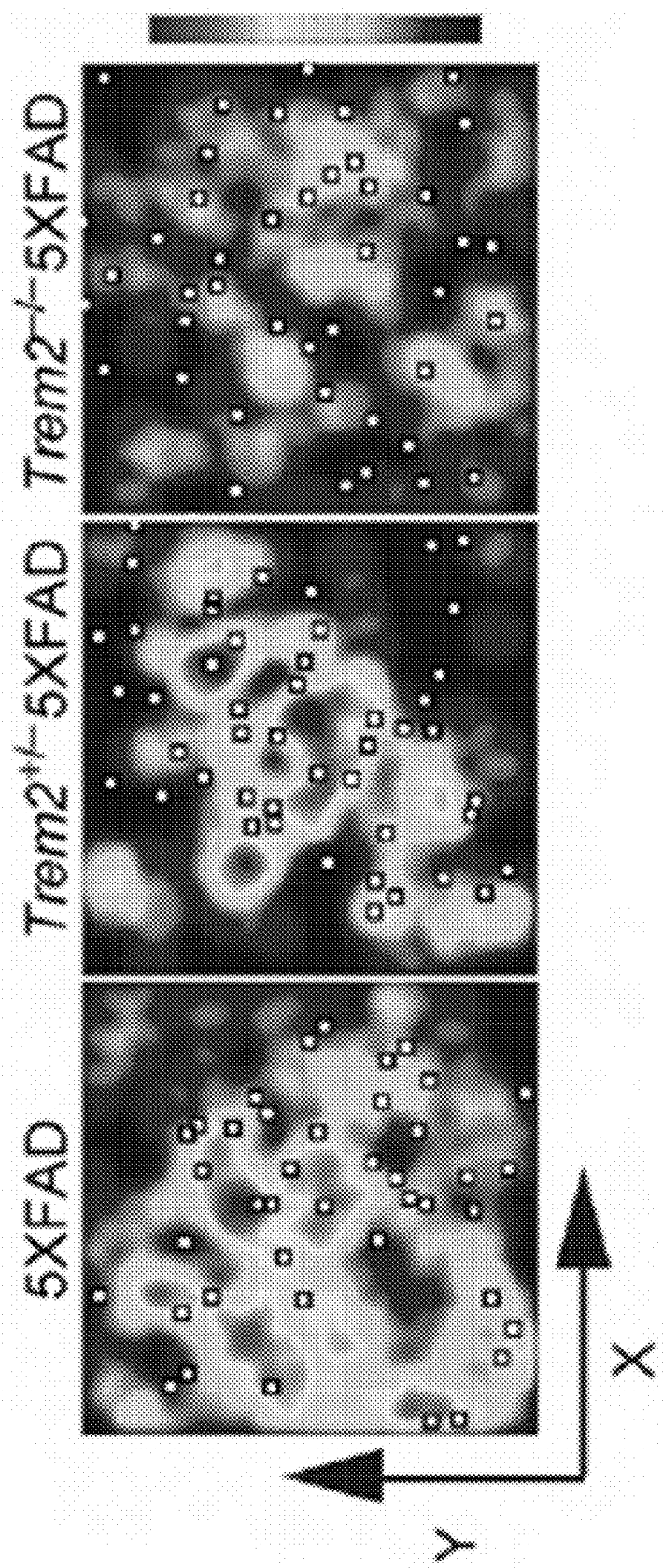
Figure 4B:
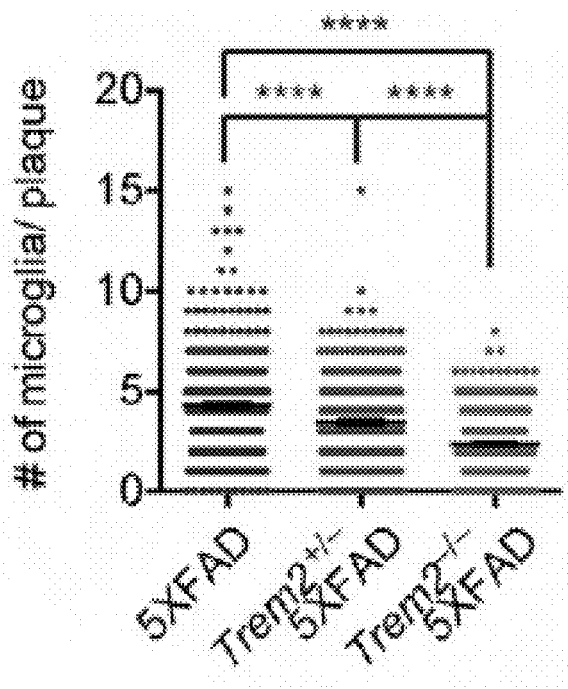
Figure 4C:
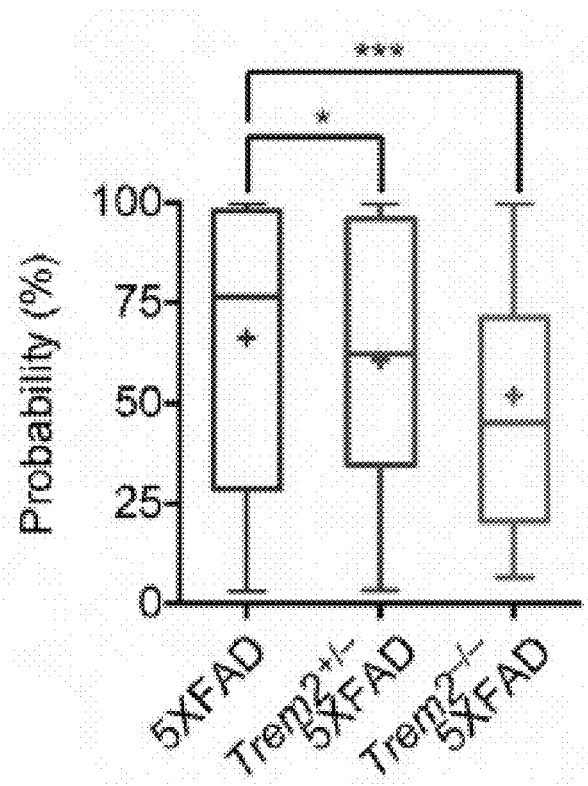
Figure 4D:
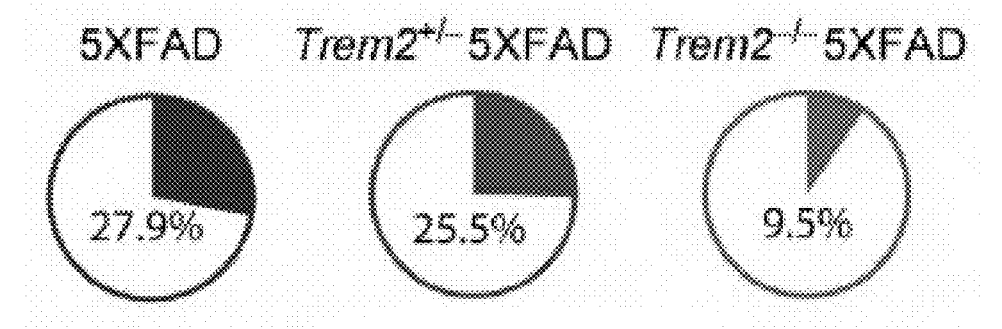
Figure 4E:
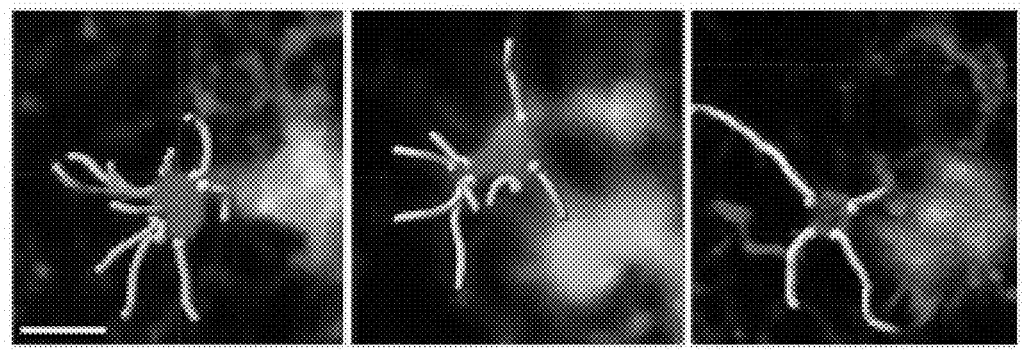
Figure 4F:
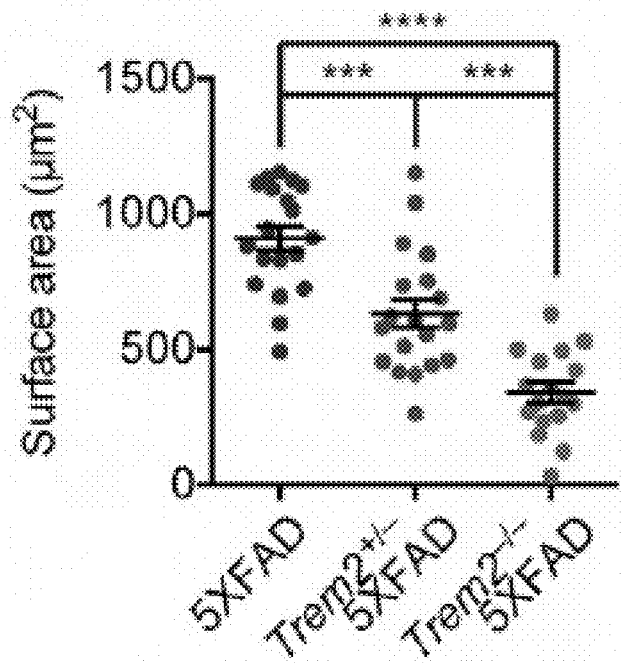
Figure 4G:
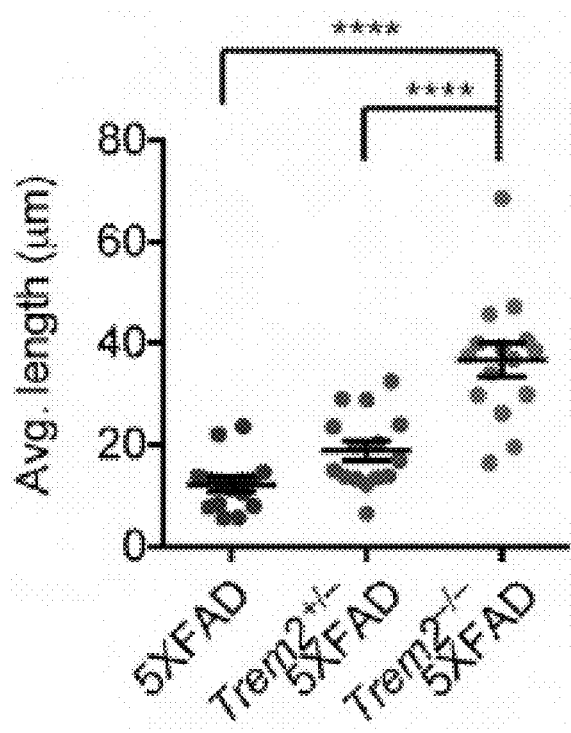

FIG. 4A, FIG. 4B, FIG. 4C, FIG. 4D, FIG. 4E, FIG. 4F, FIG. 4G, and FIG. 4H depict images and graphs showing TREM2 deficiency diminishes the capacity of microglia to cluster around Aβ plaques. Frequencies of plaque-associated microglia in 8.5-month-old Trem2$^{-/-}$5×FAD, Trem2$^{+/-}$5×FAD, and 5×FAD mice were determined. (FIG. 4A) Heatmap shows frequencies of microglia in relation to Aβ plaques shown as white squares. (FIG. 4B) Summary of frequencies of plaque-associated microglia in all analyzed genotypes. (FIG. 4C, FIG. 4D) Microglial clustering around plaques in 5×FAD, Trem2$^{+/-}$5×FAD, and Trem2$^{-/-}$5×FAD mice were compared to Monte Carlo simulations that assume total randomness between plaques and microglia. Probabilities that any given microglia-plaque cluster are non-random are shown in (FIG. 4C). Pie charts show frequencies of microglia-plaque clusters that cannot be statistically explained as random (p<0.05) (FIG. 4D). (FIG. 4E) Morphology of plaque-associated microglia highlighting the shape of cell bodies (red) and primary processes (cyan). (FIG. 4F, FIG. 4G, and FIG. 4H) Plaque-associated microglia, are analyzed for their surface area (cell body only), average length of primary processes, and distance from the center of adjacent Aβ plaque. Original magnification: 20×; scale bar, 15 μm. *p<0.05, *p<0.001, **p<0.0001, one-way ANOVA. Data represent analyses of a total seven mice per group (FIG. 4A, FIG. 4B, FIG. 4C, FIG. 4D) and a total of five mice per group (FIG. 4E, FIG. 4F, and FIG. 4G). Bars represent mean±SEM.

Figure 5D:
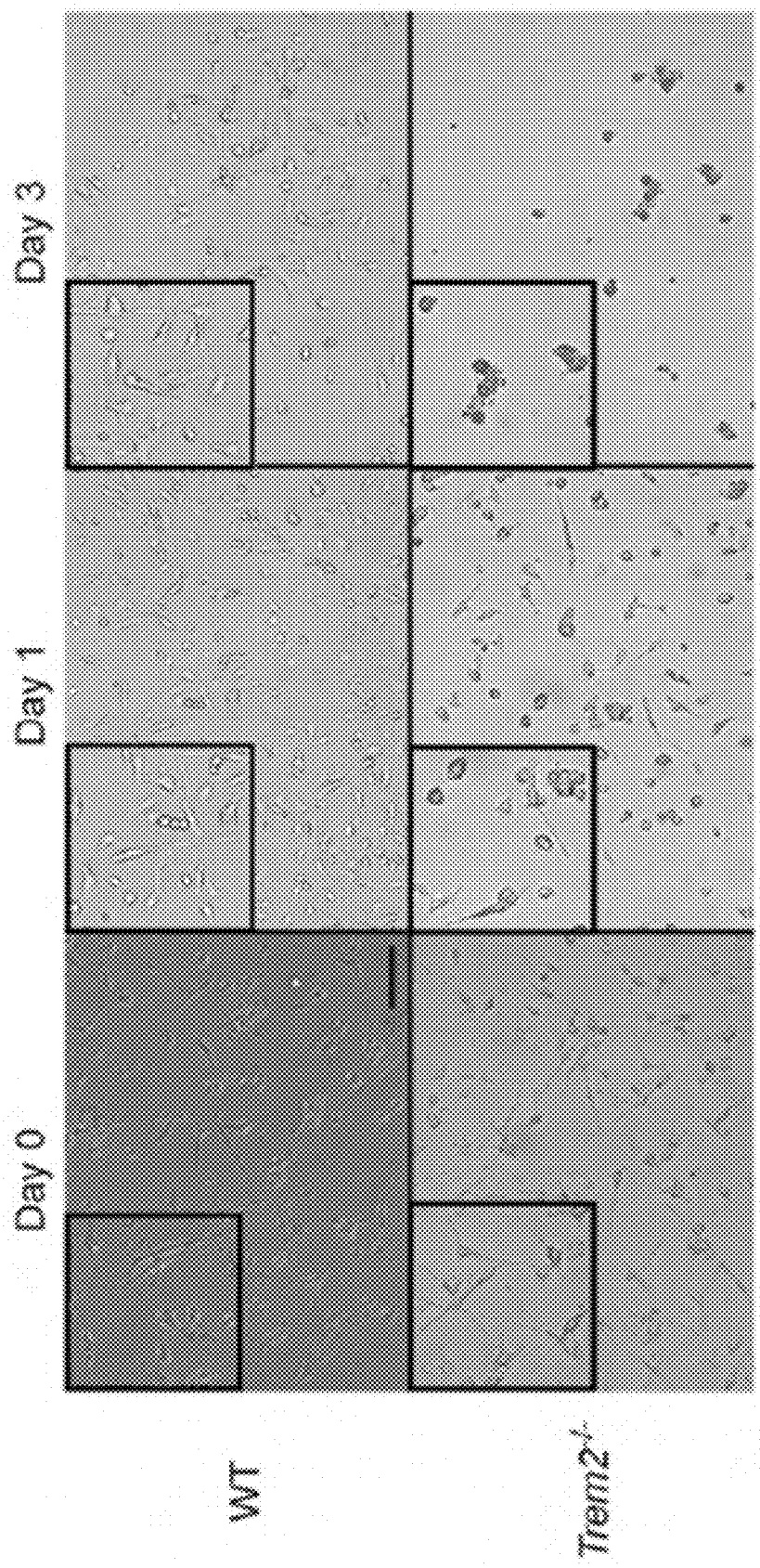
Figure 5G:
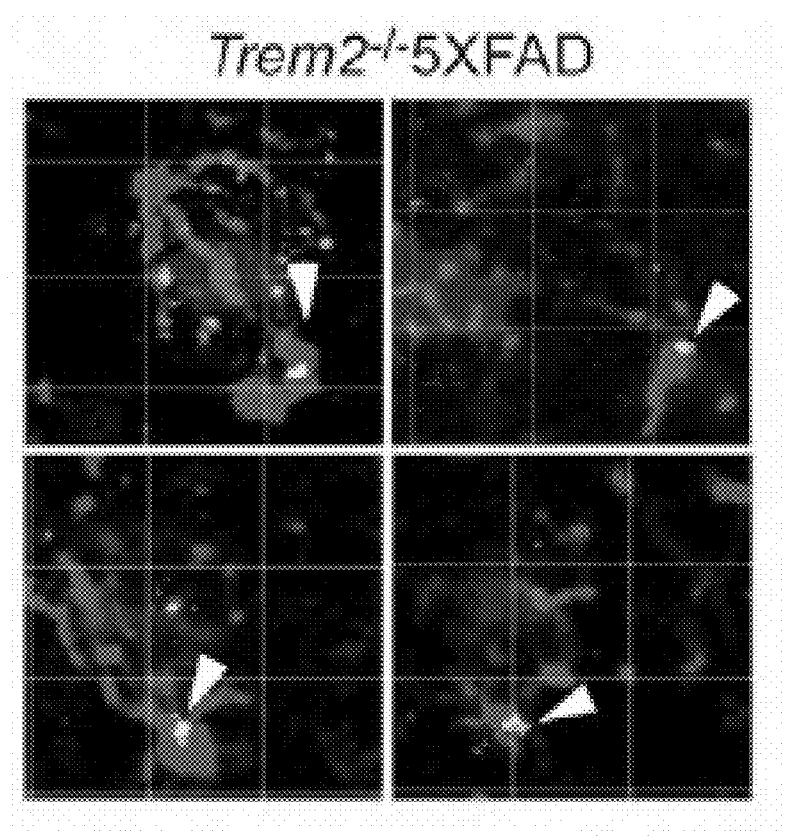
Figure 5H:
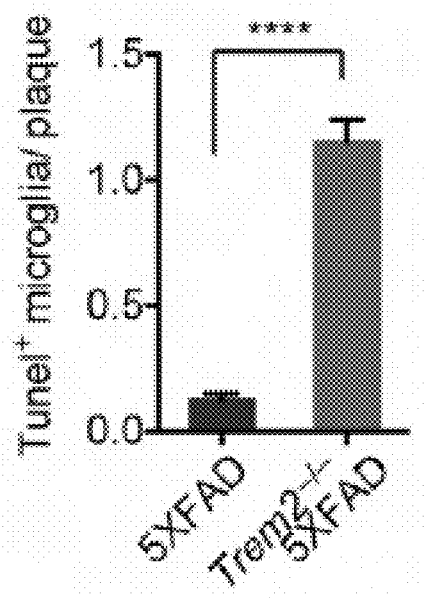
Figure 5I:
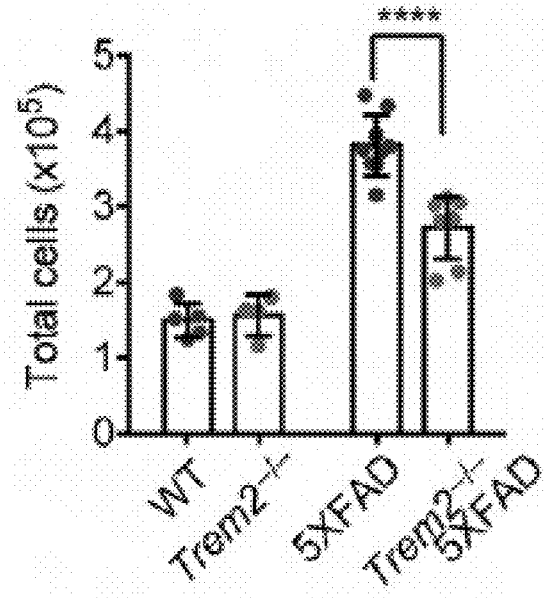

FIG. 5A, FIG. 5B, FIG. 5C, FIG. 5D, FIG. 5E, FIG. 5F, FIG. 5G, FIG. 5H, and FIG. 5I, depict images and graphs showing TREM2 promotes microglial survival ex vivo and in vivo. (FIG. 5 A, FIG. 5B, FIG. 5C, and FIG. 5D) Adult primary microglia were cultured with various concentration of CSF-1-containing L-cell medium (LCM). Viability of microglia by PI staining (FIG. 5 A, FIG. 5B, and FIG. 5C) and morphology (FIG. 5D) were assessed on day 3. Original magnification: 20× (main images), 40× (insets); Scale bar, 10 μm (FIG. 5E) Microglia were purified ex vivo from 5×FAD mice and cultured in 0.1% LCM with or without CSF-1R blocking antibody AFS98. Viability was determined on day 5. (FIG. 5F, FIG. 5G, and FIG. 5H) Apoptosis of plaque-associated microglia (Iba-1, red) in 5×FAD and Trem2-/-5×FAD mice was determined by TUNEL staining (green). Plaques were identified by X-34 (blue). Representative single-stack images of 5×FAD and Trem2$^{-/-}$5×FAD microglia (FIG. 5F, and FIG. 5G) and summary of frequencies of TUNEL microglia associated with plaques (H) are shown. Original magnification: 20×; scale bar, 15 μm (FIG. 5F, and FIG. 5G). (FIG. 5I) Total numbers of live microglia in cortices and hippocampi of 5×FAD, Trem2$^{-/-}$5×FAD, Trem2$^{-/-}$, and WT mice ****p<0.0001, two-way ANOVA (FIG. 5 A, FIG. 5E, and FIG. 5I), Student's t test (H). Data represent a total of three independent experiments (FIG. 5 A, FIG. 5B, FIG. 5C, FIG. 5D, and FIG. 5E) and a total of five to eight mice per group (FIG. 5H, and FIG. 5I). Bars represent mean±SEM.

Figure 6A:
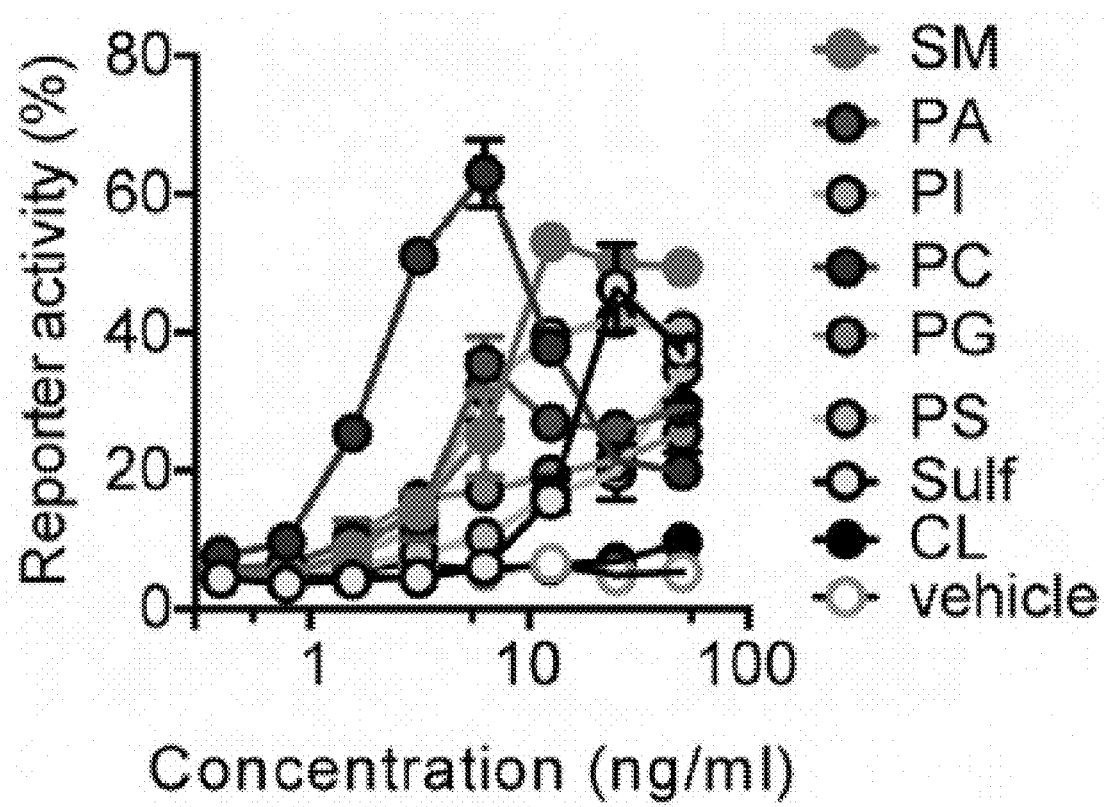
Figure 6B:
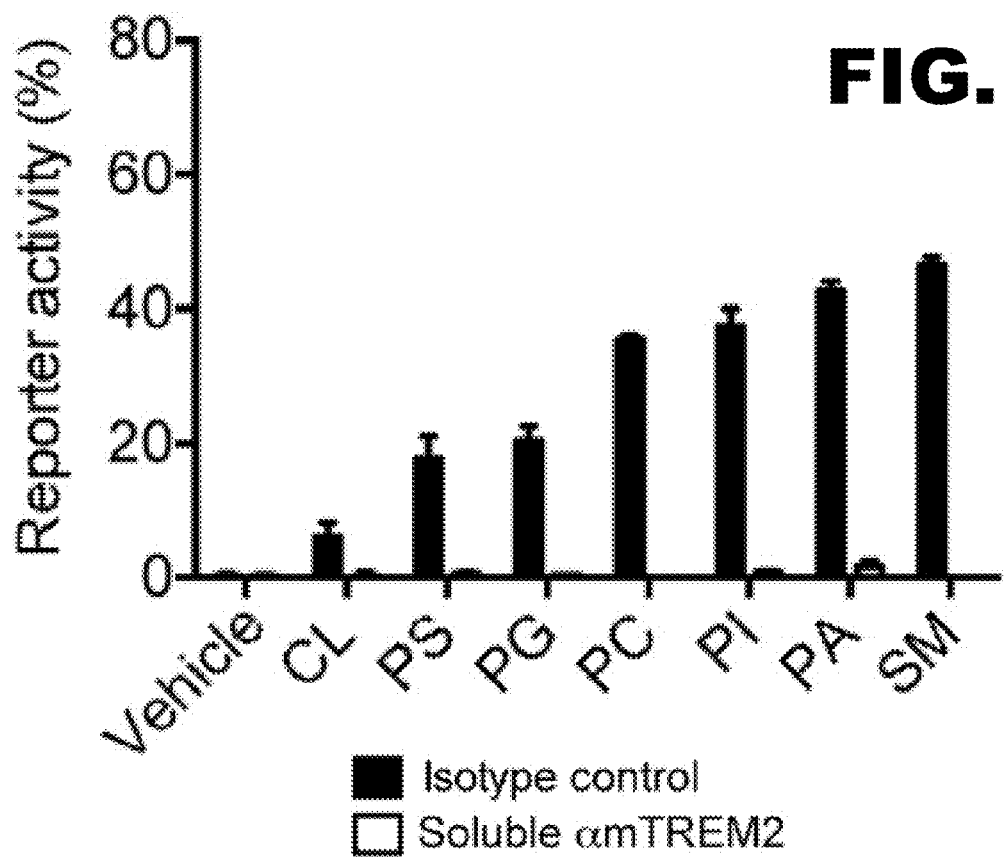

FIG. 6A, FIG. 6B, FIG. 6C, FIG. 6D, and FIG. 6E depict graphs showing TREM2 is a receptor for lipid patterns associated with Aβ. (FIG. 6A, and FIG. 6B) Human TREM2 reporter cells were stimulated with various phospholipids and anionic and zwitterionic lipids at the indicated concentrations. Reporter activation (GFP expression) was assessed after overnight incubation by flow cytometry. TREM2 reporter cells responding to lipids at various concentrations are shown in (FIG. 6A). Blockade of reporter activation by a soluble anti-hTREM2 mAb is shown in (FIG. 6B). SM, sphingomyelin; PA, phosphatidic acid; PI, phosphatidylinositol; PC, phosphatidylcholine; PG, phosphatidylglycerol; PS, phosphatidylserine; Sulf, sulfatide; CL, cardiolipin. (FIG. 6C) mTREM2 reporter cells were cultured with either apoptotic cells (AC) or phosphatidylserine (PS) in the presence of soluble anti-TREM2 mAb or isotype control. (FIG. 6D, and FIG. 6E) Adult primary microglia from Trem2$^{-/-}$5×FAD and 5×FAD mice were pulsed with CSFE-labeled AC. (FIG. 6D) Phagocytosis of AC was determined 20, 40, and 60 min post co-culturing by flow cytometry. (FIG. 6E) Summary of AC uptake by WT and Trem2$^{-/-}$ microglia. Data represent a total of three (FIG. 6A, FIG. 6B, and FIG. 6C) and two (FIG. 6D, and FIG. 6E) independent experiments.

Figure 7A:
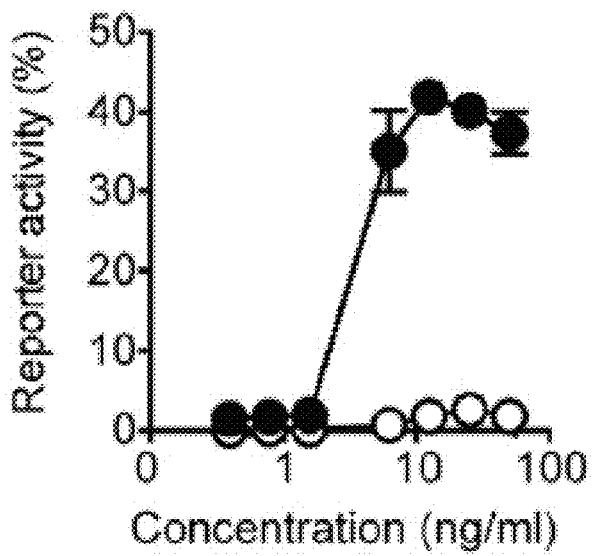
Figure 7B:
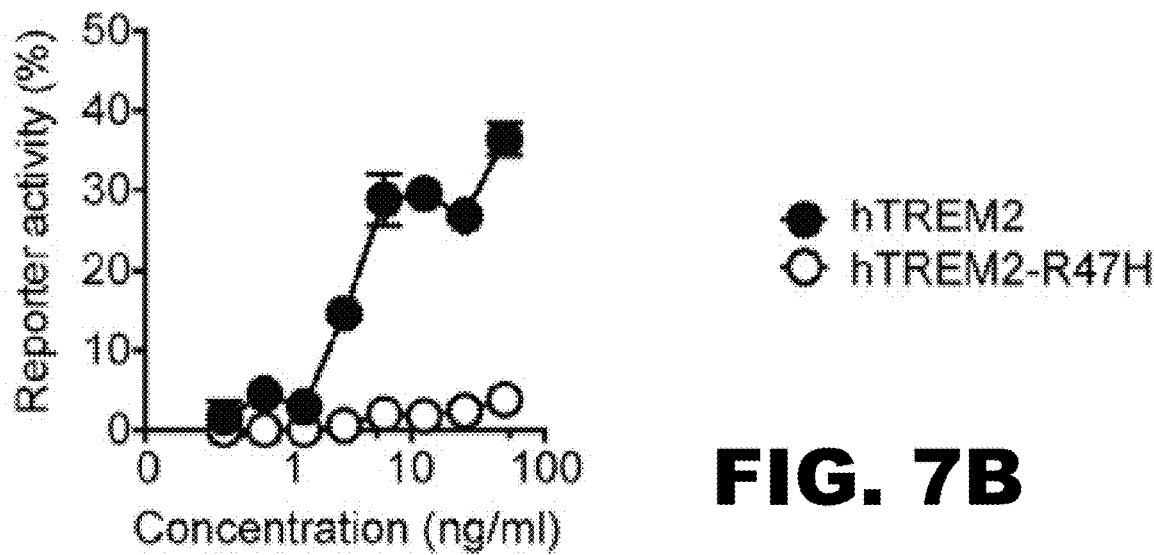
Figure 7C:
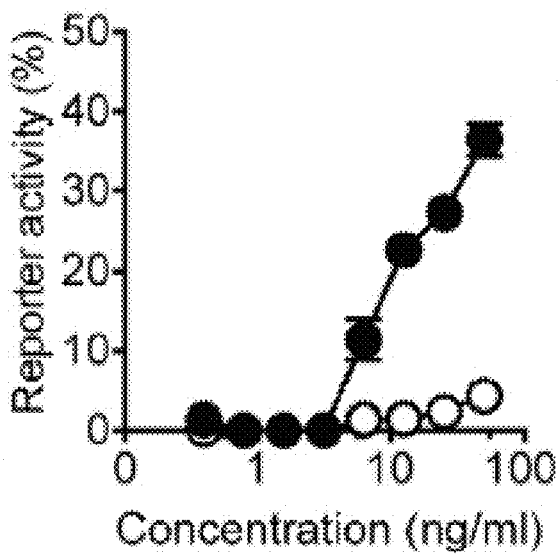
Figure 7D:
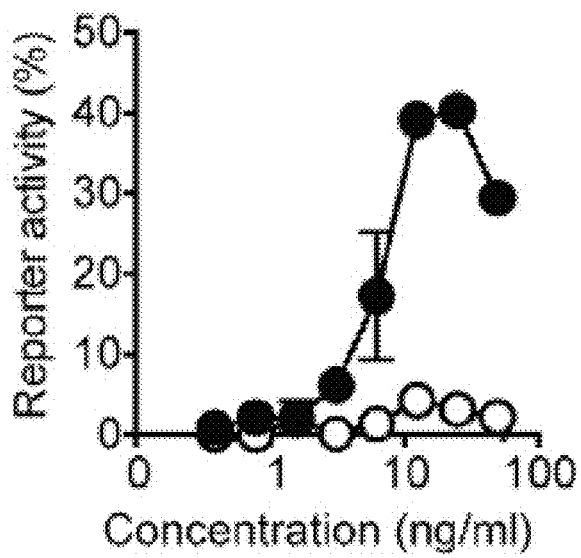
Figure 7E:
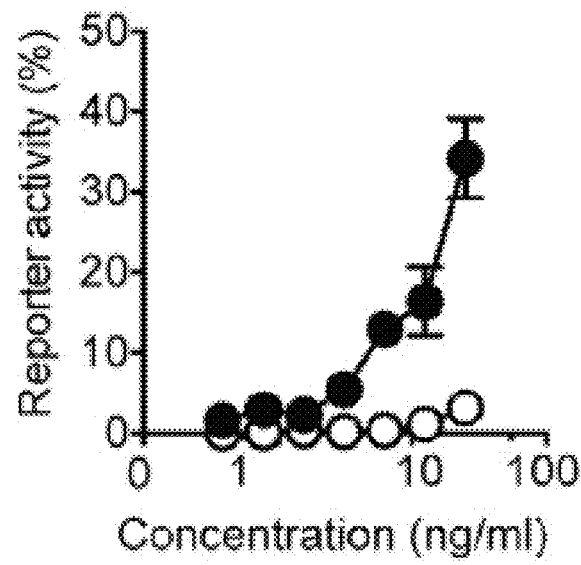
Figure 7F:
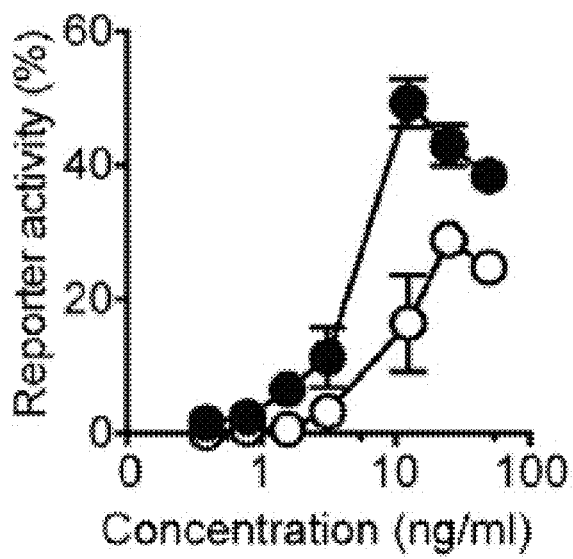
Figure 7G:
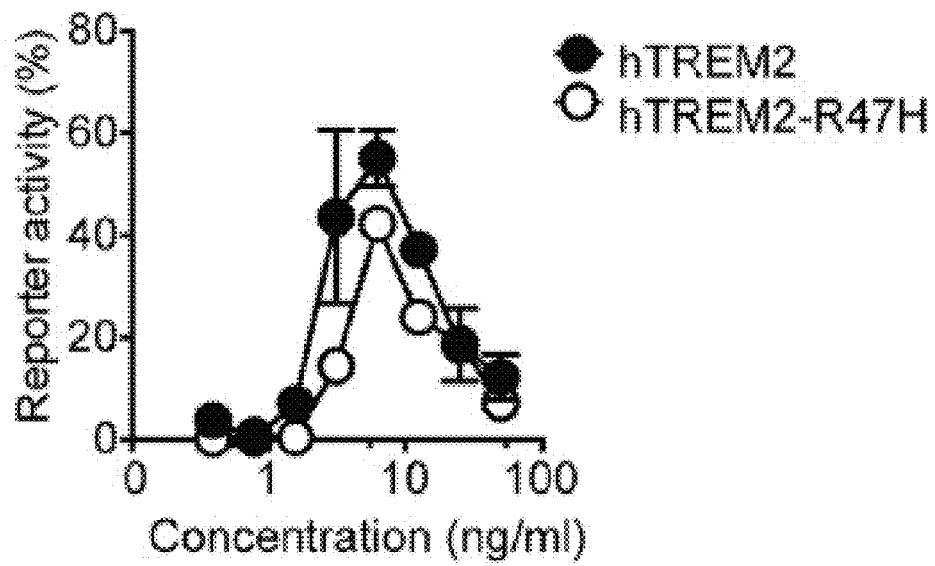
Figure 7H:
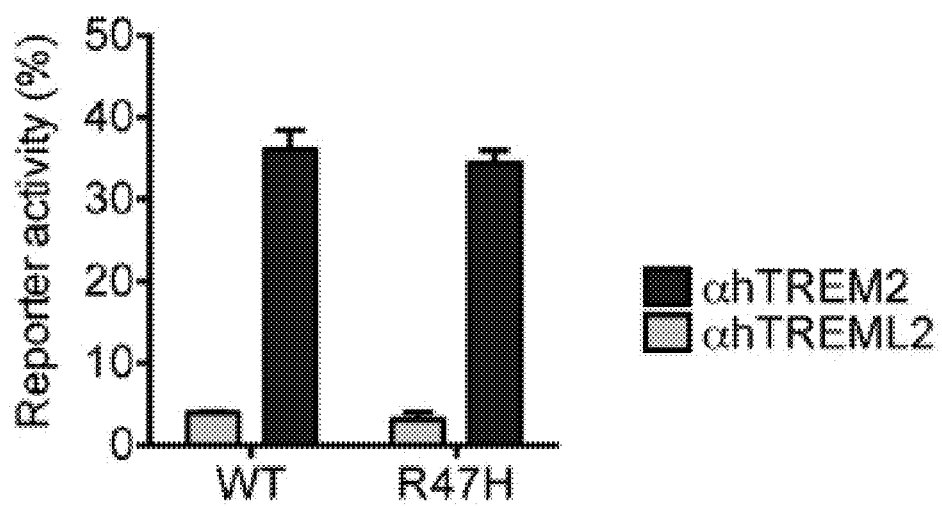

FIG. 7A, FIG. 7B, FIG. 7C, FIG. 7D, FIG. 7E, FIG. 7F, FIG. 7G, and FIG. 7H depicts graphs showing R47H mutation attenuates TREM2 recognition of lipids. Reporter cells expressing either common allele or R47H variant of human TREM2 were stimulated with various species of lipids or plate-bound anti-hTREM2 mAb. A plate-bound control antibody (anti-hTREML2) was used as a negative control. Data represent a total of two independent experiments. Bars represent mean±SEM. (FIG. 7A) phosphatidic acid (PA); (FIG. 7B) phosphatidylglycerol (PG); (FIG. 7C) phosphatidyserine (PS); (FIG. 7D) phosphatidylinositol (PI); (FIG. 7E) sulfatides (FIG. 7F) sphingomyelin (SM); and (FIG. 7G) phosphatidylcholine (PC). FIG. 7H shows stimulating the R47H reporter cells with a plate-bound anti-TREM2 antibody.

FIG. 8A, FIG. 8B, FIG. 8C, and FIG. 8D depict Trem2 deficiency does not affect a burden in cortices of 5×FAD mice. Aβ accumulation in the cortices of 8.5 month-old Trem2$^{-/-}$ 5×FAD and Trem2$^{+/-}$ 5×FAD and 5×FAD mice. (FIG. 8A) Matching coronal sections were stained with an Aβ-specific antibody mHJ3.4. Amounts of Aβ loads in cortices are summarized. (FIG. 8B, FIG. 8C, and FIG. 8D) Soluble and insoluble Aβ$_{1-40}$ and Aβ$_{1-42}$ levels in cortices were detected by ELISA. Data represent analyses total of 8 5×FAD mice, 12 Trem2$^{+/-}$ 5×FAD mice, and 16 Trem2$^{-/-}$ 5×FAD mice. Bars represent mean±SEM. (FIG. 8B) PBS fraction; (FIG. 8C) Triton-X fraction; and (FIG. 8D) Guanidine fraction.

FIG. 9A, FIG. 9B, FIG. 9C, FIG. 9D, FIG. 9E, FIG. 9F, FIG. 9G, FIG. 9H, FIG. 9I, FIG. 9J, FIG. 9K, and FIG. 9L depict flow cytometry plots and graphs showing microglia isolation and gene expression analyses. (FIG. 9A) Flowchart of microglia purification and RNA extraction procedure. (FIG. 9B) qPCR analysis of Trem2 mRNA expression in microglia isolated from age matched 5×FAD, Trem2$^{-/-}$ and WT mice. (FIG. 9C, FIG. 9D, FIG. 9E, FIG. 9F, FIG. 9G, and FIG. 9H) Validation of several microglia activation markers implicated in microarray analysis by flow cytometry. (FIG. 9I, FIG. 9J, FIG. 9K, and FIG. 9L) Expression of several inflammatory cytokines in brains of Trem2$^{-/-}$ 5×FAD, 5×FAD, Trem2$^{-/-}$ and WT mice. (FIG. 9I) Il1b; (FIG. 9J) Tnf; (FIG. 9K) Il12b; and (FIG. 9L) Spp1. *p<0.05, p<0.01, *p<0.001, ****p<0.0001, one-way ANOVA (FIG. 9B), Student's t test (FIG. 9D, FIG. 9E, FIG. 9G, and FIG. 9H), two-way ANOVA (FIG. 9I, FIG. 9J, FIG. 9K, and FIG. 9L). Data represent analyses total of 3-7 mice per group. Bars represent mean±SEM.

Figure 10A:
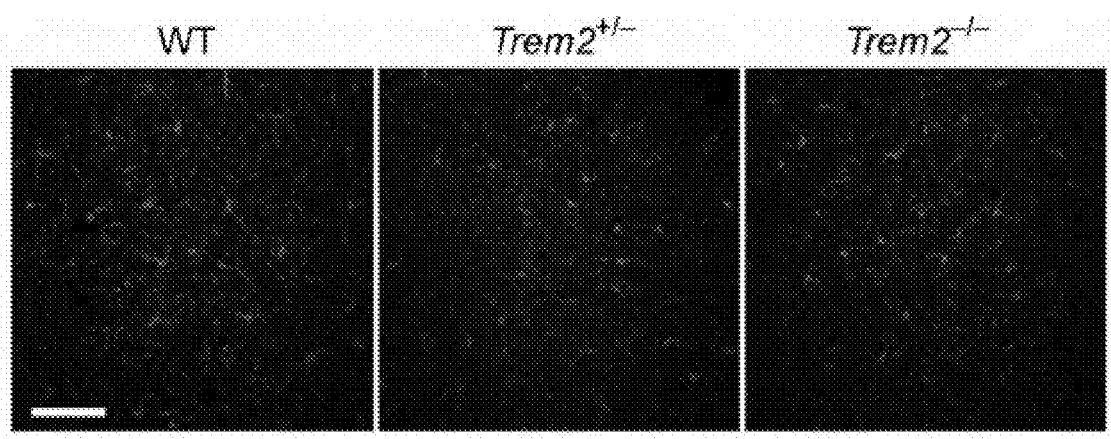
Figure 10B:
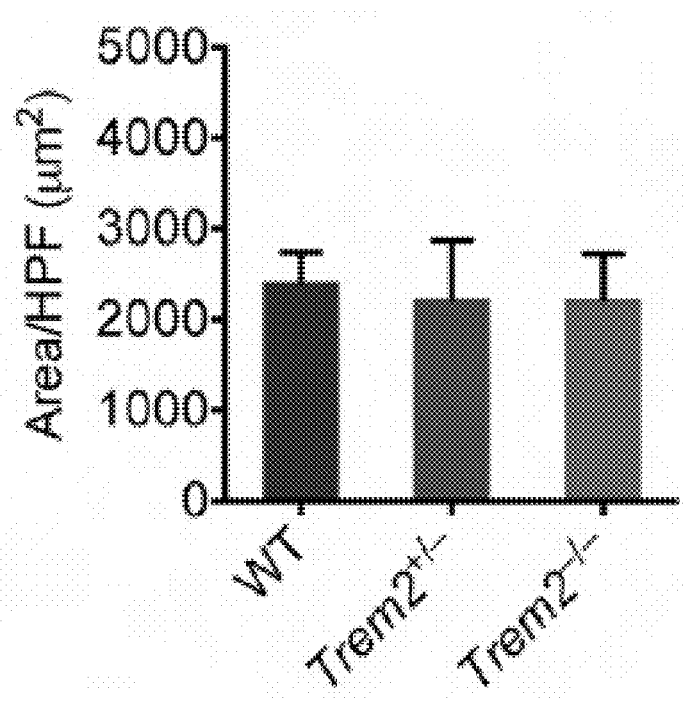
Figure 10C:
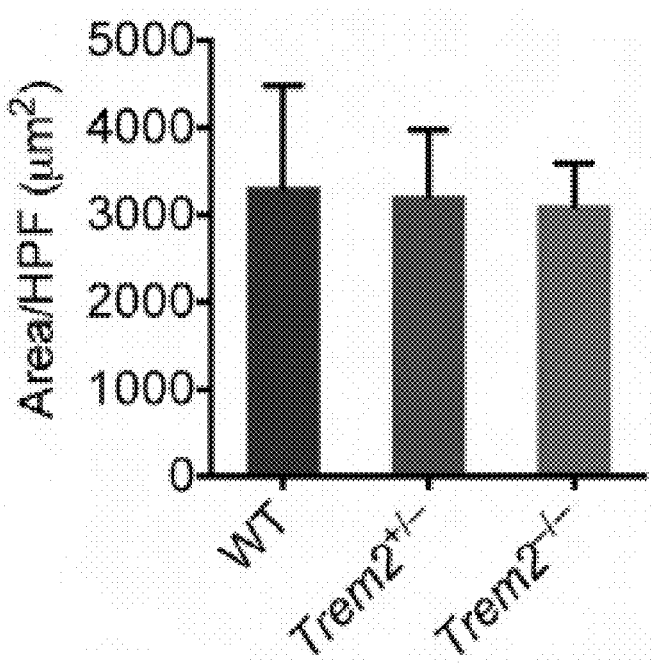
Figure 10D:
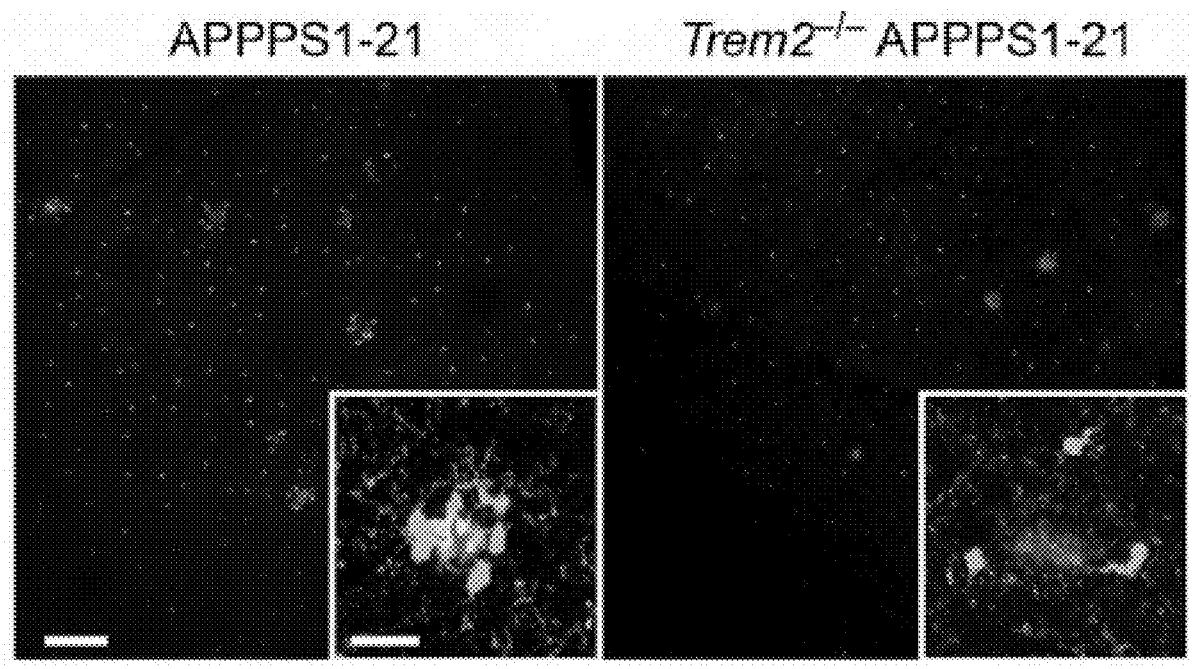
Figure 10E:
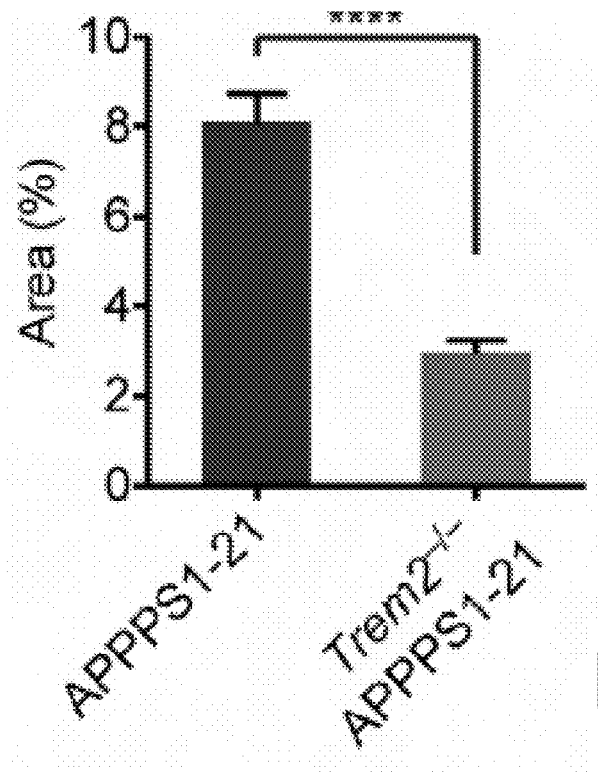
Figure 10F:
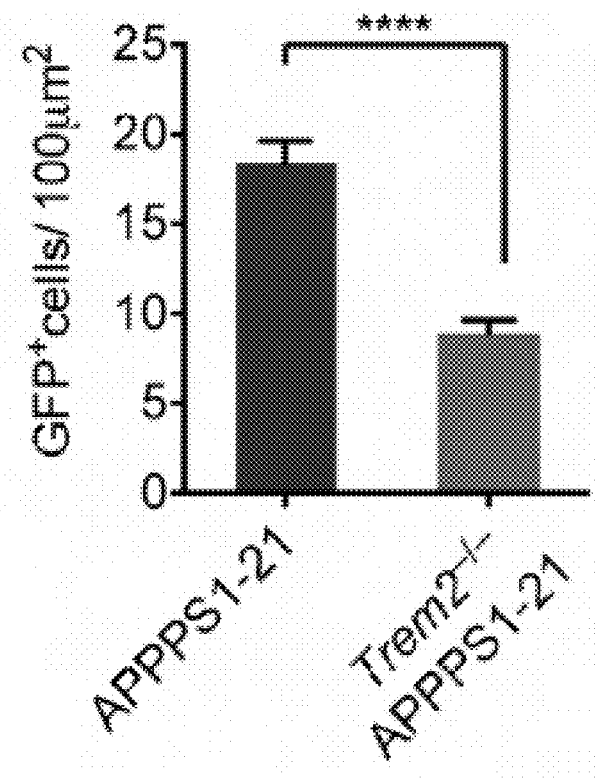

FIG. 10A, FIG. 10B, FIG. 10C, FIG. 10D, FIG. 10E, and FIG. 10F, depict images and graphs showing microglia distribution in steady state and in Cx3cr1$^{+/GFP}$ APPPS1-21 mice. (FIG. 10A, FIG. 10B, and FIG. 10C) Matching coronal sections from 8.5 month old WT, Trem2$^{+/-}$ and Trem2$^{-/-}$ mice were stained with Iba-1 (red). (FIG. 10A) Representative Z-stack images with maximum projection. (FIG. 10B, and FIG. 10C) Quantification of total Iba-1 reactivity per HPF in hippocampi (FIG. 10B) and cortices (FIG. 10C). (FIG. 10D, FIG. 10E, and FIG. 10F) Microgliosis in 3 month old Cx3cr1$^{+/GFP}$ APPPS1-21 mice and Trem2$^{-/-}$ littermates. Microglia were identified as GFP cells (green) and plaques were stained with X-34 (red). (FIG. 10D) Representative Z-stack images with maximum projection. (FIG. 10F) Quantification of plaque-associated microglia expressed as percentage of GFP area or numbers of GFP cells per 100 μm$^2$. ****p<0.0001, Student's t-test. Original magnification 20× (FIG. 10A), 10× (FIG. 10D); Scale bar, 10 μm (FIG. 10A), 100 μm (FIG. 10D), main images, and 20 μm (FIG. 10D), insets. Data represent analyses total of 3-4 mice per group (FIG. 10A, FIG. 10B, and FIG. 10C) and 7-9 mice per group (FIG. 10D, FIG. 10E, and FIG. 10F). Bars represent mean±SEM.

FIG. 11A, FIG. 11B, FIG. 11C, and FIG. 11D depicts graphs showing analyses of plaque-associated and non-plaque-associated microglia. (FIG. 11A) Numbers of non-plaque-associated microglia per HPF in Trem2$^{-/-}$ 5×FAD, Trem2$^{+/-}$ 5×FAD and 5×FAD mice. (FIG. 11B, FIG. 11C, and FIG. 11D) Distribution of plaque-associated microglia in (FIG. 11D) Trem2$^{-/-}$ 5×FAD, (FIG. 11C) Trem2$^{+/-}$ 5×FAD and (FIG. 11B) 5×FAD mice (bar graphs) is compared to Monte Carlo simulations (Gaussian curves in gray). Data represent analyses total of 7-8 mice per group. Bars represent mean±SEM.

Figure 12A:
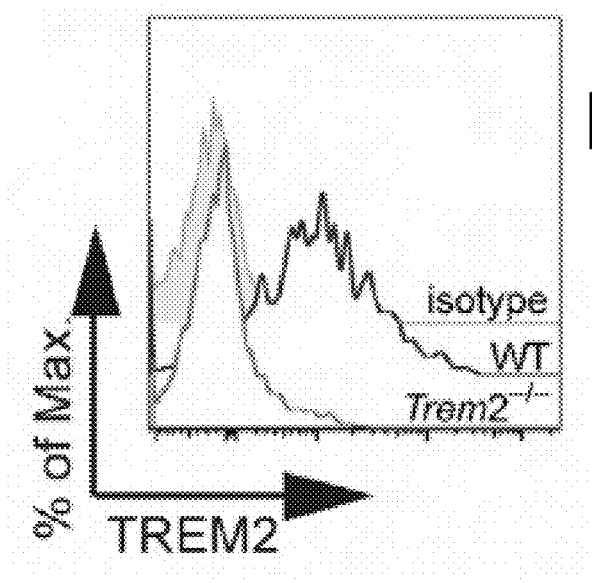
Figure 12B:
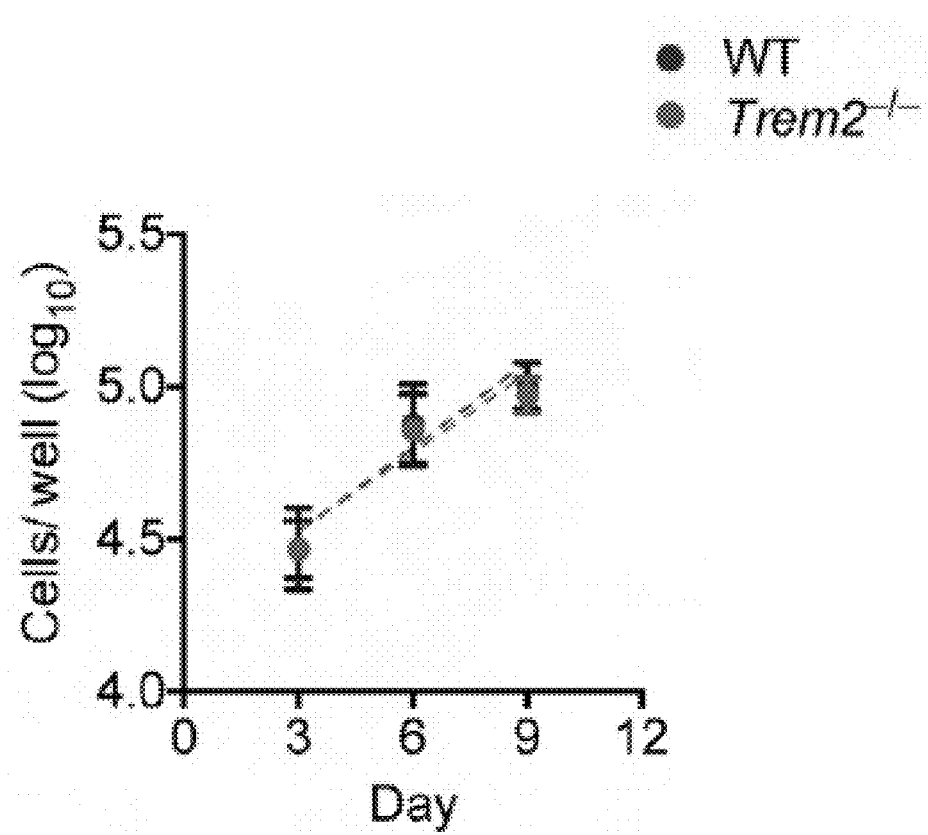
Figure 12C:
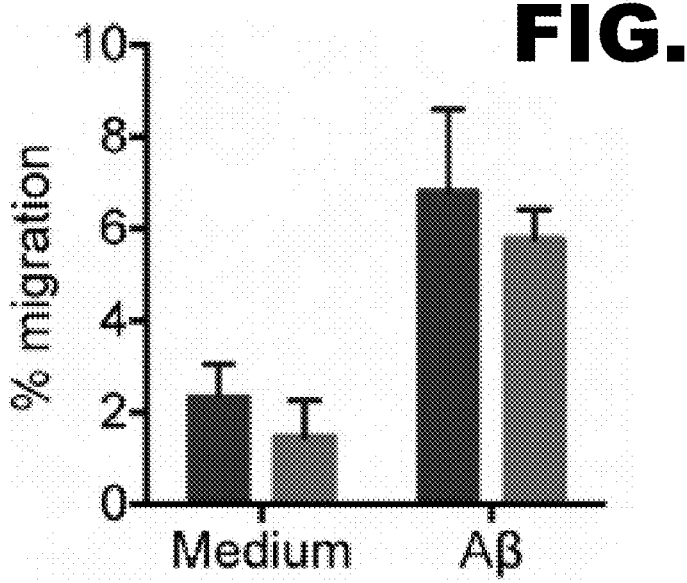
Figure 12D:
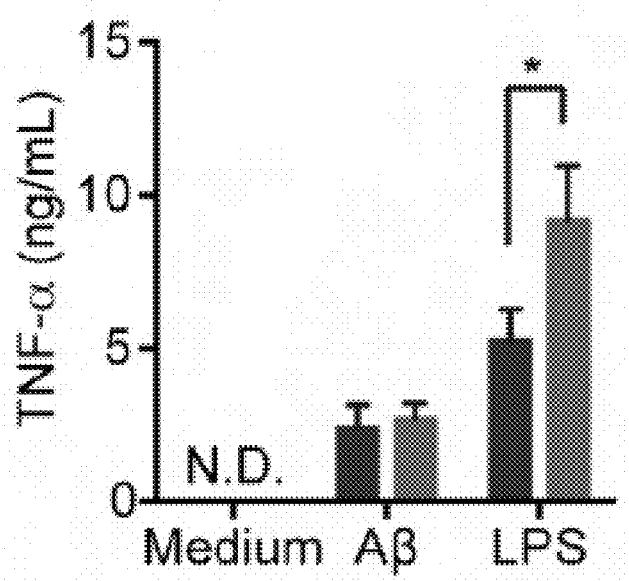
Figure 12E:
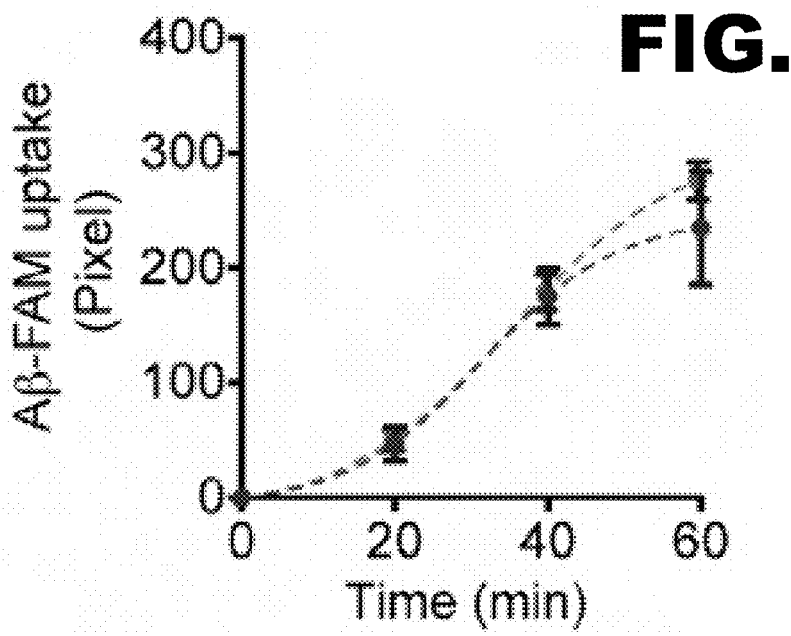
Figure 12F:
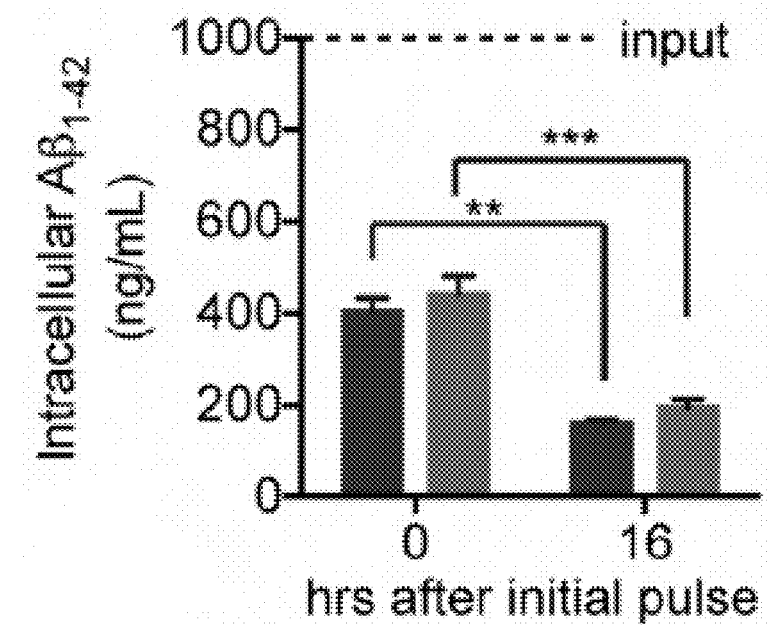

FIG. 12A, FIG. 12B, FIG. 12C, FIG. 12D, FIG. 10E, and FIG. 10F depicts graphs showing Trem2 is not directly involved in Aβ-mediated microglia responses ex vivo. (FIG. 12A) TREM2 surface expression by adult primary microglia. (FIG. 12B) Ex vivo expansion of purified adult microglia in 15% LCM. (FIG. 12C) Migration of WT and Trem2$^{-/-}$ microglia toward fibrillar Aβ in a transwell assay. (FIG. 12D) TNF-α production by WT and Trem2$^{-/-}$ microglia in response to Aβ$_{1-42}$ (1 μg/ml) or LPS (10 ng/ml). N.D.=not detectable. (FIG. 12E) Uptake of FAM-labeled Aβ$_{1-42}$ aggregates by WT and Trem2$^{-/-}$ microglia at different time points. (FIG. 12F) Intracellular Aβ$_{1-42}$ concentration in WT and Trem2$^{-/-}$ microglia at 0 h and 16 h, after 8 h pulsing with soluble Aβ$_{1-42}$ (1 μg/ml). *p<0.05, p<0.01, *p<0.001, Student's t test (FIG. 12D), two-way ANOVA (FIG. 12F). Data represent a summary of two independent experiments. Bars represent mean±SEM.

Figure 13:
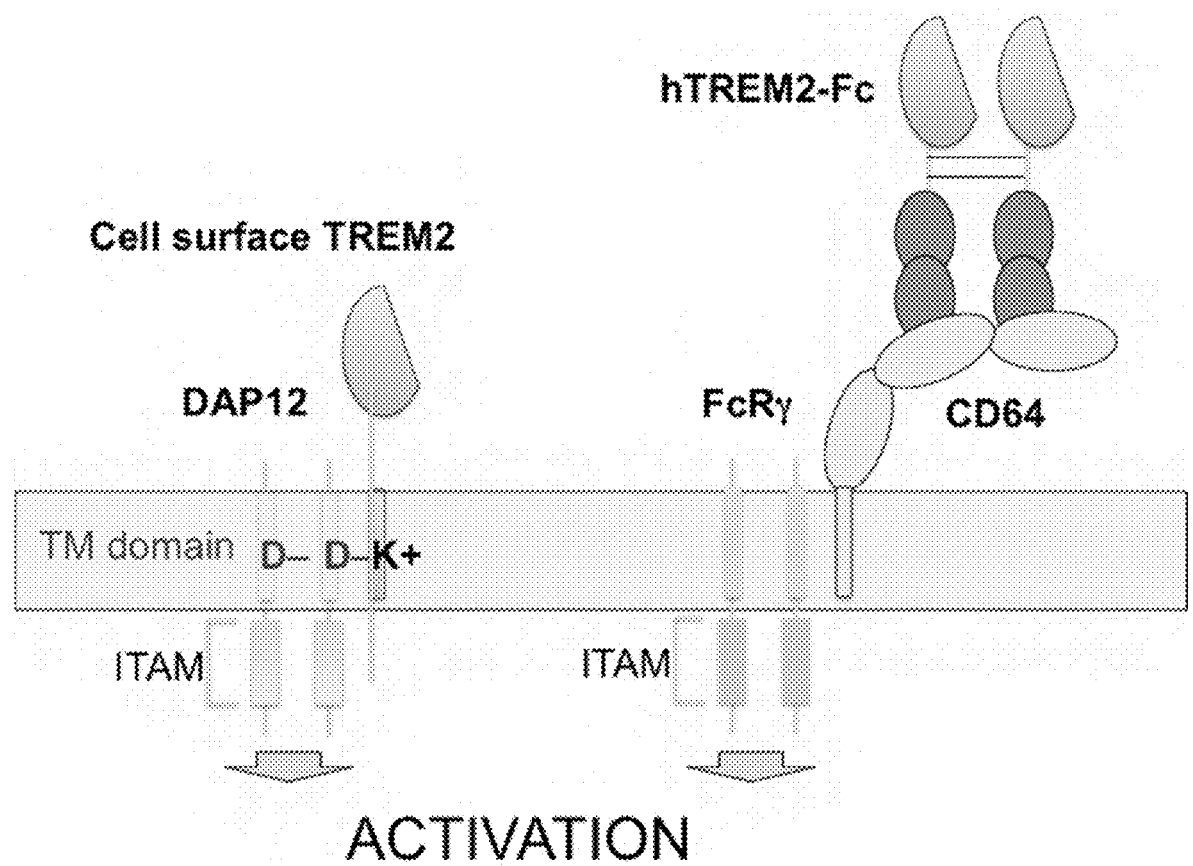

FIG. 13 depicts a schematic of an hTREM2-Fc soluble molecule. The chimeric soluble molecule consists of hTREM2 extracellular region and the Fc fragment of IgG (hTREM2-Fc). Ligand recognition by TREM2 ectodomain leads to aggregation of the hTREM2-Fc/CD64 complex on microglia and the transmission of intracellular signals by CD64 through the associated Fc receptor gamma-chain (FcRγ), which triggers intracellular signals similar to those induced by DAP12.

Figure 14:
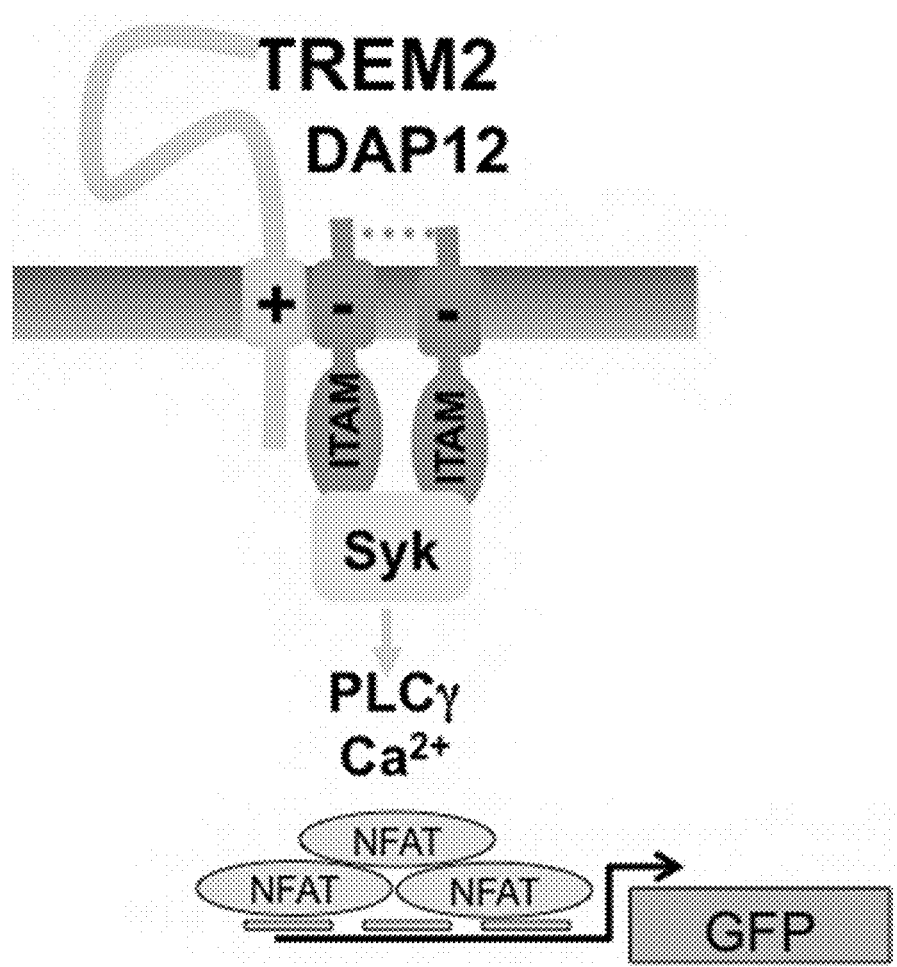

FIG. 14 depicts a schematic showing the design of hTREM2 reporter cells. The reporter cells expressing the arginine 47 to histidine mutation (R47H) of human TREM2 (hTREM2) may be used to identify potent agonists that correct the impaired function of mutated hTREM2. hTREM2 transfected reporter cells express GFP under the control of NFAT, such that when hTREM2 is engaged by a ligand, it will induce Ca2+ mobilization that turns on GFP expression.

DETAILED DESCRIPTION OF THE INVENTION

The present invention provides TREM2 constructs. TREM2 constructs of the invention are polynucleotide sequences encoding a polypeptide, wherein the polypeptide comprises at least one TREM2 or fragment thereof and a targeting moiety, and optionally comprising a signal peptide and/or a purification moiety. The present invention also provides isolated polypeptides encoded by TREM2 constructs, vectors comprising TREM2 constructs, isolated cells comprising said vectors, and methods of use thereof. Reduction in TREM2 function results in individuals with a higher risk of developing a neurodegenerative disease or disorder. Accordingly, a polypeptide of the invention may be used to overcome the reduction in TREM2 function and restore microglia function thereby preventing, treating or alleviating symptoms associated with a neurodegenerative disease or disorder.

I. TREM2

In an aspect, the present invention provides TREM2 or a fragment thereof. "TREM" or "triggering receptor expressed on myeloid cells" refers to a group of activating receptors which are selectively expressed on different types of myeloid cells, such as mast cells, monocytes, macrophages, dendritic cells (DCs), and neutrophils, and may have a predominant role in immune and inflammatory responses. TREMs are primarily transmembrane glycoproteins with an immunoglobulin (Ig)-type fold in their extracellular domain and, hence, belong to the Ig-superfamily (Ig-SF). These receptors contain a short intracellular domain, but lack docking motifs for signaling mediators and require adapter proteins, such as DAP12, for cell activation. A mature TREM comprises one or more of the following domains: (1) an extracellular domain which contains at least one Ig-SF domain; (2) a transmembrane domain; and (3) a cytoplasmic domain. Accordingly, a fragment thereof may be an extracellular-domain, transmembrane-domain, or cytoplasmic-domain fragment. In an embodiment, a fragment thereof is an extracellular-domain fragment. In a specific embodiment, a fragment thereof is an extracellular-domain fragment set forth in SEQ ID NO:1 (MEPLRLLILLFVTELSGAHNTTVFQGVAGQSLQVSCPYDSM-KHWGRRKAWCRQLGE KGPCQRWSTH-NLWLLSFLRRWNGSTAITDDTLGGTLTITLRNLQP-HDAGLYQCQSLH GSEADTLRKVLVEV-LADPLDHRDAGDLWFPGESESFEDAHVEHSISRAER-HVKEDDG R). In another specific embodiment, a fragment thereof is the Ig domain only as set forth in SEQ ID NO:2

(MEPLRLLILLFVTELSGAHNTTVFQGVAGQSLQVSCPYDSMKHWGRRKA

WCRQLGEKGPCQRVVSTHNLWLLSFLRRWNGSTAITDDTLGGTLTITLRN

LQPHDAGLYQCQSLHGSEADTLRKVLVEVLADP).

Specifically, TREM2 is a microglia surface receptor that triggers intracellular protein tyrosine phosphorylation. TREM2 binds anionic carbohydrates, anionic bacterial products and various phospholipids. TREM2 transmits intracellular signals through the associated transmembrane adapter DAP12, which recruits the protein tyrosine kinase Syk, leading to phosphorylation of many downstream mediators, such as PLC-γ, PI-3K and Vav2/3. TREM2 may be encoded by the TREM2 gene from *Homo sapiens* or a homologue thereof (GenBank accession number NM_018965.3 or NM_001271821.1). In a specific embodiment, TREM2 may be encoded by the nucleotide sequence comprising SEQ ID NO:3 (CCTTGGCTGG GGAAGGGTGG CATGGAGCCT CTCCGGCTGC TCATCTTACT CTTTGTCACA GAGCTGTCCG GAGCCCACAA CACCACAGTG TTCCAGGGCG TGGCGGGCCA GTCCCTGCAG GTGTCTTGCC CCTATGACTC CATGAAGCAC TGGGGGAGGC GCAAGGCCTG GTGCCGCCAG CTGGGAGAGA AGGGCCCATG CCAGCGTGTG GTCAGCACGC ACAACTTGTG GCTGCTGTCC TTCCTGAGGA GGTGGAATGG GAGCACAGCC ATCACAGACG ATACCCTGGG TGGCACTCTC ACCATTACGC TGCGGAATCT ACAACCCCAT GATGCGGGTC TCTACCAGTG CCAGAGCCTC CATGGCAGTG AGGCTGACAC CCTCAGGAAG GTCCTGGTGG AGGTGCTGGC AGACCCCCTG GATCACCGGG ATGCTGGAGA TCTCTGGTTC CCCGGGGAGT CTGAGAGCTT CGAGGATGCC CATGTGGAGC ACAGCATCTC CAGGCCATCT CAAGGCTCCC ATCTGCCTTC TTGTCTCTCC AAGGAGCCTC TTGGAAGGAG AAATCCCCTT CCCACCCACT TCCATCCTTC TCCTCCTGGC CTGCATCTTT CTCATCAAGA TTCTAGCAGC CAGCGCCCTC TGGGCTGCAG CCTGGCATGG ACAGAAGCCA GGGACACATC CACCCAGTGA ACTGGACTGT GGCCATGACC CAGGGTATCA GCTCCAAACT CTGCCAGGGC TGAGAGACAC GTGAAGGAAG ATGATGGGAG GAAAAGCCCA GGAGAAGTCC CACCAGGGAC CAGCCCAGCC TGCATACTTG CCACTTGGCC ACCAGGACTC CTTGTTCTGC TCTGGCAAGA GACTACTCTG CCTGAACACT GCTTCTCCTG GACCCTGGAA GCAGGGACTG GTT-GAGGGAG TGGGGAGGTG GTAAGAACAC CTGACAACTT CTGAATATTG GACATTTTAA ACACTTACAA ATAAATCCAA GACTGTCATA TTTAGCTGGA TA).

The present invention also contemplates a homologue, a variant, a derivative, or a fragment of TREM2. A skilled artisan will appreciate that TREM2 can be found in a variety of species. Non-limiting examples include mouse (NM_001272078.1, NM_031254.3), cattle (NM_001079580.2, XM_010818172.1, XM_010818171.1), rat (NM_001106884.1, XM_006244425.2, XM_006244424.2), chicken (NM_001037832.1), cat (XM_003986128.3), chimpanzee (XM_009451226.1, XM_001174108.3, XM_001174118.3), gorilla (XM_004043984.1, XM_004043983.1, XM_004043982.1), horse (XM_005603891.1, XM_005603890.1), hamster (XM_007639783.1, XM_003511765.1), zebrafish (XM_009299847.1), dog (XM_005627313.1), and rabbit (XM_008262906.1). Methods of determining a protein sequence from a nucleic acid sequence are known in the art. In a specific embodiment, TREM2 may comprise SEQ ID NO:4 (MEPLRLLILL FVTELSGAHN TTVFQGVAGQ SLQVSCPYDS MKHWGRRKAW CRQLGEKGPC QRVVSTHNLW LLSFLRRWNG STAITDDTLG GTLTITLRNL QPHDAGLYQC QSLHGSEADT LRKVLVEVLA DPLDHRDAGD LWFPGESESF EDAHVEHSIS RPSQGSHLPS CLSKEPLGRR NPLPTHFHPS PPGLHLSHQD SSSQRPLGCS LAWTEARDTS TQ).

It is appreciated that the present invention is directed to homologues, variants, derivatives, or fragments of TREM2 in other organisms and is not limited to human TREM2 (hTREM2). Homologues, variants, derivatives, or fragments can be found in other species by methods known in the art. In determining whether TREM2 has significant homology or shares a certain percentage of sequence identity with a sequence of the invention, sequence similarity may be determined by conventional algorithms, which typically allow introduction of a small number of gaps in order to achieve the best fit. In particular, "percent identity" of two polypeptides or two nucleic acid sequences is determined using the algorithm of Karlin and Altschul (Proc. Natl. Acad. Sci. USA 87:2264-2268, 1993). Such an algorithm is incorporated into the BLASTN and BLASTX programs of Altschul et al. (J. Mol. Biol. 215:403-410, 1990). BLAST nucleotide searches may be performed with the BLASTN program to obtain nucleotide sequences homologous to a nucleic acid molecule of the invention. Equally, BLAST protein searches may be performed with the BLASTX program to obtain amino acid sequences that are homologous to a polypeptide of the invention. To obtain gapped alignments for comparison purposes, Gapped BLAST is utilized as described in Altschul et al. (Nucleic Acids Res. 25:3389-3402, 1997). When utilizing BLAST and Gapped BLAST programs, the default parameters of the respective programs (e.g., BLASTX and BLASTN) are employed. See www.ncbi.nlm.nih.gov for more details.

A homologue, variant, derivative, or fragment of TREM2 may be at least 80, 85, 90, or 95% homologous to human TREM2 (SEQ ID NO:4). In one embodiment, a homologue, variant, derivative, or fragment of TREM2 may be at least 80, 81, 82, 83, 84, 85, 86, 87, 88, or 89% homologous to human TREM2 (SEQ ID NO:4). In another embodiment, a homologue, variant, derivative, or fragment of TREM2 may be at least 90, 91, 92, 93, 94, 95, 96, 97, 98, 99, or 100% homologous to TREM2 (SEQ ID NO:4).

In certain embodiments, a homologue, variant or derivative of TREM2 may be at least 80, 85, 90, or 95% homologous to human TREM2 extracellular-domain fragment (SEQ ID NO:1). In one embodiment, a homologue, variant or derivative of TREM2 may be at least 80, 81, 82, 83, 84, 85, 86, 87, 88, or 89% homologous to human TREM2 extracellular-domain fragment (SEQ ID NO: 1). In another embodiment, a homologue, variant, or derivative of TREM2 may be at least 90, 91, 92, 93, 94, 95, 96, 97, 98, 99, or 100% homologous to human TREM2 extracellular-domain fragment (SEQ ID NO:1).

In certain embodiments, a homologue, variant or derivative of TREM2 may be at least 80, 85, 90, or 95% homologous to human TREM2 Ig domain only fragment (SEQ ID NO:2). In one embodiment, a homologue, variant or derivative of TREM2 may be at least 80, 81, 82, 83, 84, 85, 86, 87, 88, or 89% homologous to human TREM2 Ig domain only fragment (SEQ ID NO:2). In another embodiment, a homologue, variant, or derivative of TREM2 may be at least 90, 91, 92, 93, 94, 95, 96, 97, 98, 99, or 100% homologous to human TREM2 Ig domain only fragment (SEQ ID NO:2).

II. Targeting Moiety

In an aspect, the present invention provides a targeting moiety. A "targeting moiety" refers to a polypeptide that is able to direct the entity to which it is attached (e.g., TREM2 or a fragment thereof) to a target site. Target sites may include, but are not limited to, the cell surface and a cell-surface protein. In one embodiment, a targeting moiety may comprise a binding domain derived from a target receptor ligand. A target receptor ligand is a ligand that binds a target receptor. Suitable target receptors include cell-surface receptors found on microglia cells. Non-limiting examples of suitable target receptors include the Fc receptors: FcRγ, FcRα, FcRε, and FcRμ FcRγ belongs to the immunoglobulin superfamily and includes several members, FcRγI (CD64), FcRγIIA (CD32), FcRγIIB (CD32), FcRγIIIA (CD16a), and FcRγIIIB (CD16b). In a specific embodiment, the target receptor is FcRγI (CD64). Fc receptors are cell-surface receptors that recognize the Fc region of an antibody. Non-limiting examples of target receptor ligands for an Fc receptor are IgG, IgA, IgE and IgM Fc regions. In a specific embodiment, the target receptor ligand is an IgG Fc region. In another embodiment, a targeting moiety may comprise an antibody capable of specifically binding to an antigenic determinant on a target site, or a fragment thereof that retains specific binding to the antigenic determinant.

In some embodiments, a targeting moiety may be capable of directing the entity to which it is attached to a target receptor on the surface of cell that is capable of expressing TREM2. A cell that is capable of expressing TREM2 may be a microglia, osteoclast, monocyte-derived dendritic cell, bone marrow-derived macrophages and macrophages. In certain embodiments, a targeting moiety may be capable of directing the entity to which it is attached to a target receptor on the surface of a microglia cell. In a specific embodiment, a targeting moiety may be capable of directing the entity to which it is attached to an Fc receptor on the surface of a microglia cell. In another specific embodiment, a targeting moiety may be capable of directing the entity to which it is attached to FcRγI (CD64) on the surface of a microglia cell.

In some embodiments, the targeting moiety may be an antibody or fragment thereof, or a binding domain derived from a target receptor ligand. In certain embodiments, the targeting moiety may be an antibody or fragment thereof. For example, an antibody fragment may be a constant region (e.g. hinge, CH2 and/or CH3 domains). In a specific embodiment, the targeting moiety is an antibody fragment such as an Fc fragment. An Fc fragment comprises the heavy chain constant region of an antibody. Heavy chains are classified as gamma, mu, alpha, delta, or epsilon, and define the antibody's isotype as IgG, IgM, IgA, IgD and IgE, respectively. In a specific embodiment, the Fc fragment is an IgG Fc fragment. There are four IgG subclasses (IgG1, 2, 3, and 4) in humans. Each of the four IgG subclasses may be used as a targeting moiety of the invention. In particular embodiments, the targeting moiety may be a single-chain or linear antibody.

III. TREM2 Construct

In an aspect, the present invention provides a TREM2 construct. A TREM2 construct of the invention is a polynucleotide sequence encoding a polypeptide, wherein the polypeptide comprises at least one TREM2 or fragment thereof and a targeting moiety and optionally comprising a signal peptide and/or a purification moiety. As used herein, the terms "polynucleotide sequence of the invention" and "TREM2 construct" are interchangeable. The present invention also provides isolated polypeptides encoded by TREM2 constructs, vectors comprising TREM2 constructs, and isolated cells comprising said vectors.

(a) Polynucleotide Sequence

A TREM2 construct of the invention is a polynucleotide sequence encoding a polypeptide, wherein the polypeptide comprises at least one TREM2 or fragment thereof and a targeting moiety and optionally comprising a signal peptide and/or a purification moiety. Accordingly, a TREM2 construct of the invention may be a polynucleotide sequence encoding a polypeptide, the polypeptide comprising 1, 2, 3, 4, 5, 6, 7, 8, 9, 10, or more TREM2 or fragments thereof. Alternatively, a TREM2 construct of the invention may be a polynucleotide sequence encoding a polypeptide, the polypeptide comprising 1 to 10 TREM2 or fragments thereof, 1 to 5 TREM2 or fragments thereof, 5 to 10 TREM2 or fragments thereof, 3 to 7 TREM2 or fragments thereof, 1 to 3 TREM2 or fragments thereof, or 3 to 5 TREM2 or fragments thereof. One skilled in the art will appreciate that when two or more TREM2 or fragments thereof are present, each TREM2 or fragment thereof may be the same or different, in any number of combinations.

In some embodiments, a TREM2 construct of the invention is a polynucleotide sequence encoding a polypeptide, wherein the polypeptide comprises at least one TREM2 or fragment thereof and a targeting moiety and optionally comprising a signal peptide and/or a purification moiety, wherein the targeting moiety is capable of directing the at least one TREM2 or fragment thereof to a target receptor on the surface of cell that is capable of expressing TREM2.

In an embodiment, TREM2 or a fragment thereof and a targeting moiety may be arranged such that, after translation, they are connected by a linker stretching between the C-terminus of the TREM2 or fragment thereof to the N-terminus of the targeting moiety, or vice versa. In some embodiments, a TREM2 construct of the invention is a polynucleotide sequence encoding a polypeptide, wherein the polypeptide comprises at least one TREM2 or fragment thereof connected to a targeting moiety via a linker, and optionally comprising a signal peptide and/or a purification moiety, wherein the targeting moiety is capable of directing the TREM2 or fragment thereof to a target receptor on the surface of cell that is capable of expressing TREM2.

In some embodiments, a TREM2 construct of the invention is a polynucleotide sequence encoding a polypeptide, wherein the polypeptide comprises at least one TREM2 or fragment thereof and a targeting moiety, and optionally comprising a signal peptide and/or a purification moiety, wherein the targeting moiety is selected from the group consisting of an antibody or fragment thereof and a binding domain derived from a target receptor ligand, and the targeting moiety is capable of directing the TREM2 or fragment thereof to a target receptor on the surface of a cell that is capable of expressing TREM2.

In some embodiments, a TREM2 construct of the invention is a polynucleotide sequence encoding a polypeptide, wherein the polypeptide comprises at least one TREM2 or fragment thereof connected to a targeting moiety via a linker to, and optionally comprising a signal peptide and/or a purification moiety, wherein the targeting moiety is selected from the group consisting of an antibody or fragment thereof, and a binding domain derived from a target receptor ligand, and the targeting moiety is capable of directing the TREM2 or fragment thereof to a target receptor on the surface of cell that is capable of expressing TREM2.

In some embodiments, a TREM2 construct of the invention is a polynucleotide sequence encoding a polypeptide, wherein the polypeptide comprises at least one TREM2 or fragment thereof and a targeting moiety, and optionally comprising a signal peptide and/or a purification moiety, wherein the targeting moiety is an Fc fragment and the target receptor is CD64.

In some embodiments, a TREM2 construct of the invention is a polynucleotide sequence encoding a polypeptide, wherein the polypeptide comprises at least one TREM2 or fragment thereof connected to a targeting moiety via a linker, and optionally comprising a signal peptide and/or a purification moiety, wherein the targeting moiety is an Fc fragment and the target receptor is CD64.

TREM2 or a fragment thereof and a targeting moiety can be connected via a linker stretching between the C-terminus of the TREM2 or fragment thereof to the N-terminus of the targeting moiety, or vice versa. In each of the above embodiments a "linker" refers to a moiety attaching a TREM2 or fragment thereof and a targeting moiety. Generally speaking, the linker is a peptide. A linker peptide may be from about 1 to about 50 amino acids in length, preferably about 4 to about 25 amino acids in length, or about 4 to about 15 amino acids in length. A linker peptide may be comprised of any suitable combination of amino acids that provides sufficient flexibility and solubility. Preferably, a linker peptide is rich in glycine, as well as serine or threonine.

Each of the above embodiments may optionally comprise a signal peptide and/or a purification moiety. When present, typically the polynucleotide sequence encoding the signal peptide is arranged such that, when expressed, the signal peptide is located at the N-terminus of the TREM2 fusion protein and the polynucleotide sequence encoding the purification moiety is arranged such that, when expressed, the purification moiety is located at the C-terminus of the TREM2 fusion protein. The choice of polynucleotide sequence encoding the signal peptide can and will vary depending on a variety factors including, but not limited to, the desired cellular location and type of cell. Suitable polynucleotide sequences encoding signal peptides are known in the art, as are the polypeptide sequences encoded therefrom. Similarly, the choice of purification moiety can and will vary. Suitable purification moieties are known in the art, as are the polynucleotide sequences encoding them.

In each of the above embodiments, a "TREM2 or fragment thereof" may be as described in detail above in Section I, which is hereby incorporated by reference into this section. Preferably, in each of the above embodiments, the polynucleotide of the invention encodes a polypeptide, wherein the polypeptide comprises at least one extracellular domain of TREM2 selected from the group consisting of SEQ ID NO:1 and SEQ ID NO:2 and an Fc fragment as the targeting moiety.

TREM2 constructs of the invention may be produced from nucleic acids molecules using molecular biological methods known to in the art. Any of the methods known to one skilled in the art for the amplification of polynucleotide fragments and insertion of polynucleotide fragments into a vector may be used to construct the polynucleotide sequences of the invention. These methods may include in vitro recombinant DNA and synthetic techniques and in vivo recombinations (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

(b) Polypeptide Sequence

In another aspect, the present invention provides an isolated polypeptide, wherein the polypeptide comprises at least one TREM2 or fragment thereof attached or linked to a targeting moiety and optionally comprises a signal peptide and/or a purification moiety. This may be referred to as a "TREM2 fusion protein." In one embodiment, a TREM2 fusion protein of the invention may be encoded by a polynucleotide sequence of the invention. Polynucleotide sequences of the invention are described in detail in Section III(a), and are hereby incorporated by reference into this section. It would be appreciated by one of skill in the art that a TREM2 fusion protein may be assembled post-translation, such that a bifunctional linker is used to attach a polypeptide sequence of one or more TREM2 or fragments thereof to a targeting moiety. In these embodiments, it would be possible to have a non-polypeptide targeting moiety, such as an aptamer, or a targeting moiety with non-natural amino acids.

In one embodiment, an isolated polypeptide may comprise at least one TREM2 or fragment thereof attached to a targeting moiety via a linker stretching between the C-terminus of the TREM2 or fragment thereof to the N-terminus of the targeting moiety. In another embodiment, an isolated polypeptide may comprise TREM2 or fragment thereof attached to a targeting moiety via a linker stretching between the C-terminus of the targeting moiety to the N-terminus of the TREM2 or fragment thereof.

Isolated polypeptides of the invention may be produced from nucleic acid molecules using molecular biological methods known to in the art. Generally speaking, a polynucleotide sequence encoding the polypeptide is inserted into a vector that is able to express the polypeptide when introduced into an appropriate host cell. Appropriate host cells include, but are not limited to, bacterial, yeast, insect, and mammalian cells. Once expressed, polypeptides may be obtained from cells of the invention using common purification methods. For example, if the polypeptide has a secretion signal, expressed polypeptides may be isolated from cell culture supernatant. Alternatively, polypeptides lacking a secretion signal may be purified from inclusion bodies and/or cell extract. Polypeptides of the invention may be isolated from culture supernatant, inclusion bodies or cell extract using any methods known to one of skill in the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Isolation of polypeptides is greatly aided when the polypeptide comprises a purification moiety.

(c) Vector

In another aspect, the present invention provides a vector comprising a TREM2 construct of the invention. As used herein, a vector is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, and Rous sarcoma virus vectors.

In a specific embodiment, the vector is an expression vector. The vector may have a high copy number, an intermediate copy number, or a low copy number. The copy number may be utilized to control the expression level for the TREM2 construct, and as a means to control the expression vector's stability. In one embodiment, a high copy number vector may be utilized. A high copy number vector may have at least 31, 35, 40, 45, 50, 55, 60, 65, 70, 75, 80, 85, 90, 95, or 100 copies per bacterial cell. In other embodiments, the high copy number vector may have at least 100, 125, 150, 175, 200, 225, 250, 275, 300, 325, 350, 375, or 400 copies per host cell. In an alternative embodiment, a low copy number vector may be utilized. For example, a low copy number vector may have one or at least two, three, four, five, six, seven, eight, nine, or ten copies per host cell. In another embodiment, an intermediate copy number vector may be used. For instance, an intermediate copy number vector may have at least 10, 11, 12, 13, 14, 15, 16, 17, 18, 19, 20, 21, 22, 23, 24, 25, 26, 27, 28, 29, or 30 copies per host cell.

Expression vectors typically contain one or more of the following elements: promoters, terminators, ribosomal binding sites, and IRES. Promoters that allow expression in all cell types such as the chicken beta actin promoter may be utilized. In addition cell type specific promoters for neurons (e.g. syapsin), astrocytes (e.g. GFAP), oligodendrocytes (e.g. myelin basic protein), or microglia (e.g. Cx3CR1) may be used.

Expression of the nucleic acid molecules of the invention may be regulated by a second nucleic acid sequence so that the molecule is expressed in a host transformed with the recombinant DNA molecule. For example, expression of the nucleic acid molecules of the invention may be controlled by any promoter/enhancer element known in the art.

A nucleic acid encoding a TREM2 construct may also be operably linked to a nucleotide sequence encoding a selectable marker. A selectable marker may be used to efficiently select and identify cells that have integrated the exogenous nucleic acids. Selectable markers give the cell receiving the exogenous nucleic acid a selection advantage, such as resistance towards a certain toxin or antibiotic. Suitable examples of antibiotic resistance markers include, but are not limited to, those coding for proteins that impart resistance to kanamycin, spectomycin, neomycin, gentamycin (G418), ampicillin, tetracycline, chloramphenicol, puromycin, hygromycin, zeocin, and blasticidin.

In some embodiments, the vector may also comprise a transcription cassette for expressing reporter proteins. By way of example, reporter proteins may include a fluorescent protein, luciferase, alkaline phosphatase, beta-galactosidase, beta-lactamase, horseradish peroxidase, and variants thereof.

An expression vector encoding a TREM2 construct may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding aTREM2 construct that is introduced to a cell may be linear or circular, may be single-stranded or double-stranded, and may be DNA, RNA, or any modification or combination thereof.

An expression construct encoding a TREM2 construct may be introduced into a cell by transfection. Methods for transfecting nucleic acids are well known to persons skilled in the art. Transfection methods may include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, or DreamFect.

Upon introduction into a cell, an expression construct encoding a TREM2 construct may be integrated into a chromosome. In some embodiments, integration of the expression construct encoding a TREM2 construct into a cellular chromosome may be achieved with a mobile element. The mobile element may be a transposon or a retroelement. A variety of transposons are suitable for use in the invention. Examples of DNA transposons that may be used include the Mu transposon, the P element transposons from *Drosophila*, and members of the Tc1/Mariner superfamily of transposons such as the sleeping beauty transposon from fish. A variety of retroelements are suitable for use in the invention and include LTR-containing retrotransposons and non-LTR retrotransposons. Non-limiting examples of retrotransposons include Copia and gypsy from *Drosophila melanogaster*, the Ty elements from *Saccharomyces cerevisiae*, the long interspersed elements (LINEs), and the short interspersed elements (SINEs) from eukaryotes. Suitable examples of LINEs include L1 from mammals and R2Bm from silkworm.

Integration of the exogenous nucleic acid into a cellular chromosome may also be mediated by a virus. Viruses that integrate nucleic acids into a chromosome include adeno-associated viruses and retroviruses. Adeno-associated virus (AAV) vectors may be from human or nonhuman primate AAV serotypes and variants thereof. Suitable adeno-associated viruses include AAV type 1, AAV type 2, AAV type 3, AAV type 4, AAV type 5, AAV type 6, AAV type 7, AAV type 8, AAV type 9, AAV type 10, and AAV type 11. A variety of retroviruses are suitable for use in the invention. Retroviral vectors may either be replication-competent or replication-defective. The retroviral vector may be an alpharetrovirus, a betaretrovirus, a gammaretrovirus, a deltaretrovirus, an epsilonretrovirus, a lentivirus, or a spumaretrovirus. In an embodiment, the retroviral vector may be a lentiviral vector. The lentiviral vector may be derived from human, simian, feline, equine, bovine, or lentiviruses that infect other mammalian species. Non-limiting examples of suitable lentiviruses includes human immunodeficiency virus (HIV), simian immunodeficiency virus (SIV), feline immunodeficiency virus (FIV), bovine immunodeficiency virus (BIV), and equine infectious anemia virus (EIAV).

Integration of an expression construct encoding a TREM2 construct into a chromosome of the cell may be random. Alternatively, integration of an expression construct encoding a TREM2 construct may be targeted to a particular sequence or location of a chromosome. In general, the general environment at the site of integration may affect whether the integrated expression construct encoding a TREM2 construct is expressed, as well as its level of expression. The virus may be altered to have tropism for a specific cell type. For example, the virus may be altered to have tropism for microglial cells.

Cells transfected with the expression construct encoding a TREM2 construct generally will be grown under selection to isolate and expand cells in which the nucleic acid has integrated into a chromosome. Cells in which the expression construct encoding a TREM2 construct has been chromosomally integrated may be maintained by continuous selection with the selectable marker as described above. The presence and maintenance of the integrated exogenous nucleic acid sequence may be verified using standard techniques known to persons skilled in the art such as Southern blots, amplification of specific nucleic acid sequences using the polymerase chain reaction (PCR), and/or nucleotide sequencing.

Nucleic acid molecules are inserted into a vector that is able to express the fusion polypeptides when introduced into an appropriate host cell. Appropriate host cells include, but are not limited to, bacterial, yeast, insect, and mammalian cells.

In preferred embodiments, a vector-comprising a TREM2 construct of the invention is an adeno-associated viral (AAV) vector. Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol*, 45: 555-564 (1983) as corrected by Ruffing et al., *J Gen Virol*, 75: 3385-3392 (1994). Cis-acting sequences directing viral DNA replication, encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus, making cold preservation of AAV less critical. AAV may even be lyophilized. Finally, AAV-infected cells are not resistant to superinfection.

Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11. AAV9 is described in U.S. Pat. No. 7,198,951 and in Gao et al., *J. Virol.*, 78: 6381-6388 (2004). Advances in the delivery of AAV6 and AAV8 have made possible the transduction by these serotypes of skeletal and cardiac muscle following simple systemic intravenous or intraperitoneal injections. See, Pacak et al., *Circ. Res.*, 99(4): 3-9 (1006) and Wang et al., *Nature Biotech.*, 23(3): 321-328 (2005). The use of some serotypes of AAV to target cell types within the central nervous system, though, has required surgical intraparenchymal injection. See, Kaplitt et al., *Lancet* 369: 2097-2105 (2007); Marks et al., *Lancet Neurol* 7: 400-408 (2008); and Worgall et al., *Hum Gene Ther* (2008).

An adeno-associated viral (AAV) vector is a plasmid comprising a recombinant AAV genome. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety. In an exemplary embodiment, a vector is based on the AAV2 serotype. In another exemplary embodiment, a vector is based on the AAV9 serotype (see, for example, Foust et al., *Nature Biotechnology*, 27: 59-65 (2009); Duque et al., *Mol. Ther.* 17: 1187-1196 (2009); Zincarelli et. al., *Mol. Ther.*, 16: 1073-1080 (2008); and U.S. Patent Publication No. 20130039888).

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786,211; 5,871,982; and 6,258,595. The foregoing documents are hereby incorporated by reference in their entirety herein, with particular emphasis on those sections of the documents relating to rAAV production.

The invention thus provides packaging cells that produce infectious rAAV. In another aspect, the invention provides rAAV (i.e., infectious encapsidated rAAV particles) comprising a rAAV genome of the invention. In some embodiments of the invention, the rAAV genome is a self-complementary genome.

(d) Isolated Cell

In another aspect, the present invention provides an isolated cell comprising a vector of the invention. The cell may be a prokaryotic cell or a eukaryotic cell. Appropriate cells include, but are not limited to, bacterial, yeast, insect, and mammalian cells.

In some embodiments, the isolated host cell comprising a vector of the invention may be used to produce a polypeptide encoded by a TREM2 construct of the invention. Generally, production of a polypeptide of the invention involves transfecting isolated host cells with a vector comprising a TREM2 construct and then culturing the cells so that they transcribe and translate the desired polypeptide. The isolated host cells may then be lysed to extract the expressed polypeptide for subsequent purification. "Isolated host cells" according to the invention are cells which have been removed from an organism and/or are maintained in vitro in substantially pure cultures. A wide variety of cell types can be used as isolated host cells of the invention, including both prokaryotic and eukaryotic cells. Isolated cells include, without limitation, bacterial cells, fungal cells, yeast cells, insect cells, and mammalian cells.

In one embodiment, the isolated host cell is characterized in that after transformation with a vector of the invention, it produces the desired polypeptide for subsequent purification. Such a system may be used for protein expression and purification as is standard in the art. In some embodiments, the host cell is a prokaryotic cell. Non-limiting examples of suitable prokaryotic cells may include *E. coli* and other Enterobacteriaceae, *Escherichia* sp., *Campylobacter* sp., *Wolinella* sp., *Desulfovibrio* sp. *Vibrio* sp., *Pseudomonas* sp. *Bacillus* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp., *Heliospirillum* sp., *Sporomusa* sp., *Spiroplasma* sp., *Ureaplasma* sp., *Erysipelothrix* sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter* sp, *Stenotrophomonas* sp., *Micrococcus* sp., *Neisseria* sp., *Bdellovibrio* sp., *Hemophilus* sp., *Klebsiella* sp., *Proteus mirabilis*, *Enterobacter cloacae*, *Serratia* sp., *Citrobacter* sp., *Proteus* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., *Kingella* sp., *Pasteurella* sp., *Flavobacterium* sp. *Xanthomonas* sp., *Burkholderia* sp., *Aeromonas* sp., *Plesiomonas* sp., *Legionella* sp. and alpha-proteobaeteria such as *Wolbachia* sp., cyanobacteria, spirochaetes, green sulfur and green non-sulfur bacteria, Gram-negative cocci, Gram negative bacilli which are fastidious, Enterobacteriaceae-glucose-fermenting gram-negative bacilli, Gram negative bacilli-non-glucose fermenters, Gram negative bacilli-glucose fermenting, oxidase positive.

Particularly useful bacterial host cells for protein expression include Gram negative bacteria, such as *Escherichia coli*, *Pseudomonas fluorescens*, *Pseudomonas haloplanctis*, *Pseudomonas putida* AC10, *Pseudomonas pseudoflava*, *Bartonella henselae*, *Pseudomonas syringae*, *Caulobacter crescentus*, *Zymomonas mobilis*, *Rhizobium meliloti*, *Myxococcus xanthus* and Gram positive bacteria such as *Bacillus subtilis*, *Corynebacterium*, *Streptococcus cremoris*, *Streptococcus lividans*, and *Streptomyces lividans*. *E. coli* is one of the most widely used expression hosts. Accordingly, the techniques for overexpression in *E. coli* are well developed and readily available to one of skill in the art. Further, *Pseudomonas fluorescens*, is commonly used for high level production of recombinant proteins (i.e. for the development bio-therapeutics and vaccines).

Particularly useful fungal host cells for protein expression may include *Aspergillis oryzae*, *Aspergillis niger*, *Trichoderma reesei*, *Aspergillus nidulans*, *Fusarium graminearum*.

Particularly useful yeast host cells for protein expression may include *Candida albicans*, *Candida maltose*, *Hansenula polymorpha*, *Kluyveromyces fragilis*, *Kluyveromyces lactis*, *Pichia guillerimondii*, *Pichia pastoris*, *Saccharomyces cerevisiae*, *Schizosaccharomyces pombe*, and *Yarrowia lipolytica*.

Particularly useful mammalian host cells for protein expression may include Chinese hamster ovary (CHO) cells, HeLa cells, baby hamster kidney (BHK) cells, monkey kidney cells (COS), human hepatocellular carcinoma cells (eg. Hep G2), human embryonic kidney cells, *Bos primigenius*, and *Mus musculus*. Additionally, the mammalian host cell may be an established, commercially-available cell line (e.g., American Type Culture Collection (ATCC), Manassas, Va.). The host cell may be an immortalized cell. Alternatively, the host cell may be a primary cell. "Primary cells" are cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

In another embodiment, the host cell may be in vivo; i.e., the cell may be disposed in a subject. Accordingly, a polypeptide of the invention is expressed from a host cell in the subject. In certain embodiments, a host cell in a subject may be selected from the group consisting of neurons, astrocytes, oligodendrocytes, microglia, chroroid plexus cells, brain blood vessel endothelial cells, brain blood vessel smooth muscle cells, and brain blood vessel pericytes. In a specific embodiment, the host cell may be microglial cell. In an exemplary embodiment, an AAV vector may be used to express a polypeptide of the invention in a host cell disposed in a subject.

IV. Methods

In another aspect, the present invention provides a method of delivering a TREM2 construct of the invention to a cell. In some embodiments, the method comprises contacting a cell with a composition comprising a vector, the vector comprising a TREM2 construct of the invention. In other embodiments, the method comprises contacting a cell with a composition comprising a second cell, the second cell comprising a TREM2 construct of the invention. In other embodiments, the method comprises contacting a cell with a composition comprising a rAAV, the rAAV comprising a TREM2 construct of the invention. In preferred embodiments, the TREM2 construct is a polynucleotide sequence encoding a polypeptide comprising a signal peptide, at least one TREM2 or fragment thereof, and a targeting moiety. In a specific embodiment, the TREM2 construct is a polynucleotide sequence encoding a polypeptide comprising a signal peptide, at least one extracellular domain of TREM2 selected from the group consisting of SEQ ID NO:1 and SEQ ID NO:2 and a targeting moiety. Cells are contacted with the composition comprising a vector of the invention under effective conditions for a period of time sufficient to deliver a TREM2 construct to a cell. Suitable cells are described above in Section III, and hereby incorporated by reference into this section. For example, the cell may be a bacterial cell, a yeast cell, an insect cell, or a mammalian cell. The choice of cells can and will vary depending upon the goal. In certain embodiments, the goal may be to obtain an isolated polypeptide of the invention. Cell types for protein production are well known in the art and a suitable cell type can be readily selected by one of skill in the art.

In certain embodiments, the goal may be to deliver a composition comprising a polypeptide of the invention to a subject. Accordingly, the present invention provides a method of delivering or targeting TREM2 to an Fc receptor on a microglial cell in a subject. The method comprises administering to the subject a composition comprising an isolated polypeptide encoded by a TREM2 construct of the invention. In preferred embodiments, the TREM2 construct is a polynucleotide sequence encoding at least one TREM2 or fragment thereof and a targeting moiety. In a specific embodiment, the targeting moiety may be an Fc fragment and the TREM2 fragment may be an extracellular domain.

In another specific embodiment, the extracellular domain may comprise the sequence set forth in SEQ ID NO:1 or SEQ ID NO:2.

In another aspect, the present invention encompasses a method of restoring the function of TREM2 in a subject. In some embodiments, the method comprises administering to a subject a composition comprising an isolated polypeptide encoded by a TREM2 construct of the invention. In a specific embodiment, the isolated polypeptide of the invention comprises the extracellular domain of TREM2 attached to an Fc fragment. The Fc fragment may bind to an Fc receptor on microglia thereby triggering intracellular signals similar to those induced by DAP12. In another specific embodiment, the extracellular domain may comprise the sequence set forth in SEQ ID NO:1 or SEQ ID NO:2.

In still another aspect, the invention provides a method for preventing, in a subject, a disease or condition associated with aberrant expression or activity of TREM2, by administering to the subject a composition comprising an isolated polypeptide of the invention. Subjects with loss-of-function mutations of TREM2 are susceptible to neurodegenerative diseases such as Alzheimer's disease, frontotemporal dementia, Huntington's disease, Parkinson's disease, amyotrophic lateral sclerosis and Nasu-Hakola disease due to defective microglia functions. In a specific embodiment, the loss-of-function mutation of TREM2 may be the arginine 47 to histidine mutation (R47H). Administration of a prophylactic agent can occur prior to the manifestation of symptoms characteristic of the aberrancy, such that a disease or disorder is prevented or delayed in its progression or symptoms of the disease or disorder are prevented or delayed.

In still yet another aspect, the invention provides methods of modulating expression or activity of TREM2 for therapeutic purposes. The method comprises administering to a subject a composition comprising an isolated polypeptide of the invention. In one embodiment, the polypeptide of the invention stimulates one or more of the biological activities of TREM2. As such, the present invention provides methods of treating an individual afflicted with a disease or disorder characterized by aberrant expression or activity of TREM2. The disease may be a neurodegenerative disease such as Alzheimer's disease, frontotemporal dementia, Huntington's disease, Parkinson's disease, amyotrophic lateral sclerosis and Nasu-Hakola disease. Treatment may be measured by a reduction in symptoms associated with the disease.

In the foregoing embodiments, the composition may be administered to the subject orally, parenterally, intraperitoneally, intravascularly, intrapulmonary, or topically. The term parenteral as used herein includes subcutaneous, intravenous, intramuscular, intrathecal, or intrasternal injection, or infusion techniques. In a specific embodiment, the composition reaches the central nervous system (CNS). The composition may further comprise an excipient. Non-limiting examples of excipients include antioxidants, binders, buffers, diluents (fillers), disintegrants, dyes, effervescent disintegration agents, preservatives (antioxidants), flavor-modifying agents, lubricants and glidants, dispersants, coloring agents, pH modifiers, chelating agents, preservatives (e.g., antibacterial agents, antifungal agents), release-controlling polymers, solvents, surfactants, and combinations of any of these agents.

V. Screening Assays

The invention also provides a method for identifying (or screening) modulators, i.e., candidate or test compounds or agents (e.g., peptides, peptidomimetics, small molecules or other drugs) which bind to TREM2 or have a stimulatory or inhibitory effect on, for example, expression or activity of TREM2. In one embodiment, the invention provides assays for screening candidate or test compounds which bind to or modulate the activity of the membrane-bound form of TREM2 or biologically active portion thereof. The test compounds of the present invention can be obtained using any of the numerous approaches in combinatorial library methods known in the art, including: biological libraries, spatially addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, non-peptide oligomer or small molecule libraries of compounds (Lam, 1997, *Anticancer Drug Des.* 12:145).

Examples of methods for the synthesis of molecular libraries can be found in the art, for example in: DeWitt, et al., 1993, *Proc. Natl. Acad. Sci. USA* 90:6909; Erb, et al., 1994, *Proc. Natl. Acad. Sci. USA* 91:11422; Zuckermann et al., 1994, *J. Med. Chem.* 37:2678; Cho, et al., 1993, *Science* 261:1303; Carrell, et al., 1994, *Angew. Chem. Int. Ed. Engl.* 33:2059; Carell, et al., 1994, *Angew. Chem. Int. Ed. Engl.* 33:2061; and Gallop, et al., 1994, *J. Med. Chem.* 37:1233.

Libraries of compounds may be presented in solution (e.g., Houghten, 1992, *Bio/Techniques* 13:412-421), or on beads (Lam, 1991, *Nature* 354:82-84), chips (Fodor, 1993, *Nature* 364:555-556), bacteria (U.S. Pat. No. 5,223,409), spores (U.S. Pat. Nos. 5,571,698; 5,403,484; and 5,223, 409), plasmids (Cull, et al., 1992, *Proc. Natl. Acad. Sci. USA* 89:1865-1869) or phage (Scott and Smith, 1990, *Science* 249:386-390; Devlin, 1990, *Science* 249:404-406; Cwirla, et al., 1990, *Proc. Natl. Acad. Sci. USA* 87:6378-6382; and Felici, 1991, *J. Mol. Biol.* 222:301-310).

In one embodiment, an assay is a cell-based assay in which a cell which expresses a membrane-bound form of TREM2, or a biologically active portion thereof, on the cell surface, is contacted with a test compound and the ability of the test compound to bind to TREM2 is determined. The cell, for example, can be a yeast cell or a cell of mammalian origin. Determining the ability of the test compound to bind to TREM2 may be accomplished, for example, by coupling the test compound with a radioisotope or enzymatic label such that binding of the test compound to TREM2 or biologically active portion thereof can be determined by detecting the labeled compound in a complex. For example, test compounds may be labeled with $^{125}$I $^{35}$S, $^{14}$C, or $^{3}$H, either directly or indirectly, and the radioisotope detected by direct counting of radio emission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In an embodiment, the assay comprises contacting a cell which expresses a membrane-bound form of TREM2, or a biologically active portion thereof, on the cell surface with a known compound which binds the TREM2 to form an assay mixture, contacting the assay mixture with a test compound, and determining the ability of the test compound to interact with TREM2, wherein determining the ability of the test compound to interact with TREM2 comprises determining the ability of the test compound to preferentially bind to TREM2 or a biologically active portion thereof as compared to the known compound.

In another embodiment, an assay is a cell-based assay comprising contacting a cell expressing a membrane-bound form of TREM2, or a biologically active portion thereof, on the cell surface with a test compound and determining the ability of the test compound to modulate (e.g., stimulate or inhibit) the activity of TREM2 or biologically active portion thereof. Determining the ability of the test compound to modulate the activity of TREM2 or a biologically active portion thereof can be accomplished, for example, by determining the ability of TREM2 to bind to or interact with a target molecule.

Determining the ability of TREM2 to bind to or interact with a target molecule can be accomplished by one of the methods described above for determining direct binding. As used herein, a "target molecule" is a molecule with which TREM2 binds or interacts with in nature, for example, a molecule on the surface of a cell which expresses the selected protein, a molecule on the surface of a second cell, a molecule in the extracellular milieu, a molecule associated with the internal surface of a cell membrane or a cytoplasmic molecule. For example, a target molecule can be a component of a signal transduction pathway which facilitates transduction of an extracellular signal (e.g., a signal generated by binding of a compound to TREM2) through the cell membrane and into the cell or a second intercellular protein which has catalytic activity or a protein which facilitates the association of downstream signaling molecules with TREM2. Determining the ability of TREM2 to bind to or interact with a target molecule can be accomplished by determining the activity of the target molecule. For example, the activity of the target molecule may be determined by detecting induction of a cellular second messenger of the target (e.g., intracellular $Ca^{2+}$, protein tyrosine phosphorylation, phospholipase phosphorylation, etc.), detecting catalytic/enzymatic activity of the target on an appropriate substrate, detecting the induction of a reporter gene (e.g., a regulatory element that is responsive to a polypeptide of the invention operably linked to a nucleic acid encoding a detectable marker, such as luciferase or a fluorescent protein), or detecting a cellular response, for example, cellular differentiation, or cell proliferation.

In another embodiment, an assay is a cell-based assay comprising contacting a cell expressing a membrane-bound form of TREM2, or a biologically active portion thereof, on the cell surface with a test compound and determining the ability of the test compound to modulate (e.g., stimulate or inhibit) the activity of TREM2 or biologically active portion thereof. Determining the ability of the test compound to modulate the activity of TREM2 or a biologically active portion thereof can be accomplished, for example, by determining the ability of TREM2 to bind to or interact with a target molecule.

In a specific embodiment, an assay is a cell-based assay comprising contacting a cell expressing a membrane-bound form of TREM2, or a biologically active portion thereof, on the cell surface with a test compound and determining the ability of the test compound to modulate (e.g., stimulate or inhibit) the activity of TREM2 or biologically active portion thereof. Determining the ability of the test compound to modulate the activity of TREM2 or a biologically active portion thereof can be accomplished, for example, by determining the ability of TREM2 to induce PLCγ/$Ca^{2+}$ mobilization which in turn activates expression of a reporter protein. Non-limiting examples of reporter proteins may include a fluorescent protein, luciferase, alkaline phosphatase, beta-galactosidase, beta-lactamase, horseradish peroxidase, and variants thereof. Activation of a reporter protein in response to PLCγ/$Ca^{2+}$ may be accomplished by operably linking the reporter protein to a promoter that is responsive, directly or indirectly, to PLCγ/$Ca^{2+}$. Alternatively, activation of a reporter protein in response to PLCγ/

$Ca^{2+}$ may be accomplished by operably linking the reporter protein to a promoter that is responsive to a protein that is induced by PLCγ/$Ca^{2+}$. In a specific embodiment, activation of a reporter protein in response to PLCγ/$Ca^{2+}$ may be accomplished by operably linking the reporter to a promoter responsive to NFAT. In an exemplary embodiment, an assay is a cell-based assay comprising contacting a cell expressing a membrane-bound form of TREM2, or a biologically active portion thereof, on the cell surface with a test compound and determining the ability of the test compound to modulate (e.g., stimulate or inhibit) the activity of TREM2 or biologically active portion thereof, wherein the cell is a 2B4 GFP-NFAT reporter T cell.

An arginine 47 to histidine (R47H) mutation of TREM2 is associated with an increased risk of developing disease neurodegenerative disease or disorder. The R47H mutation of TREM2 is associated with a loss-of-function in TREM2 signaling leading to defective microglia functions. Accordingly, there is a need to identify agonists that correct the impaired function of mutated TREM2. As such, the above disclosed screening assays may be performed with a membrane-bound form of TREM2, or a biologically active portion thereof, comprising the R47H mutation relative to SEQ ID NO:4. Accordingly, the above disclosed screening assays may be used to identify an agonist of TREM2, or a biologically active portion thereof, comprising the R47H mutation that can activate TREM2 despite the R47H mutation. Such an agonist may be useful in the prevention or treatment of a disease or disorder associated with TREM2 loss-of-function arising from the R47H mutation. Specifically, such an agonist may be useful in the prevention or treatment of a neurodegenerative disease or disorder such as Alzheimer's disease, frontotemporal dementia, amyotrophic lateral sclerosis and Nasu-Hakola disease, associated with TREM2 loss-of-function arising from the R47H mutation.

In another aspect, the present invention also provides reporter cells expressing a membrane-bound form of TREM2, or a biologically active portion thereof, on the cell surface, wherein the TREM2 optionally comprises a R47H mutation relative to SEQ ID NO:4 and the cells further comprise a reporter protein operably linked to a promoter that is responsive to a protein that is induced by PLCγ/$Ca^{2+}$. The cell may be an isolated cell as described in Section III(d). Methods of transfecting a protein and creating a reporter construct are disclosed herein. The method of use of this reporter cell may be as described in this section.

Definitions

The term "myeloid cells" as used herein refers to a series of bone marrow-derived cell lineages including granulocytes (neutrophils, eosinophils, and basophils), monocytes, macrophages, and mast cells. Furthermore, peripheral blood dendritic cells of myeloid origin, and dendritic cells and macrophages derived in vitro from monocytes in the presence of appropriate culture conditions, are also included.

The term "homologue," especially "TREM homologue" as used herein refers to any member of a series of peptides or nucleic acid molecules having a common biological activity, including antigenicity/immunogenicity and inflammation regulatory activity, and/or structural domain and having sufficient amino acid or nucleotide sequence identity as defined herein. TREM homologues can be from either the same or different species of animals.

The term "variant" as used herein refers either to a naturally occurring allelic variation of a given peptide or a recombinantly prepared variation of a given peptide or protein in which one or more amino acid residues have been modified by amino acid substitution, addition, or deletion.

The term "derivative" as used herein refers to a variation of given peptide or protein that are otherwise modified, i.e., by covalent attachment of any type of molecule, preferably having bioactivity, to the peptide or protein, including non-naturally occurring amino acids.

The term "antibody" is used in the broadest sense and specifically covers, for example, single monoclonal antibodies (including agonist, antagonist, and neutralizing antibodies), antibody compositions with polyepitopic specificity, polyclonal antibodies, single chain antibodies, and fragments of antibodies (see below) as long as they specifically bind a native polypeptide and/or exhibit a biological activity or immunological activity of this invention. "Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

"Antibody fragments" comprise a portion of an intact antibody, i.e. the antigen binding or variable region of the intact antibody or the Fc region of the intact antibody. In some contexts herein, fragments will be mentioned specifically for emphasis; nevertheless, it will be understood that regardless of whether fragments are specified, the term "antibody" includes such fragments as well as single-chain forms. As long as the polypeptide retains an ability to specifically bind its intended target, it is included within the term "antibody." Examples of antibody fragments include Fc, Fab, Fab', F(ab')2, and Fv fragments; $V_H$ fragments, $V_L$ fragments; single chain variable fragments (scFv); diabodies; triabodies; tetrabodies; linear antibodies; single-chain antibody molecules; and multispecific antibodies formed from antibody fragments. See, for example, Hudson and Souriau, *Nature Med.* 9: 129-134 (2003); and Holliger et al., *Proc. Natl. Acad. Sci. USA* 90: 644-6448 (1993).

The expression "linear antibodies" generally refers to the antibodies described in Zapata et al., Protein Eng., 8(10): 1057-1062 (1995), and U.S. Pat. No. 5,641,870, Example 2. Briefly, these antibodies comprise a pair of tandem Fd segments ($V_H$-$C_{H1}$-$V_H$-$C_{H1}$) which, together with complementary light chain polypeptides, form a pair of antigen binding regions. Linear antibodies can be bispecific or monospecific.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

A "single-chain Fv" comprises the $V_H$ and $V_L$ antibody domains connected into a single polypeptide chain. Preferably, the sFv polypeptide further comprises a polypeptide linker between the $V_H$ and $V_L$ domain which enables the sFv to form the desired structure for antigen binding. The length of the polypeptide linker can vary. In some embodiments, the polypeptide linker is at least 2, 3, 4, 5, 6, 7, 8, 9, 10, 11, 12, 13, 14, 15, 16, 17, 18, 19, 20 or more amino acids in length. A single-chain Fv can be abbreviated as "sFv" or "scFv." For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

The term "diabodies" refers to small antibody fragments prepared by constructing sFv fragments (see preceding paragraph) with short linkers (about 1-10 residues, preferably about 1-5 residues or about 5-10 residues, or even about 1-3 residues or about 3-5 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" sFv fragments in which the $V_H$ and $V_L$ domains of the two antibodies are present on different polypeptide chains. Diabodies are described more fully in, for example, EP 404,097; WO 93/11161; and Hollinger et al., PNAS USA, 90:6444-6448 (1993).

The term "polynucleotide" is intended to encompass a singular nucleic acid as well as plural nucleic acids, and refers to an isolated nucleic acid molecule or construct, e.g., messenger RNA (mRNA), cDNA, or vector DNA. A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding TREM2 or a fragment thereof contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode an immunoglobulin heavy chain variable region and an immunoglobulin light chain variable region. In addition, a vector, polynucleotide, or nucleic acid of the invention may encode heterologous coding regions, either fused or unfused to a nucleic acid encoding a binding molecule, an antibody, or fragment, variant, or derivative thereof. Heterologous coding regions include without limitation specialized elements or motifs, such as a signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. The term "control regions" refers to DNA sequences necessary for the expression of an operably linked coding sequence in a particular host organism. The control regions that are suitable for prokaryotes, for example, include a promoter, optionally an operator sequence, and a ribosome binding site. Eukaryotic cells are known to utilize promoters, polyadenylation signals, and enhancers. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or IRES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

"Isolated," when used to describe the various polypeptides disclosed herein, means a polypeptide has been identified and separated and/or recovered from a cell or cell culture from which it was expressed. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

An "isolated" nucleic acid encoding a polypeptide or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

An "isolated" cell is a cell isolated from a native source.

A "signal peptide" or "signal sequence" is a short peptide present at the N-terminus of a newly synthesized polypeptide that targets the polypeptide towards the secretory pathway. Generally a signal peptide is about 5 to about 30 amino acids in length, and has a common structure that may comprise a positively charged n-region, followed by a hydrophobic h-region and a neutral but polar c-region. Signal peptide databases provide access to single peptide sequences found in mammals, *Drosophila*, viruses, bacteria, and yeast. The choice of the signal peptide can and will vary depending on a variety factors including, but not limited to, the desired cellular location and type of cell.

A "purification moiety" is intended to encompass any molecule that facilitates the purification of a polynucleotide or, more preferably, a polypeptide of the invention including, but not limited to, biotin, avidin, stretpavidin, protein A, protein G, antibodies or fragments thereof, polyhistidine, Ni2+, Flag tags, myc tags. In preferred embodiments, a purification moiety comprises a peptide tag useful for purification include, but are not limited to, the "HA" tag, which corresponds to an epitope derived from the influenza hemagglutinin protein (Wilson et al., Cell 37 (1984), 767) and the "flag" tag. Purification moieties may further comprise a cleavage site to remove the moiety.

A "subject" includes, but is not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In embodiments where the animal is a mouse, the mouse may be a C57BL/6 mouse, a Balb/c mouse, a 129sv, or any other laboratory strain. In an exemplary embodiment, the subject is a C57BL/6J mouse. In a preferred embodiment, the subject is human.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to the Examples

Alzheimer's disease (AD) is a progressive neurodegenerative disorder with histopathological hallmarks of β-amyloid (Aβ) plaques and neurofibrillary tangles in the brain (Huang and Mucke, 2012; Tanzi, 2013). Although disease etiology is incompletely understood, families with inherited early-onset AD have mutations in three proteins directly involved in the Aβ processing pathway, suggesting a key role for Aβ in disease pathogenesis. Early studies have shown that brain microglia accumulate around Aβ plaques and occasionally contain Aβ in both AD patients (D'Andrea et al., 2004; McGeer et al., 1987; Perlmutter et al., 1990) and transgenic mouse models of AD (Dickson, 1999; Frautschy et al., 1998; Stalder et al., 1999). Microglia contribute to Aβ clearance, at least in the early phases of neurodegeneration (El Khoury et al., 2007); however, the ability of microglia to clear Aβ may wane with age (Streit et al., 2004; Streit and Xue, 2009). At late stages of AD, microglia may paradoxically contribute to the disease by releasing pro-inflammatory cytokines in response to Aβ deposition (El Khoury et al., 2007; Hickman et al., 2008).

Recent genome-wide association studies (GWASs) have shown that a rare Arginine-47-Histidine (R47H) mutation of the triggering receptor expressed on myeloid cells 2 (TREM2) is associated with a substantial increase in the risk of developing AD (Guerreiro et al., 2013b; Jonsson et al., 2013). TREM2 is a cell-surface receptor of the Ig-superfamily that is expressed by microglia and osteoclasts in vivo (Kiialainen et al., 2005; Paloneva et al., 2002; Schmid et al., 2002; Thrash et al., 2009) as well as monocyte-derived DC, bone marrow-derived macrophages, and macrophage cell lines in vitro (Bouchon et al., 2001; Daws et al., 2001). Although TREM2 was detected in other cells of the CNS (Guerreiro et al., 2013b; Sessa et al., 2004), these observations have not been confirmed (Jiang et al., 2014). TREM2 binds anionic carbohydrates, anionic bacterial products, and various phospholipids (Cannon et al., 2012; Daws et al., 2003). It transmits intracellular signals through the associated transmembrane adaptor DAP12, which recruits the protein tyrosine kinase Syk, leading to phosphorylation of many downstream mediators, such as PLC-γ, PI-3K, and Vav2/3 (Ford and McVicar, 2009; Peng et al., 2010). Individuals homozygous for rare mutations that impair expression of either TREM2 or DAP12 develop lethal forms of progressive dementias such as Nasu-Hakola disease (NHD) and frontotemporal dementia (FTD) (Guerreiro et al., 2013a, 2013c; Kleinberger et al., 2014; Paloneva et al., 2002).

The association between the R47H mutation of TREM2 and the increased risk for late-onset AD suggests that microglia may require TREM2 to respond to Aβ deposition and to limit neuronal degeneration. Consistent with this hypothesis, we recently showed that APPPS1-21 transgenic mice, an AD model with rapid deposition of Aβ, have a marked decrease in the number and size of Aβ-associated microglia when they lack one copy of the Trem2 gene, although this defect did not increase Aβ accumulation (Ulrich et al., 2014). The mechanisms underlying this altered microglial response and its impact on Aβ deposition have not been delineated. To address these questions, we studied TREM2 deficiency in the 5×FAD mouse model of AD, in which AR deposition develops less rapidly than in APPPS1-21 mice (Oakley et al., 2006). We find that both TREM2 deficiency and haploinsufficiency augment Aβ accumulation due to a dysfunctional response of microglia, which become apoptotic rather than undergoing activation and proliferation. We further show that TREM2 sustains microglial survival by synergizing with colony stimulating factor-1 receptor (CSF-1R) signaling. Finally, we demonstrate that TREM2 binds to a broad array of anionic lipids, which were found in association with fibrillar Aβ and are also exposed during neuronal and glial cell death. Remarkably, the R47H mutation impairs TREM2 binding to anionic lipids. We conclude that TREM2 is a receptor that detects damage-associated lipids, thereby enabling microglia to sense Aβ accumulation and cell damage, as well as supporting microglial survival and AR reactive microgliosis.

Example 1. TREM2 Modulates Aβ Accumulation

Figure 1D:
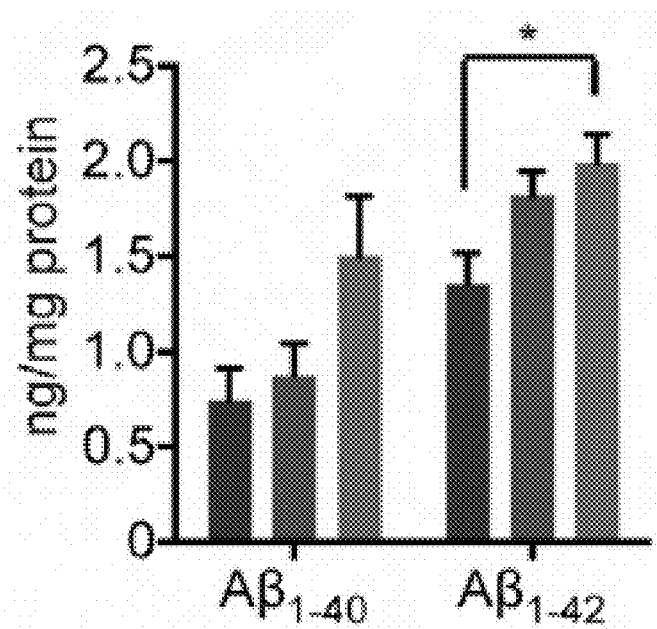
Figure 1E:
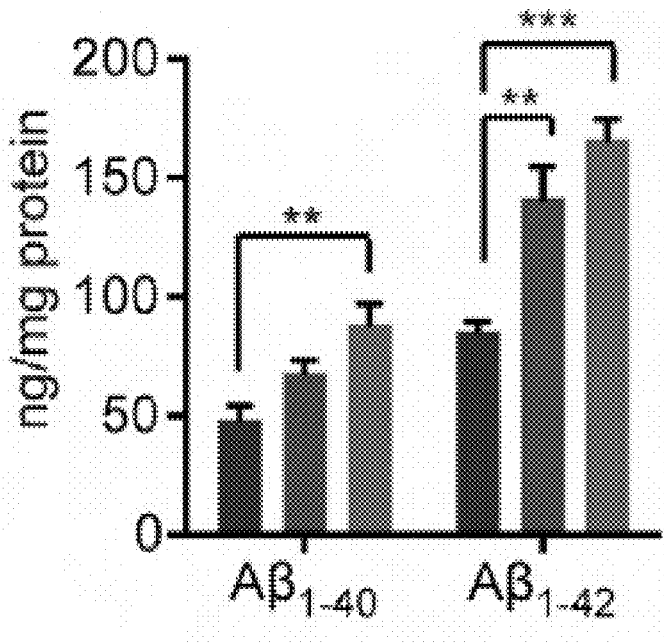
Figure 1F:
Figure 1G:
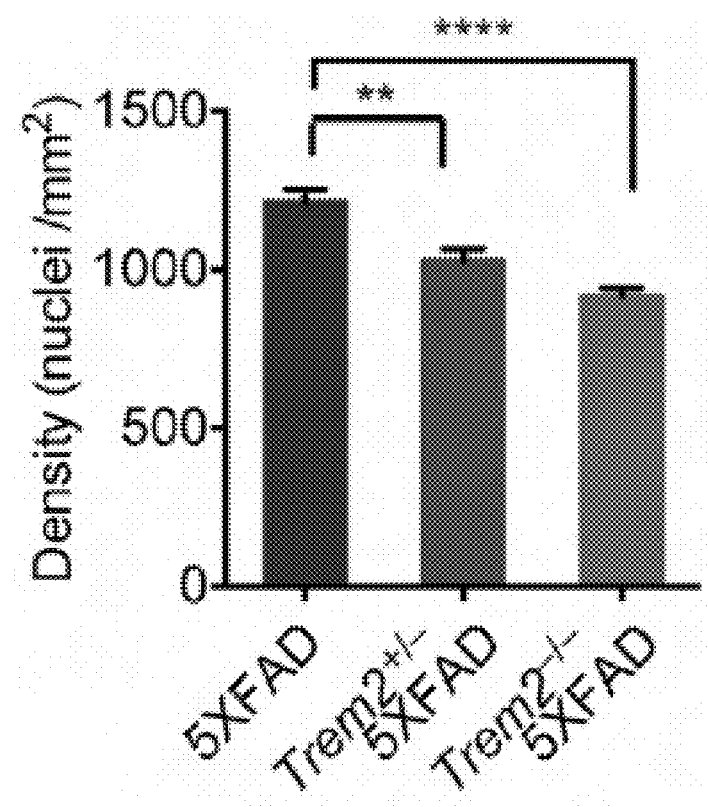

We examined the deposition of AR aggregates in Trem2$^{-/-}$ mice bred to 5×FAD transgenic mice (APPSw-FILon, PSEN1*M146L*L286V), an accelerated mouse model of AD (Oakley et al., 2006). Staining of matched coronal brain sections from Trem2$^{-/-}$5×FAD mice and control 5×FAD mice at 8.5 months of age with a monoclonal antibody (mAb) against Aβ revealed significantly increased Aβ accumulation in the hippocampal but not cortical regions of Trem2$^{-/-}$5×FAD mice (FIGS. 1A,B and 8A). Trem2$^{+/-}$5×FAD mice had an intermediate phenotype, although it was not statistically significant (p=0.104). We also determined levels of Aβ$_{40}$ and Aβ$_{42}$ in the hippocampus and cortex of these mice by ELISA. While levels of soluble Aβ$_{40}$ and Aβ$_{42}$ were similar (FIGS. 1C and 8B), we detected a significant increase in insoluble, guanidine-extracted Aβ$_{40}$ and Aβ$_{42}$ in the hippocampal regions of Trem2$^{-/-}$5×FAD mice compared to 5×FAD mice (FIG. 1D,E). Moreover, there was a significant effect of Trem2 gene copy number on insoluble Aβ protein levels in the hippocampi, whereas levels of insoluble Aβ$_{40}$ and Aβ$_{42}$ in the cortex were equivalent across all three genotypes (FIG. 8C,D). We also found that the loss of layer V neurons, a feature of 5×FAD mice (Eimer and Vassar, 2013; Oakley et al., 2006), was more prominent in Trem2$^{-/-}$5×FAD mice (FIG. 1F,G). Trem2$^{+/-}$5×FAD mice presented an intermediate phenotype. Collectively, these data suggest that TREM2 modulates Aβ accumulation, limiting neuronal loss. The lack of a significant difference in Aβ accumulation in the cortices of Trem2$^{-/-}$5×FAD mice and 5×FAD mice may be the result of the fast kinetics of Aβ deposition in 5×FAD mice, such that the potential cortical differences are no longer detectable at 8.5 month of age.

Example 2. TREM2 Is Required for Reactive Microgliosis

Figures 2D, 2E:
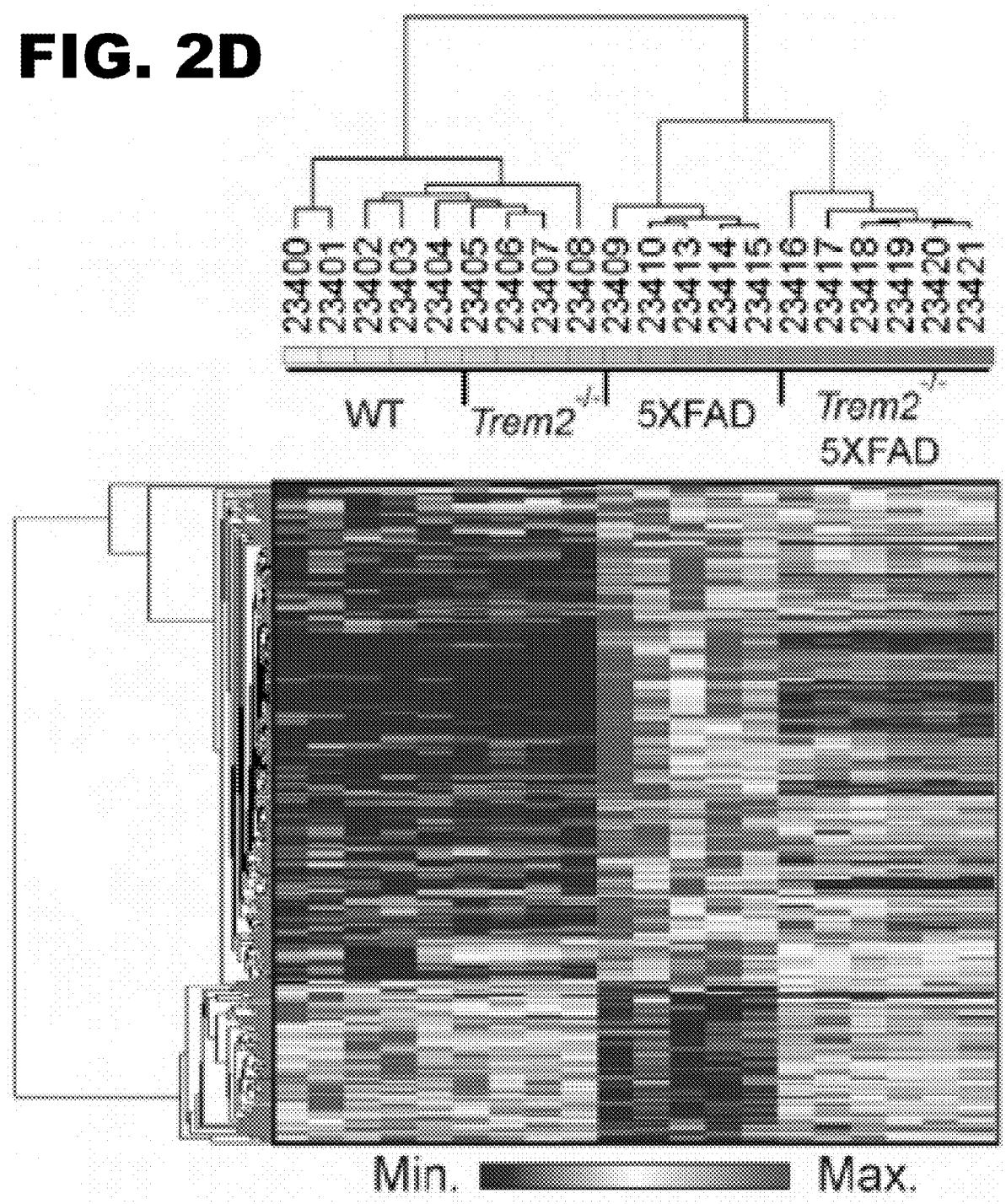
Figure 2F:
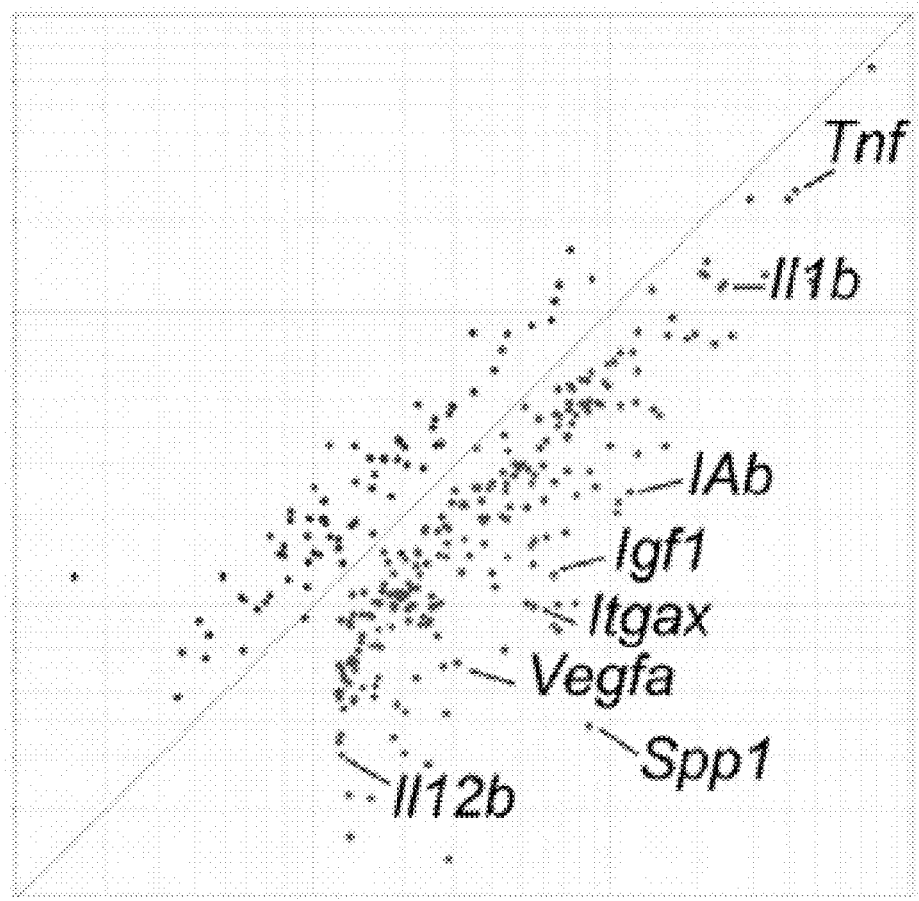
Figure 9A:
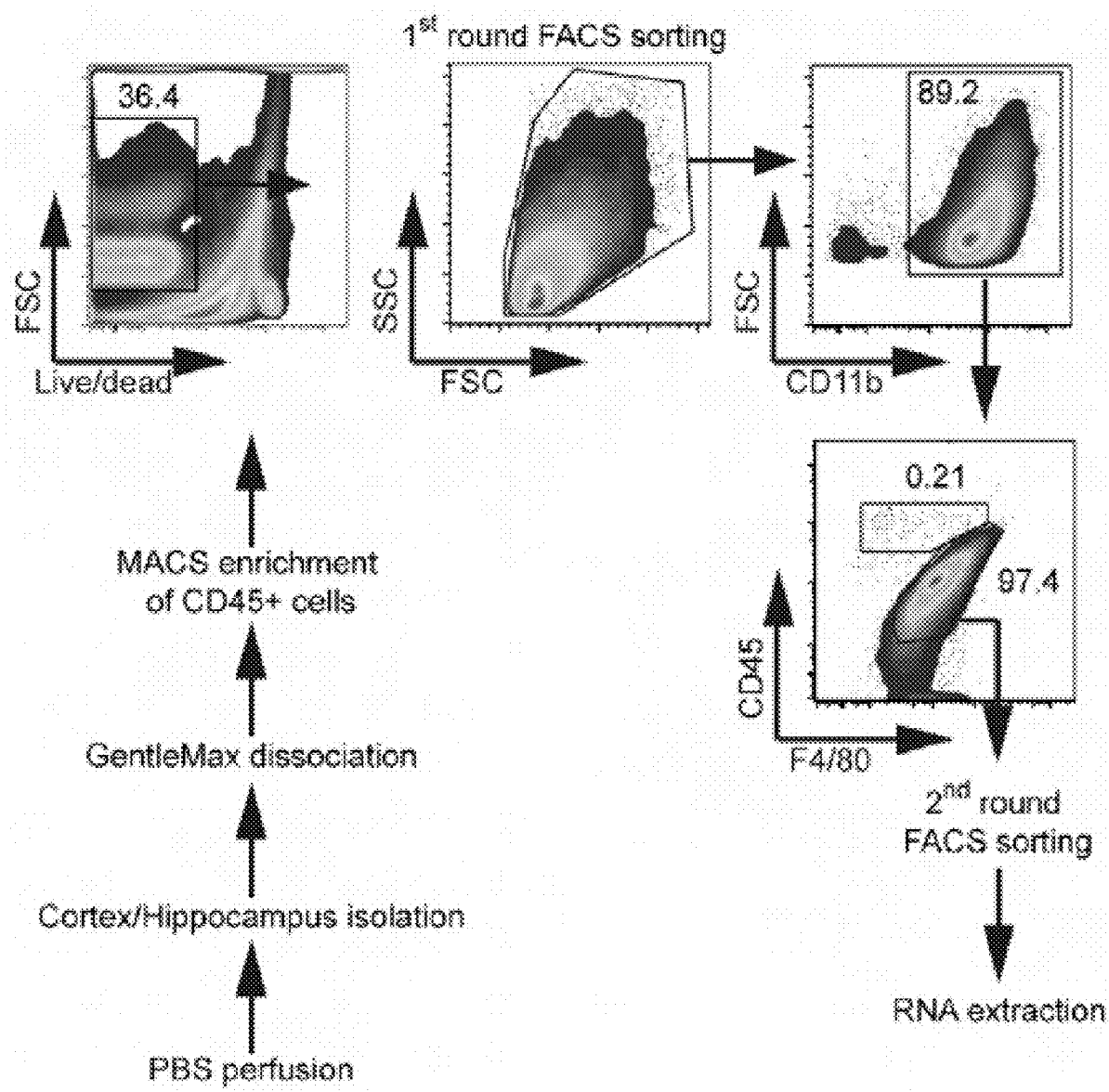
Figure 9B:
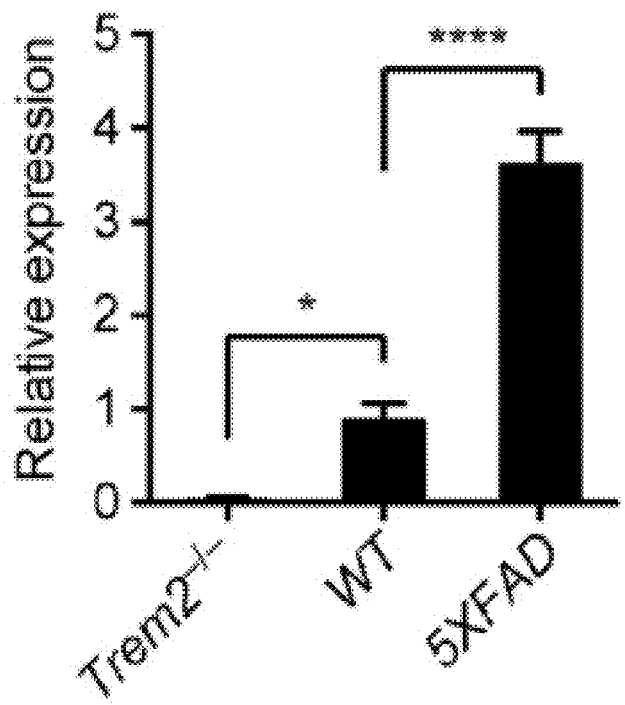
Figure 9C:
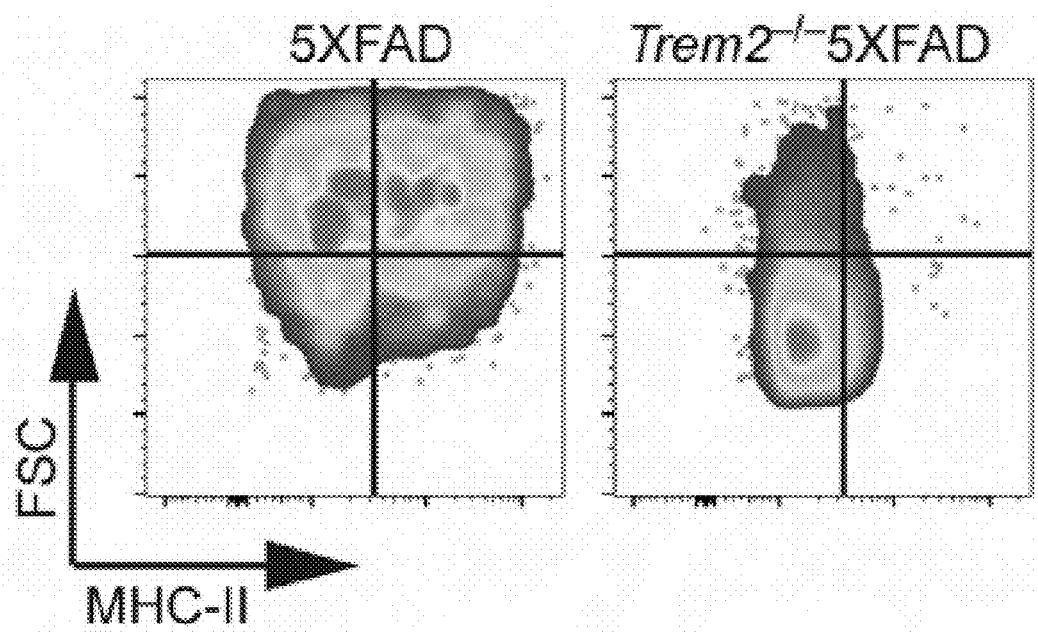
Figure 9D:
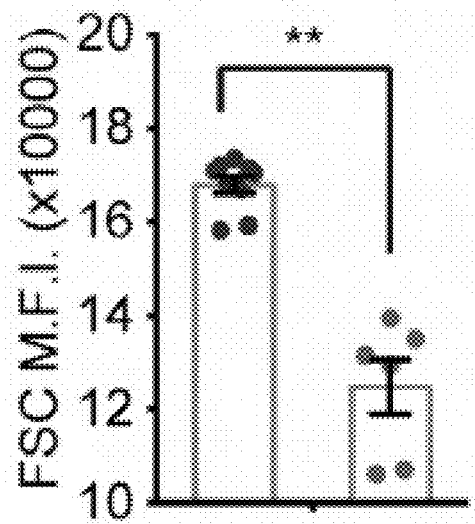
Figure 9E:
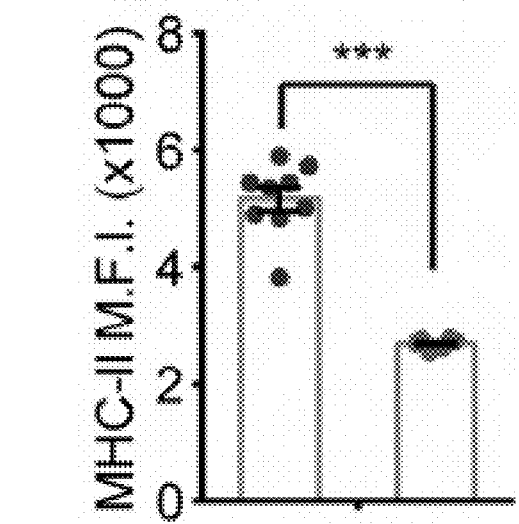
Figure 9F:
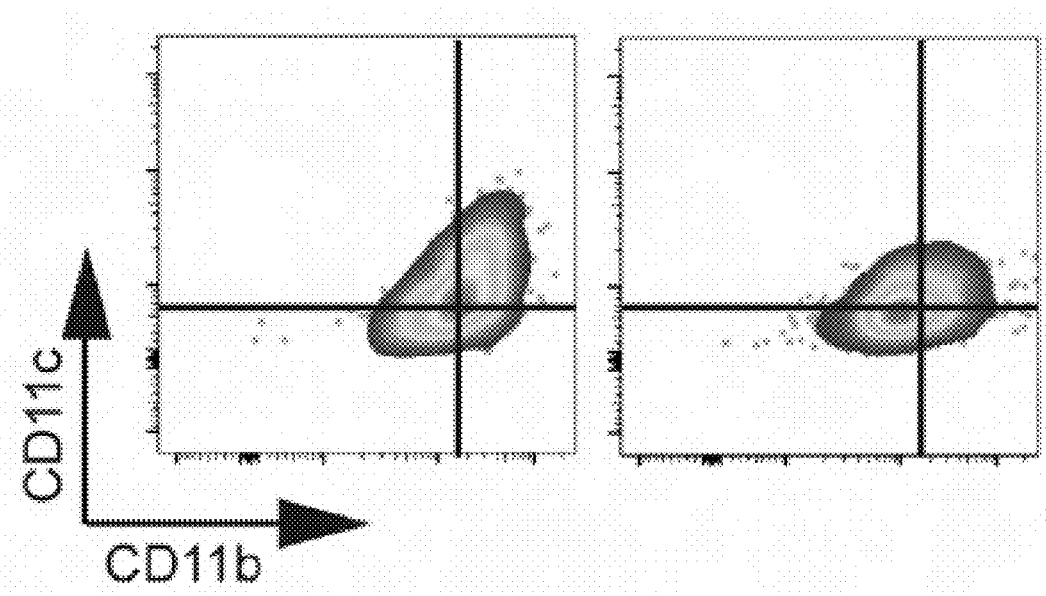
Figure 9G:
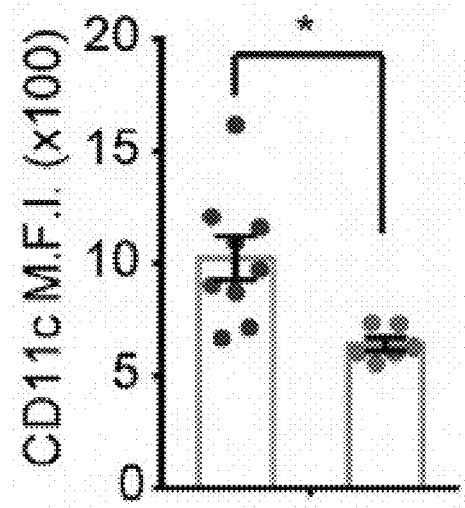
Figure 9H:
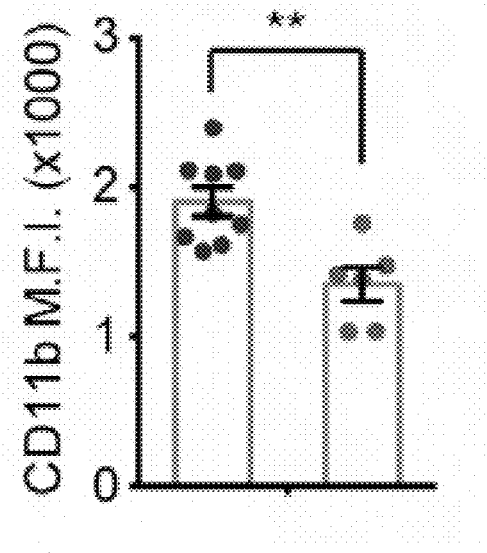
Figure 9I:
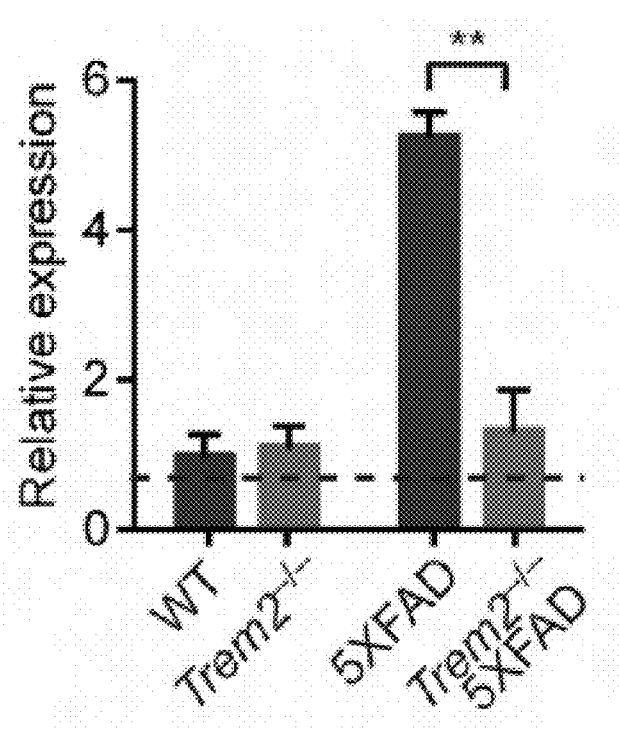
Figure 9J:
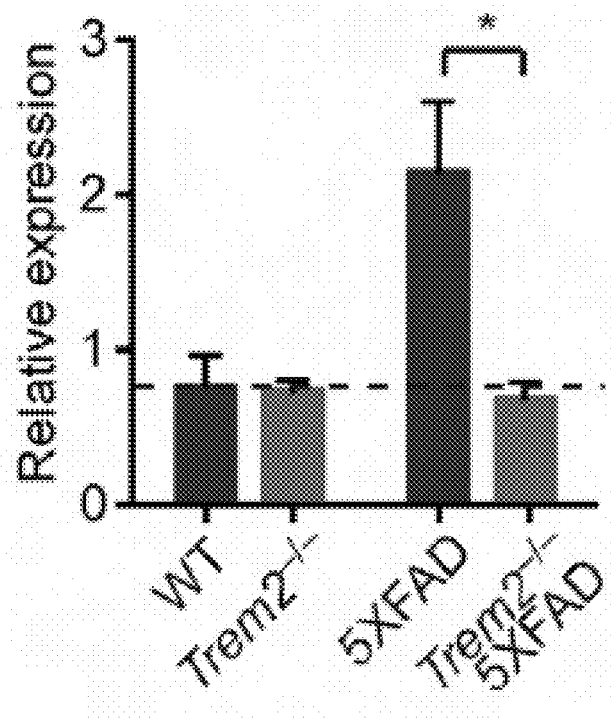
Figure 9K:
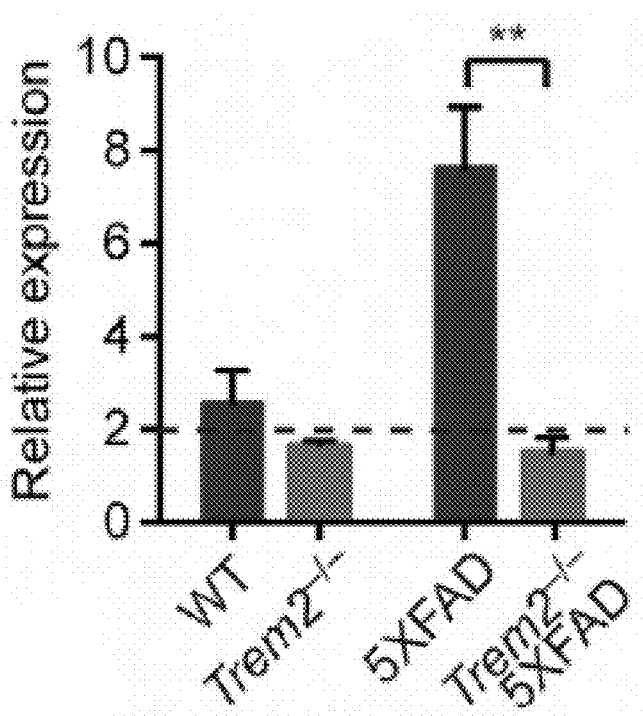
Figure 9L:
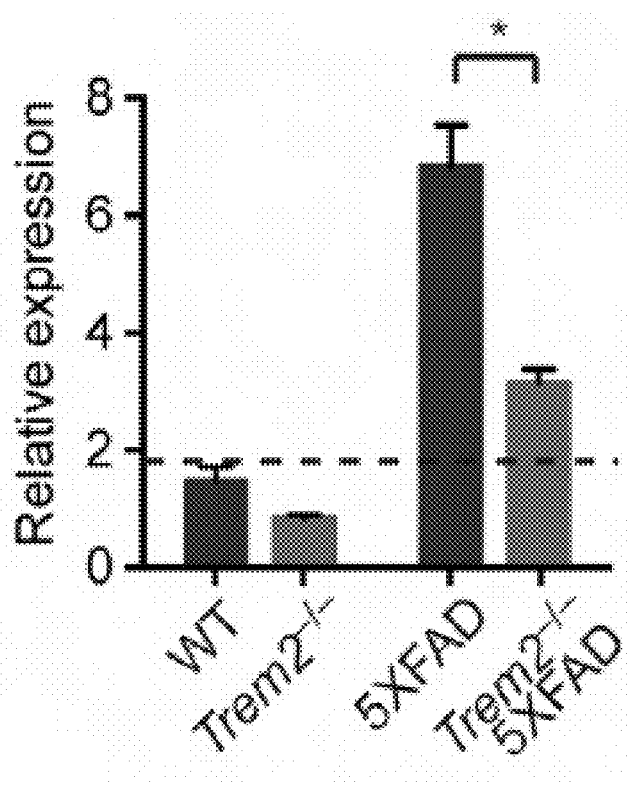

How does lack of TREM2 impact Aβ accumulation? Although TREM2 expression has been reported in CNS cells other than microglia (Guerreiro et al., 2013b; Sessa et al., 2004), this finding is controversial (Jiang et al., 2014). Indeed, a recently published RNA sequencing (RNA-seq) data set demonstrated that Trem2 is specifically expressed in microglia, but not other cells in the CNS under steady-state conditions (Butovsky et al., 2014). We also found that Trem2 expression is further upregulated in microglia isolated from 5×FAD mice during Aβ deposition (FIG. 9A,B). Thus, we focused our studies on microglia. One of the many effects of Aβ deposition is the induction of reactive microgliosis, which involves the expansion of microglia and conversion to an activated state (Ransohoff and Cardona, 2010). Microgliosis predominantly involves the proliferation of brain-resident microglia, with some contribution from blood-borne monocytes and microglia migrating from adjacent non-damaged brain areas (El Khoury et al., 2007; Grathwohl et al., 2009; Maim et al., 2005; Mildner et al., 2011; Simard et al., 2006; Stalder et al., 2005). To evaluate the impact of TREM2 deficiency on Aβ-induced microglial responses in 5×FAD mice, we examined transcriptional profiles of microglia purified from 5×FAD and Trem2$^{-/-}$5×FAD mice as well as transgene negative wild-type (WT) and Trem2$^{-/-}$ littermates (FIG. 9A). To evaluate changes in global transcriptomes, we first performed principle component analysis (PCA) of the top 15% most variable transcripts. We noticed that WT and Trem2$^{-/-}$ replicates clustered closely, suggesting a limited impact of TREM2 deficiency in the steady state, which was confirmed by a volcano plot comparing the two groups (FIGS. 2A,B). In contrast, 5×FAD microglial replicates were dramatically different from WT replicates (FIG. 2A), and a volcano plot revealed that 5×FAD microglia expressed many more transcripts including those associated with microglial activation (MHC-II, CD11c), production of inflammatory cytokines (interleukin-1b [IL-1b], tumor necrosis factor-α [TNF-α], IL-12, and SPP1), and neurotrophic factors (insulin growth factor 1 [IGF-1] and VEGFA) (FIG. 2C). Trem2$^{-/-}$ 5×FAD microglia had an intermediate behavior in the principle component analysis compared to 5×FAD and WT microglia. To further interrogate how TREM2 deficiency affected the microglial response to Aβ deposition, we selected the transcripts upregulated 2-fold between 5×FAD and WT microglia (FIG. 2C) and compared the expression of these transcripts among the entire data set. We found that Trem2$^{-/-}$ 5×FAD microglia failed to upregulate these transcripts and behaved more similarly to WT microglia, as shown by hierarchical clustering and expression-by-expression plots (FIGS. 2D-F). Flow cytometric analysis of isolated microglia confirmed phenotypic changes in 5×FAD microglia consistent with increased activation, including a marked increase in cell size and strong upregulation of MHC-II, CD11c, and CD11b (FIGS. 9C-G). We also confirmed increased expression of inflammatory cytokine transcripts by qPCR in whole-brain lysates of 5×FAD mice (FIGS. 9I-L). However, in Trem2$^{-/-}$ 5×FAD mice, these changes were markedly attenuated (FIGS. 2D-F and FIGS. 9C-L). In fact, Trem2$^{-/-}$5×FAD microglia were phenotypically more similar to WT microglia in steady state than 5×FAD microglia. Overall, these results implied that TREM2 is required for reactive microgliosis.

Example 3. Microglia Fail to Colocalize with Aβ Plaques in Trem2$^{-/-}$ Mice

Initial staining of microglia in coronal brain sections with Iba-1 revealed very similar distribution of microglia in Trem2$^{-/-}$, Trem2$^{+/-}$ and WT adult mice (FIGS. 10A-C). However, co-staining of coronal brain sections from Trem2$^{-/-}$5×FAD and 5×FAD mice with Iba-1 and X-34, to visualize microglia and Aβ plaques, respectively, showed remarkable differences. We found that Trem2-/-5×FAD mice had reduced Iba-1 reactivity both in the hippocampi and cortices compared to 5×FAD mice (FIGS. 3A-D). This was particularly evident in the areas surrounding Aβ plaques (FIGS. 3E,F), suggesting a preferential reduction of microgliosis near amyloid deposits. Trem2$^{+/-}$5×FAD mice also had a partial reduction of amyloid-associated Iba-1 reactivity.

Examination of a second model of AD, APPPS1-21 mice that have been bred to Cx3cr1$^{GFP/+}$ mice in order to visualize endogenous microglia, confirmed that complete TREM2 deficiency results in a marked reduction of GFP microglial clusters around Aβ plaques (FIG. 10D-FIG. 10F). This corroborates our previous observation that TREM2 haploinsufficiency correlates with fewer amyloid-associated microglia in APPPS1-21×Cx3cr1$^{GFP/+}$ mice (Ulrich et al., 2014). Moreover, since Cx3CR1 marks brain-resident microglia (Ransohoff and Cardona, 2010), these results also suggest that TREM2 deficiency primarily affects the response of brain-resident microglia to Aβ.

Figure 11A:
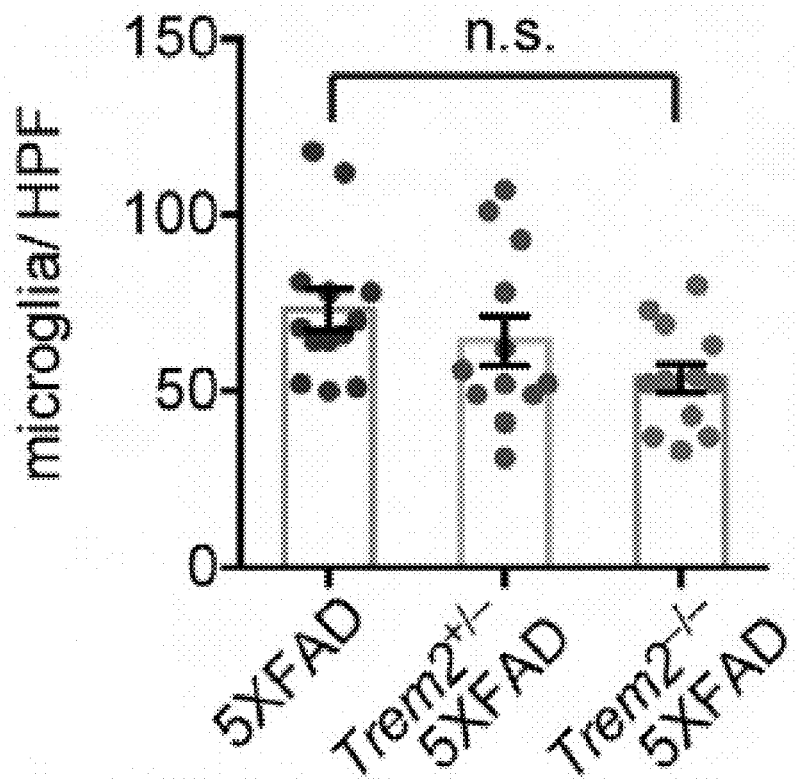
Figure 11B:
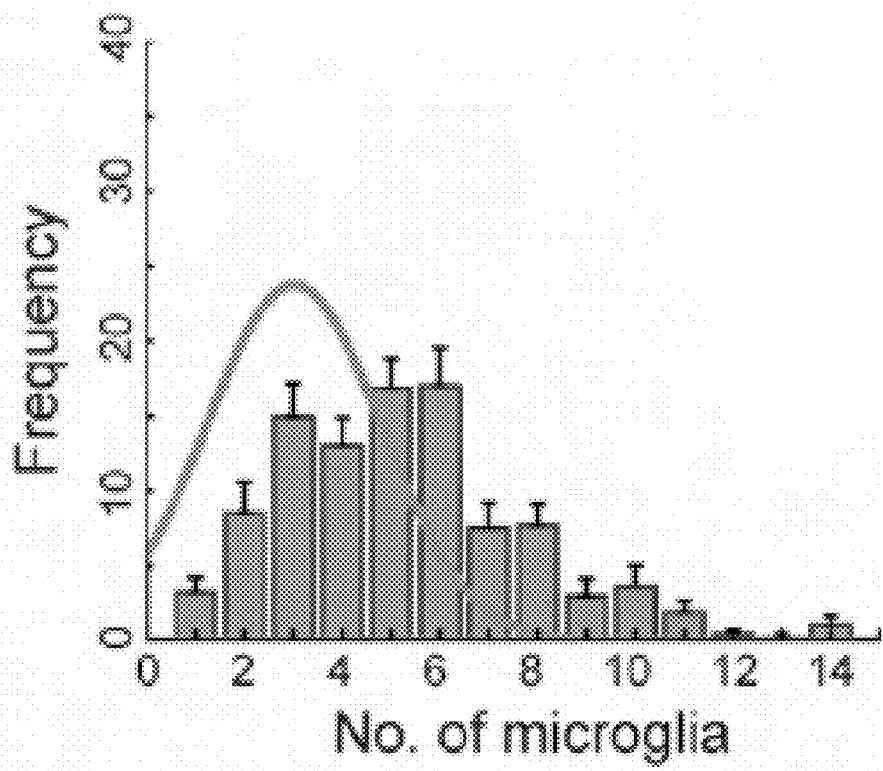
Figure 11C:
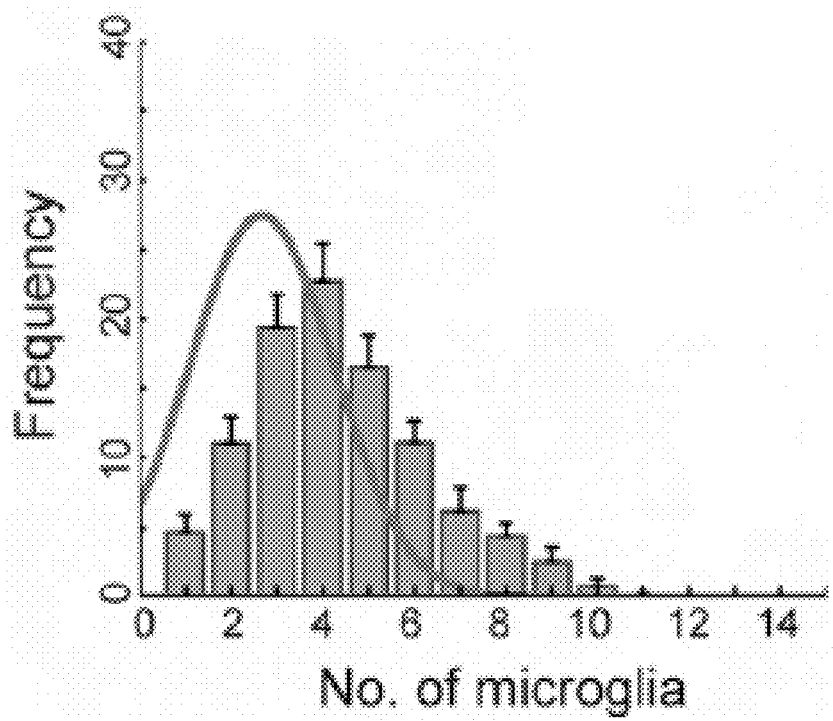
Figure 11D:
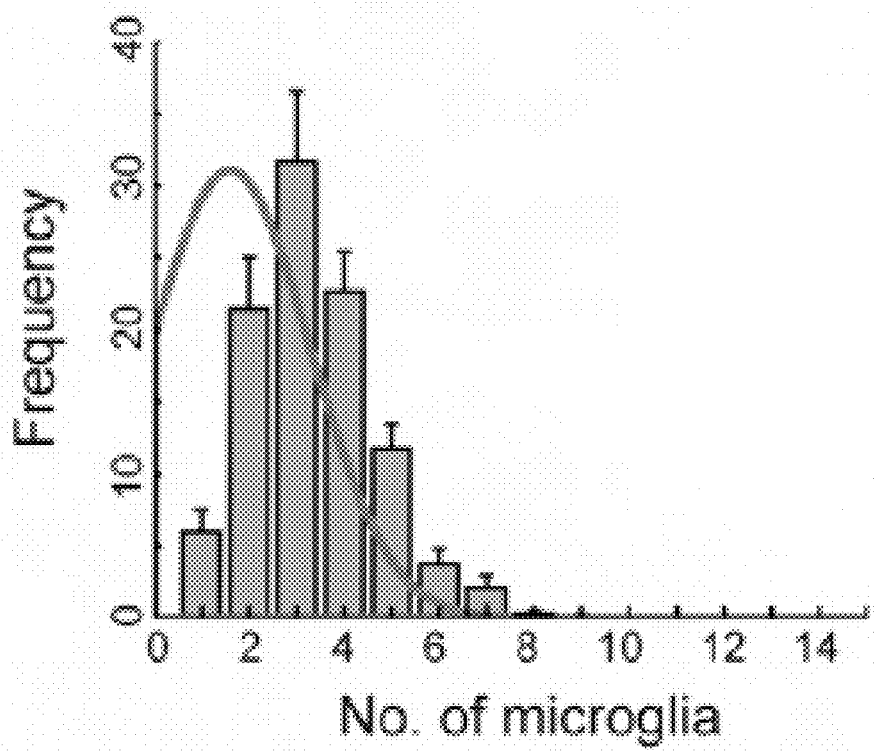

To further quantify the number of microglia around Aβ plaques, we recorded the coordinates (x, y, and z) of all visible microglial cell bodies and the location of Aβ plaques in each z stack confocal image and calculated the number of microglia within 30 μm radius of the plaques (defined as plaque-associated microglia) and non-plaque-associated microglia. While no statistically significant difference was observed among non-plaque-associated microglia (FIG. 11A), we noted a high degree of microglial clustering around amyloid plaques in 5×FAD mice (average 4.28 microglia per plaque), which gradually decreased in Trem2$^{+/-}$5×FAD mice (average 3.42 microglia per plaque) and Trem2$^{-/-}$5×FAD mice (average 2.36 microglia per plaque) (FIG. 4A, FIG. 4B). To confirm the "negligence" of microglial responses to Aβ in the absence of TREM2, we compared the actual frequency of microglia per plaque to that obtained by Monte Carlo simulations where the same numbers of microglia and plaques observed in z stack images were positioned by chance in each genotype (FIG. 11B-FIG. 11D). The probability that observed microglial frequencies per plaque fell outside of simulated random frequencies was inversely proportional to Trem2 gene copy number (FIG. 4C). Moreover, while 27.9% of microglial distribution in 5×FAD mice with respect to Aβ plaques was not explained statistically by chance, the frequency of nonrandom microglial distribution was reduced to 9.5% in Trem2$^{-/-}$ 5×FAD mice (FIG. 4D).

Figure 4H:
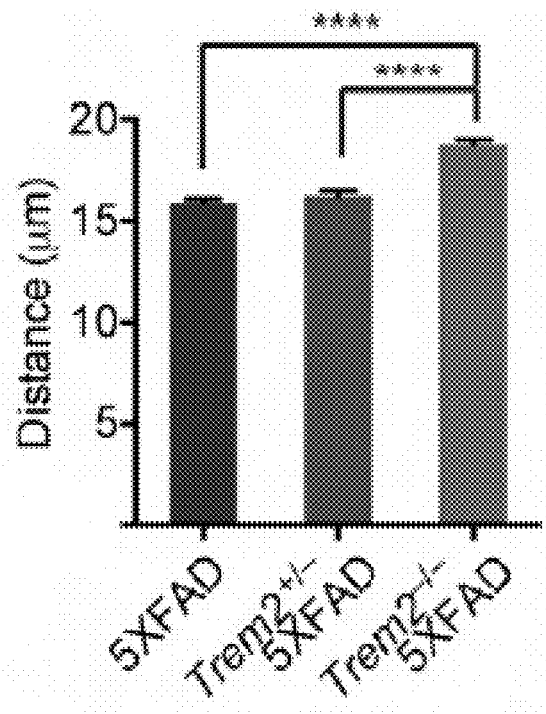

Another feature of reactive microgliosis is morphological transformation. In 5×FAD mice, plaque-associated microglia showed morphological changes associated with microglial activation, including a partial retraction and a slight hypertrophy of the microglial cell processes as well as an increase in size (FIG. 4E-FIG. 4G). These changes in microglial morphology were significantly attenuated in Trem2$^{+/-}$5×FAD and Trem2$^{-/-}$ 5×FAD mice (FIG. 4E-FIG. 4G) and were paralleled by an increased distance between microglia and the center of their associated plaques (FIG. 4H). Collectively, these data indicate that TREM2 is essential for the microglial response to Aβ plaques.

Example 4. TREM2 Deficiency Affects Microglial Survival in 5×FAD Mice

Why is TREM2 required for Aβ reactive microgliosis? We first hypothesized that TREM2 may be necessary for Aβ uptake and microglial activation. We initially investigated the impact of TREM2 deficiency on microglial activation in vitro. For this analysis, we used primary microglia isolated from adult mice and expanded in the presence of optimal amounts of CSF-1 and TGF-β (FIG. 12A), as they closely resemble microglia in vivo (Butovsky et al., 2014). TREM2 deficiency did not affect microglial expansion, migration, or TNF-α secretion in response to Aβ (FIG. 12B-FIG. 12D). In contrast, Trem2$^{-/-}$ microglia produced significantly more TNF-α than WT microglia in response to lipopolysaccharide (LPS), consistent with previous demonstrations that TREM2 attenuates cytokine responses to certain TLR ligands (Hamerman et al., 2006; Turnbull et al., 2006). Moreover, TREM2 deficiency had very little impact on microglial uptake of Aβ aggregates (FIG. 12E) or their subsequent proteolytic processing, as demonstrated by similar degradation of the intracellular concentration of Aβ after initial loading (FIG. 12F). Thus, TREM2 deficiency does not engender a direct defect in phagocytosis of Aβ.

Previous studies have suggested that the CSF-1-CSF-1R pathway promotes reactive microgliosis (Chitu and Stanley, 2006) and Aβ clearance (Mitrasinovic et al., 2003); consistent with this, CSF1-deficient osteopetrotic (op/op) mice are characterized by increased deposition of Aβ, scarcity of microgliosis and neuronal loss (Kaku et al., 2003). We had previously demonstrated that TREM2 signaling via its associated adaptor DAP12 synergizes with CSF-1R signaling to promote survival of macrophages (Otero et al., 2009, 2012). Specifically, TREM2/DAP12 were required to induce activation of the Syk tyrosine kinase pathway downstream of CSF-1R (Otero et al., 2009; Zou et al., 2008). Thus, we hypothesized that TREM2 may synergize with CSF-1-CSF-1R signaling to sustain reactive microgliosis during Aβ deposition. We initially tested this hypothesis in vitro by measuring the survival of adult primary microglial cultures from WT and Trem2$^{-/-}$ mice in the presence of graded concentrations of CSF-1 (10%, 1%, and 0.1% L-cell conditioned medium [LCM]). While TREM2 deficiency did not affect viability at high concentrations of CSF-1 (10% and 1%), Trem2$^{-/-}$ microglia were markedly less viable than WT microglia in 0.1% CSF-1 (FIG. 5A-FIG. 5D). We next purified microglia from Trem2$^{-/-}$5xFAD and 5xFAD mice and cultured them in medium containing low levels of CSF-1 (0.1% LCM) for 5 days. Trem2$^{-/-}$5xFAD microglia were significantly less viable than 5xFAD microglia (FIG. 5E). Since CSF-1R captures CSF-1 and targets it for degradation (Stanley and Chitu, 2014), the reduced survival of Trem2$^{-/-}$ microglia at low CSF-1 concentrations may reflect a marked susceptibility of these cells to CSF-1 deprivation that occurs when microglia consume a limited supply of CSF-1. Indeed, CSF-1R blockade reduced viability of 5xFAD microglia, confirming that the pro-survival effect of TREM2 cannot replace that of CSF-1R, but only synergize with it (FIG. 5E).

To evaluate the impact of TREM2 deficiency on microglia apoptosis in vivo, we analyzed coronal sections of Trem2$^{-/-}$ 5xFAD and 5xFAD mice by TUNEL staining. Markedly more TUNEL$^+$ microglia were evident in Trem2$^{-/-}$5xFAD mice than the very few observed in control 5xFAD mice (FIG. 5F-FIG. 5H), corroborating a role for TREM2 in maintaining microglial survival during reactive microgliosis. Consistent with this, significantly fewer microglia were recovered from the cortices and hippocampi of Trem2$^{-/-}$5x FAD mice than from 5xFAD mice (FIG. 5I). We postulate that reactive microgliosis is associated with increased CSF-1 uptake by CSF-1R and degradation restricting CSF-1 range of action, such that microglia in close proximity must compete for CSF-1. Because of their inability to survive CSF-1 limitation, TREM2-deficient microglia are incapable of sustaining reactive microgliosis and undergo apoptosis rather than becoming activated and expanding.

Figure 6C:
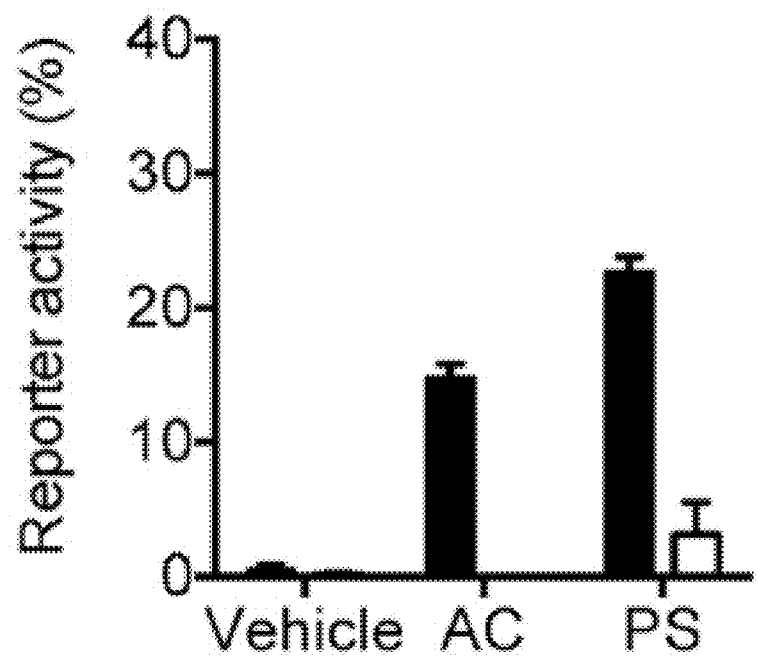
Figure 6D:
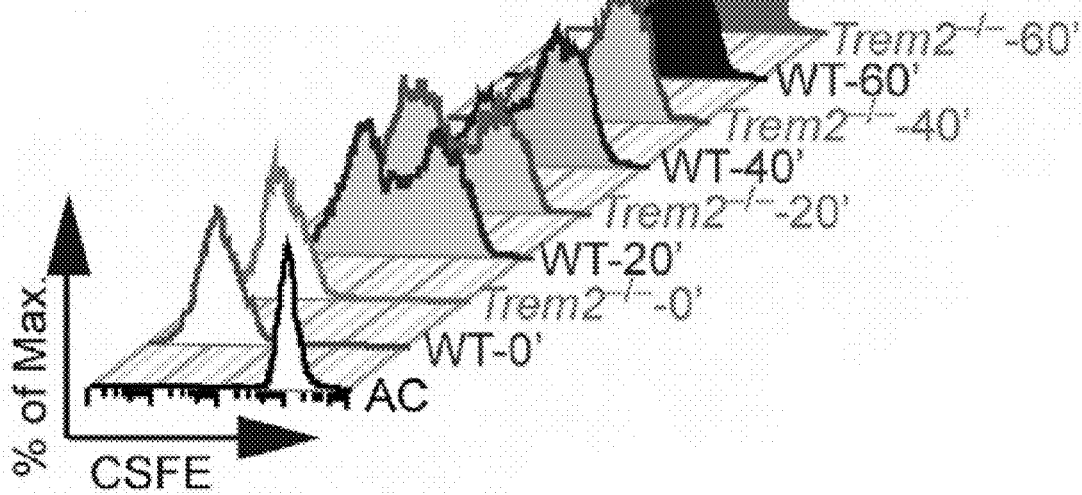
Figure 6E:
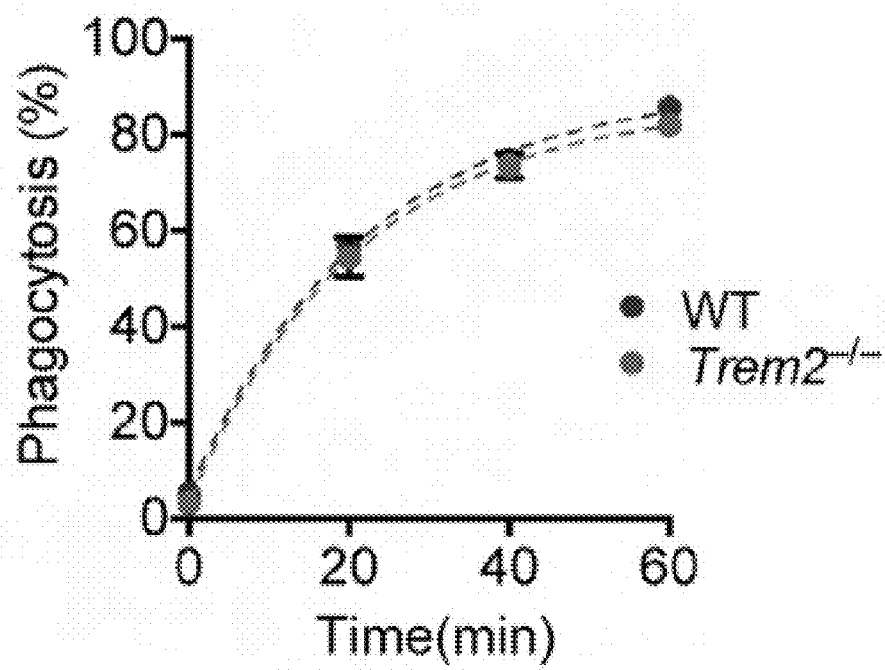

Example 5. TREM2 Is a Sensor for Anionic and Zwitterionic Lipids that Accumulate in the CNS During Aβ Deposition We next sought to identify the ligand(s) that trigger TREM2 signaling during Aβ deposition. Since TREM2 binds anionic carbohydrates, anionic bacterial products, and phospholipids (Cannon et al., 2012; Daws et al., 2003), we focused on lipids that have been shown to accumulate during Aβ deposition and might stimulate microglia. These included negatively charged phospholipids, which have been shown to associate with Aβ in lipid membranes (Ahyayauch et al., 2012; Nagarathinam et al., 2013); membrane phospholipids, such as phosphatidyl-serine, which are exposed by damaged neurons and glial cells; and anionic and zwitterionic non-phosphate lipids, such as sulfatides and sphingomyelin, which are released by damaged myelin. We transfected human TREM2 in reporter cells that express GFP under the control of NFAT, such that Ca$^{2+}$ mobilization turns on GFP expression when TREM2 is engaged. Incubation of TREM2 reporter cells with many of these lipids activated reporter activity, although to differing extents, with phosphatidylcholine (PC) and sphingomyelin (SM) performing best in these assays (FIG. 6A, FIG. 6B). Similar results were obtained with a mouse TREM2 reporter (data not shown). Addition of a blocking TREM2 antibody abolished reporter activation by all ligands, demonstrating specificity (FIG. 6B). Interestingly, other potential candidates, such as cardiolipin, which is released by damaged mitochondria, did not significantly activate the TREM2 reporter despite its phospholipid structure. This suggests that the ability to engage TREM2 may only partially depend on the presence of negatively charged moieties like phosphoric acid (FIG. 6A, FIG. 6B). Furthermore, TREM2 reporter activation was not detected with plate-bound synthetic or extracted Aβ (data not shown). In agreement with the ability of phosphotidylserine (PS) to activate TREM2 reporter cells, apoptotic cells, which expose PS on the cell surface, also activated TREM2 reporter cells (FIG. 6C). However, microglia isolated from Trem2$^{-/-}$ 5xFAD and 5xFAD mice engulfed apoptotic cells equally well (FIG. 6D, FIG. 6E). Thus, TREM2 is not directly involved in phagocytosis of apoptotic cells. We conclude that TREM2 is a sensor for several anionic and zwitterionic lipids that are exposed during Aβ deposition as well as during neuronal and glial cell death.

Example 6. R47H Mutation Impairs TREM2 Recognition of Lipid Ligands

What is the impact of the R47H mutation on TREM2 ligand recognition? We generated TREM2 R47H reporter cells and compared their response to identified ligands to that of TREM2 reporter cells. The R47H mutation considerably reduced reporter activation in response to many ligands, including phosphatidic acid (PA), phosphatidylglycerol (PG), PS, phosphatidylinositol (PI), and sulfatides (FIG. 7A-FIG. 7G). The R47H mutation had less impact on SM recognition and very little influence on PC-mediated activation. Importantly, the R47H mutation did not detectably affect cell-surface expression or signaling of TREM2, as assessed by stimulating the R47H reporter cells with a plate-bound anti-TREM2 antibody (FIG. 7H). Thus, these data suggest that the R47H reduces the overall capacity of TREM2 to bind anionic ligands.

Discussion for the Examples

This study showed that TREM2 modulates Aβ accumulation in the 5×FAD mouse model of AD, thereby reducing neuronal damage. The importance of TREM2 in Aβ clearance is underscored by the fact that even the loss of one copy of Trem2 gene is sufficient to increase Aβ accumulation. TREM2 acts in microglia by supporting Aβ-reactive microgliosis, a process of expansion and activation that leads to microglial clustering around Aβ plaques and subsequent Aβ removal (Ransohoff and Cardona, 2010). In the absence of TREM2, this microgliosis is impaired. In fact, microglia from Trem2$^{-/-}$5×FAD mice are unable to survive, as evidenced by the accumulation of apoptotic microglia around Aβ plaques. Cells involved in TREM2-dependent microgliosis had phenotypic features of brain resident microglia, such as expression of Cx3CR1. However, it is possible that monocytes from peripheral blood contribute to microgliosis and that TREM2 supports their survival as well.

Previous studies have shown that CSF-1-CSF-1R signaling is essential for microgliosis in response to Aβ (Chitu and Stanley, 2006; Kaku et al., 2003; Mitrasinovic et al., 2003). Since CSF-1 is rapidly consumed during this process (Stanley and Chitu, 2014), there is probably a limited supply of CSF-1 surrounding the Aβ plaques. Our results demonstrate that TREM2 provides a signal that is necessary for survival of microglia at low CSF-1 concentrations. We postulate that TREM2 acts as a costimulatory molecule that sustains survival of microglia, which are activated and proliferate in the presence of Aβ. Previous studies of cultured myeloid cells indicate that TREM2 may synergize with CSF-1-CSF-1R signaling to activate the protein tyrosine kinase Syk, which, in turn, activates multiple downstream mediators, such as ERK, PI-3K, and Akt (Zou et al., 2008). In addition, TREM2 may provide survival signals through activation of anti-apoptotic mediators such as β-catenin (Otero et al., 2009) and Mcl-1 (Peng et al., 2010). It is also possible that TREM2 is necessary to support increased microglial metabolism during activation.

Why is TREM2 activated during Aβ accumulation? Previous studies have indicated that TREM2 binds phospholipids, such as PS, and acts as a scavenger receptor for apoptotic cells that might be generated during neuronal damage (Hsieh et al., 2009; Takahashi et al., 2005, 2007). In our study, we demonstrate that TREM2 is a sensor for a broad array of acidic and zwitterionic lipids, which may or may not contain a phosphoric acid moiety. Membranes containing these lipids strongly interact with Aβ, facilitating the formation of fibrillar Aβ (Ahyayauch et al., 2012; Del Mar Martinez-Senac et al., 1999; Nagarathinam et al., 2013). Moreover, some TREM2 lipidic ligands accumulate on the cell surface of neurons and glial cells damaged by Aβ accumulation, such as PS (Eckert et al., 2005; McLaurin and Chakrabartty, 1996), or are released by damaged myelin, such as SM and sulfatides. In contrast, TREM2 did not directly bind Aβ. Consistent with its ability to bind anionic lipids, the TREM2 extracellular domain is rich in arginine residues that may form salt bridges with polyanions. Remarkably, we found that the R47H mutation associated with AD affected the binding of multiple lipid ligands, although to differing extents. Most likely, the R47H mutation is sufficient to considerably reduce the binding affinity of TREM2 extracellular domain for most anionic ligands. Structural studies will be essential to validate this model.

Our findings demonstrated that TREM2 functions as a microglial sensor that is alerted by damage-induced molecules that share a common lipidic backbone and an anionic group. In contrast with previous reports (Hsieh et al., 2009; Takahashi et al., 2005, 2007), we found that the engagement of TREM2 does not directly mediate phagocytosis of apoptotic cells. However, TREM2 signaling may indirectly support phagocytosis by promoting survival of activated microglia. It has been shown that individuals homozygous for rare mutations that impair expression of either TREM2 or DAP12 develop lethal forms of progressive, early-onset dementia such as Nasu-Hakola disease (NHD), Huntington's disease (Crotti et al., 2015), Parkinson's disease (Rayaprolu et al., 2013), and frontotemporal dementia (Guerreiro et al., 2013a, 2013c; Kleinberger et al., 2014; Paloneva et al., 2002). Although the pathology of these forms of dementia differs from that of AD and often involves demyelination, our study suggests that TREM2 may be required for microglia to sense glycolipids such as SM and sulfatides that are exposed on damaged myelin sheaths; thus, TREM2 binding to these glycolipids may trigger the microglial response to damaged myelin, which is necessary to clear myelin residues and produce trophic factors that induce repair and remyelination. While the R47H mutation associated with AD did not entirely abolish ligand binding, mutations associated with Nasu-Hakola disease result in a complete lack of TREM2 expression (Kleinberger et al., 2014), which may explain the distinct pathology and more dramatic clinical course of this disease.

Methods for the Examples

Mice:
Trem2$^{-/-}$ mice were generated as previously described. 5×FAD mice were purchased from the Jackson Laboratory (MMRRC) and crossed to Trem2$^{-/-}$ mice to generate Trem2$^{+/-}$5×FAD and Trem2$^{-/-}$5×FAD mice. All mice were bred and housed in the same animal facility. Trem2$^{-/-}$ Cx3cr1$^{+/GFP}$APPPS1-21 mice were generated in a similar manner, as previously described (Ulrich et al., 2014). All animal studies were approved by the Washington University Animal Studies Committee.

Preparation of Brain Samples:
For histological analysis 5×FAD mice, APPPS1-21 and transgene negative controls were anesthetized with ketamine and perfused with ice-cold PBS. Right-brain hemispheres were fixed in 4% PFA overnight and placed in 30% sucrose before freezing and cutting on a freezing sliding microtome. Serial 40-μm coronal sections of the brain were collected from the rostral anterior commissure to caudal hippocampus as landmarks. For biochemical and mRNA expression analysis, cortices and hippocampi of the left-brain hemispheres were carefully dissected out and flash frozen in liquid nitrogen.

Immunohistochemistry:
To analyze Aβ deposition, sections were stained with biotinylated anti-Aβ antibody, mHJ3.4. Stained brain sections were scanned with a NanoZoomer slide scanner (Hamamatsu Photonics). For quantitative analyses of mHJ3.4-biotin staining, scanned images were exported with NDP viewer software (Hamamatsu Photonics) and converted to 8-bit grayscale using ACDSee Pro-3 software (ACD Systems). Converted images were thresholded to highlight plaques and then analyzed using the "Analyze Particles" function in ImageJ (National Institutes of Health). Identified objects after thresholding were individually inspected to confirm the object as a plaque or not. Three brain sections per mouse, each separated by 300 μm, were used for quantification. These sections correspond roughly to sections at Bregma −1.7, −2.0, and −2.3 mm in the mouse brain atlas. The average of three sections was used to represent a plaque load for each mouse. For analysis of Aβ plaque in the cortex, the cortex immediately dorsal to the hippocampus was assessed. All analyses were performed in a blinded manner. To analyze neuronal loss, two matching brain sections at Bregma −1.7 and −2.0 mm in the mouse brain atlas per mouse were stained with cresyl violet and 3 images on matching areas of the cortex per section were taken. Numbers of layer-5 neurons were scored blinded using the Cell Counter function of ImageJ and expressed as average densities of nuclei per mm$^2$.

Microscopy and Quantification:

40 μm-floating sections were stained with Iba-1 (Waco chemicals) for microglia and X-34 for visualization of plaques as previously described (Styren et al., 2000). Images were collected using a customized Leica SP8 two-photon microscope (Leica) equipped with a 25×/0.95 NA water-dipping objective, and a Mai Tai HP DeepSee Laser (Spectra-Physics) tuned to 924 nm. Fluorescence emission was separated by high-efficiency custom dichroic mirrors (Semrock) and directly directed to supersensitive external detectors. 9 Z-stack images and 6 Z-stack images (447×447×20 μm, 1 μm thickness) were acquired in random regions of the cortices and hippocampi respectively. Images were then processed with Imaris (Bitplane) and exported to ImageJ for Iba-1 quantification. Z-stacks were merged to max intensity, channels split, and Iba-1 area was measured from each Z-stack images. For individual plaque analysis, 80 pixel circular gates were drawn around 10 randomly selected plaques per Z-stack image. Area was then measured in plaque and Iba-1 channels. A Click-iT TUNEL kit (Life Technologies) was used to assess apoptosis. Staining was quantified for each plaque in a Z-stack image as number of TUNEL$^+$Iba-1$^+$ cells within a 30 μm distance from the plaque. Lengths of the microglia processes were measured using the filament function of Imaris. Surface area of the microglia body was measured using the surface function of Immaris. More than 15 plaque-associated microglia were analyzed. All imaging quantification was performed in a blinded manner.

For computational analysis, X-, Y- and Z-coordinates of the microglia bodies and plaques of 14 representative Z-stack images of each genotype were manually labeled and recorded using the particle function of Imaris and imported into Matlab (Mathworks). Numbers of microglia within a 30 μm radius of a plaque were then determined using an automated script written in Matlab. Heatmaps were generated by fitting numbers of plaque-associated microglia into each pixel of a 447×447 matrix (total X and Y length of each image in μm with Z-dimension superimposed with maximal intensity compression). The modeled data were generated by randomly assigning coordinates of each microglia and plaque measured in each Z-stack image into a 447×447×10 volume while assuming no interaction between microglia and plaques (Monte Carlo simulation). To compare experimental data to random simulation, distribution of microglia frequencies per plaque in random simulation was first fitted into a Gaussian equation. Microglia frequencies in experimental conditions were then compared to the Gaussian curve and Z-score for each plaque was calculated (Equation 1). From the Z values, p values were then computed using Equation 2.

$$Z = \frac{X - \sigma}{\mu}$$ Equation 1

$$p = 1 \cdot \left( normcdf(Z) = \frac{1}{\sqrt{2\pi}} \int_{-\infty}^{Z} e^{-\frac{1}{2}x^2} \right)$$ Equation 2

For in vitro Aβ phagocytosis assay, sequential images were obtained with an Olympus FluoView FV1000 microscope every 60 s for a 60 min duration, and movies were assembled using Imaris and analyzed on ImageJ.

Gene Expression Analysis:

For frozen brain tissues, RNA was extracted using a RNeasy mini kit according to manufacture protocol (QIAGEN). Microglia were fluorescence-activated cell-sorted (FACS) directly into RLT-plus lysis buffer, and RNA extraction was performed using a RNeasy micro kit according to manufacture protocol (QIAGEN).

Microarray hybridization (Affymetrix MoGene 1.0 ST array) and data processing were performed at the Washington University Genome Center. Raw data were normalized using Robust Multi-Array (RMA) method and genes were pre-filtered for expression value ≥120 expression units, a cut-off above which genes have a 95% chance of expression demonstrated in Immgen data set, which uses the same array platform (Heng and Painter, 2008). Volcano plots and scatter plots of transcripts analyzed were produced using the Multiplot module of GenePattern (Reich et al., 2006). Heatmaps and hierarchical clustering (Kendall's tau distance) were generated from a selected gene-list using GENE-E. For PCA analysis, Euclidian distance matrices were determined using the 15% most variable transcripts, identified by one-way ANOVA test. The selected genes were log 2-transformed, filtered for probes with a mean expression value ≥120 and mean centered prior to visualization using the Population-Distances PCA application (Scott Davis).

ELISA:

Aβ levels were assessed using sandwich ELISAs as described (Kim et al., 2009). A mouse anti-human Aβ40 antibody (mHJ2) or mouse anti-human Aβ42 antibody (mHJ7.4) were used to capture and a biotinylated central domain antibody (mHJ5.1) was used to detect, followed by streptavidin poly-HRP-40 (Fitzgerald Industries). All ELISAs were developed using Super Slow ELISA TMB (Sigma) and absorbance read on a Bio-Tek Epoch plate reader at 650 nm. The standard curves for each assay used synthetic human Aβ$_{1-40}$ or Aβ$_{1-42}$ peptide (American Peptide).

Ex Vivo Microqlia Cultures:

Primary adult microglia culture was generated as previously described (Butov-sky et al., 2014). Briefly, purified adult microglia were cultured in the presence of 15% LCM media (Otero et al., 2009) and 10 ng/ml human TGF-β1 (Pepro-Tech) for 7 days before experiments.

For phagocytosis assay, Aβ$_{1-42}$-FAM (Anaspec) was aggregated as previously described (Huang et al., 2010) and diluted to a final concentration of 1 μg/ml. 1×10$^5$ WT and Trem2$^{-/-}$ microglia were dropped onto a chambered slide coated with Aβ$_{1-42}$-FAM aggregates. Uptake of Aβ aggregates was then captured in a period of 1 h. To examine Aβ digestion by microglia, soluble Aβ$_{1-42}$ (Anaspec) was added to microglia culture containing 1×10$^5$ WT or Trem2$^{-/-}$ microglia for 8 h. Aβ was then removed from culture media after 8 h incubation. Intracellular Aβ$_{1-42}$ concentration was determined 16 h later by ELISA. For phagocytosis assay of Apoptotic cells, 1×10⁵ WT or Trem2⁻/⁻ microglia were co-cultured with CSFE-labeled apoptotic cell at 1:5 ratio for up to 1 hr before FACS analysis. Trypsin was used to eliminate all surface-bound ACs. TNF-α production was measured using a mouse inflammation Cytometric Bead Array (CBA) kit (BD pharmingen). Transwell migration assay was performed as previously described (Huang et al., 2010). To assess microglia survival, 1×10⁵ WT or Trem2⁻/⁻ microglia were cultured with various concentrations of LCM for 3 days. Frequencies of viable cells were determined by propidium iodide (PI) staining on day 3. Morphology of cultured microglia was photographed using a Leica DM500 microscope.

Reporter Assay:

2B4 GFP-NFAT reporter T cells were stably transfected with murine or human TREM2 cDNAs. Cells were cultured with apoptotic thymocytes in round-bottom 96-well plates or plated onto high-absorbance flat-bottom plate coated with various lipids at indicated concentration. Reporter cells were assessed after overnight incubation. Reporter activity (%) is defined as % GFP cells subtracted from background (vehicle controls).

Statistics:

Data in figures are presented as mean±SEM. All statistical analysis was performed using Prism (GraphPad). Statistical analysis to compare the mean values for multiple groups was performed using a one-way or two-way ANOVA with correction for multiple comparisons. Comparison of two groups was performed using a two-tailed unpaired t-test (Mann-Whitney). Values were accepted as significant if $p<0.05$.

Example 7. hTREM2-Fc Soluble Molecule

The use of a chimeric soluble molecule consisting of hTREM2 extracellular region and the Fc fragment of IgG (hTREM2-Fc) soluble molecule in targeting microglia/macrophage is disclosed. TREM2 is a surface receptor expressed by myeloid cells, including microglia in the central nervous system (CNS) and transmits downstream signals through DAP12. Recent findings have shown that individuals with loss-of-function mutations of TREM2 are susceptible to neurodegenerative diseases such as Alzheimer's disease, frontotemporal dementia, Huntington's disease, Parkinson's disease, amyotrophic lateral sclerosis and Nasu-Hakola disease due to defective microglia functions. The use hTREM2-Fc is proposed to bypass lack of TREM2/DAP12 signaling by activating microglia through the high affinity Fc receptor (CD64). hTREM2-Fc consists a fusion molecule that contains: ectodomain of human TREM2 and Fc portion of the human immunoglobulins which binds to CD64 (FIG. 13). After being injected, hTREM2-Fc can reach the CNS and bind to CD64 on microglia through the Fc portion. Ligand recognition by TREM2 ectodomain leads to aggregation of the hTREM2-Fc/CD64 complex on microglia and the transmission of intracellular signals by CD64 through the associated Fc receptor gamma-chain (FcRγ), which triggers intracellular signals similar to those induced by DAP12.

Example 8. hTREM2 Reporters

The use of reporter cells expressing the arginine 47 to histidine mutation (R47H) of human TREM2 (hTREM2) in identifying potent agonists that correct the impaired function of mutated hTREM2 is disclosed. TREM2 is a surface receptor expressed by myeloid cells, including microglia in the central nervous system (CNS) and transmits intracellular signals through DAP12. Recent findings have shown that individuals with a R47H mutation of TREM2 have a substantial increase in susceptibility to Alzheimer's disease due to a loss-of-function of TREM2 signaling leading to defective microglia functions. We have generated a cellular-based reporter system (hTREM2 reporters) to identify ligands that trigger TREM2 signaling (FIG. 6 A-FIG. 6E, and FIG. 7A-FIG. 7H). We transfected hTREM2 in reporter cells that express GFP under the control of NFAT, such that when hTREM2 is engaged by a ligand, it will induce $Ca^{2+}$ mobilization that turns on GFP expression (FIG. 14). Using hTREM2 reporters with R47H mutation, we are able to demonstrate that this mutation affects TREM2 detection of many phospholipid ligands (FIG. 7A-FIG. 7H). However, we also identified TREM2 ligands that are recognized by TREM2 despite the R47H mutation suggesting that certain TREM2 ligands can be used to activate hTREM2 despite the R47H mutation.

REFERENCES FOR THE EXAMPLES

Ahyayauch, H., Raab, M., Busto, J. V., Andraka, N., Arrondo, J. L., Masserini, M. Tvaroska, I., and Goñi, F. M. (2012). Binding of 13-amyloid (1-42) peptide to negatively charged phospholipid membranes in the liquid-ordered state: modeling and experimental studies. Biophys. J. 103, 453-463.

Bouchon, A., Hernandez-Munain, C., Cella, M., and Colonna, M. (2001). A DAP12-mediated pathway regulates expression of CC chemokine receptor 7 and maturation of human dendritic cells. J. Exp. Med. 194, 1111-1122.

Butovsky, O., Jedrychowski, M. P., Moore, C. S., Cialic, R., Lanser, A. J., Ga-briely, G., Koeglsperger, T., Dake, B., Wu, P. M., Doykan, C. E., et al. (2014). Identification of a unique TGF-13-dependent molecular and functional signature in microglia. Nat. Neurosci. 17, 131-143.

Cannon, J. P., O'Driscoll, M., and Litman, G. W. (2012). Specific lipid recognition is a general feature of CD300 and TREM molecules. Immunogenetics 64, 39-47.

Chitu, V., and Stanley, E. R. (2006). Colony-stimulating factor-1 in immunity and inflammation. Curr. Opin. Immunol. 18, 39-48.

Crotti A, Glass C K. The choreography of neuroinflammation in Huntington's disease. Trends Immunol. 2015 June; 36(6):364-73.

D'Andrea, M. R., Cole, G. M., and Ard, M. D. (2004). The microglial phagocytic role with specific plaque types in the Alzheimer disease brain. Neurobiol. Aging 25, 675-683.

Daws, M. R., Lanier, L. L., Seaman, W. E., and Ryan, J. C. (2001). Cloning and characterization of a novel mouse myeloid DAP12-associated receptor family. Eur. J. Immunol. 31, 783-791.

Daws, M. R., Sullam, P. M., Niemi, E. C., Chen, T. T., Tchao, N. K., and Seaman, W. E. (2003). Pattern recognition by TREM-2: binding of anionic ligands. J. Immunol. 171, 594-599.

Del Mar Martínez-Senac, M., Villalaín, J., and Gómez-Fernandez, J. C. (1999). Structure of the Alzheimer beta-amyloid peptide (25-35) and its interaction with negatively charged phospholipid vesicles. Eur. J. Biochem. 265, 744-753.

Dickson, D. W. (1999). Microglia in Alzheimer's disease and transgenic models. How close the fit? Am. J. Pathol. 154, 1627-1631.

Eckert, G. P., Wood, W. G., and Müller, W. E. (2005). Membrane disordering effects of beta-amyloid peptides. Subcell. Biochem. 38, 319-337.

Eimer, W. A., and Vassar, R. (2013). Neuron loss in the 5xFAD mouse model of Alzheimer's disease correlates with intraneuronal Aβ42 accumulation and Caspase-3 activation. Mol. Neurodegener. 8, 2.

El Khoury, J., Toft, M., Hickman, S. E., Means, T. K., Terada, K., Geula, C., and Luster, A. D. (2007). Ccr2 deficiency impairs microglial accumulation and accelerates progression of Alzheimer-like disease. Nat. Med. 13, 432-438.

Ford, J. W., and McVicar, D. W. (2009). TREM and TREM-like receptors in inflammation and disease. Curr. Opin. Immunol. 21, 38-46.

Frautschy, S. A., Yang, F., Irrizarry, M., Hyman, B., Saido, T. C., Hsiao, K., and Cole, G. M. (1998). Microglial response to amyloid plaques in APPsw trans-genic mice. Am. J. Pathol. 152, 307-317.

Grathwohl, S. A., Kälin, R. E., Bolmont, T., Prokop, S., Winkelmann, G., Kaeser, S. A., Odenthal, J., Radde, R., Eldh, T., Gandy, S., et al. (2009). Formation and maintenance of Alzheimer's disease beta-amyloid plaques in the absence of microglia. Nat. Neurosci. 12, 1361-1363.

Guerreiro, R., Bilgic, B., Guven, G., Bras, J., Rohrer, J., Lohmann, E., Hana-gasi, H., Gurvit, H., and Emre, M. (2013a). Novel compound heterozygous mutation in TREM2 found in a Turkish frontotemporal dementia-like family. Neurobiol Aging 34, 2890, e2891-2895.

Guerreiro, R., Wojtas, A., Bras, J., Carrasquillo, M., Rogaeva, E., Majounie, E., Cruchaga, C., Sassi, C., Kauwe, J. S., Younkin, S., et al.; Alzheimer Genetic Analysis Group (2013b). TREM2 variants in Alzheimer's disease. N. Engl. J. Med. 368, 117-127.

Guerreiro, R. J., Lohmann, E., Bras, J. M., Gibbs, J. R., Rohrer, J. D., Gurunlian, M. Dursun, B., Bilgic, B., Hanagasi, H., Gurvit, H., et al. (2013c). Using exome sequencing to reveal mutations in TREM2 presenting as a frontotemporal dementia-like syndrome without bone involvement. JAMA Neurol. 70, 78-84.

Hamerman, J. A., Jarjoura, J. R., Humphrey, M. B., Nakamura, M. C., Seaman, W. E., and Lanier, L. L. (2006). Cutting edge: inhibition of TLR and FcR responses in macrophages by triggering receptor expressed on myeloid cells (TREM)-2 and DAP12. J. Immunol. 177, 2051-2055.

Hickman, S. E., Allison, E. K., and El Khoury, J. (2008). Microglial dysfunction and defective beta-amyloid clearance pathways in aging Alzheimer's disease mice. J. Neurosci. 28, 8354-8360.

Hsieh, C. L., Koike, M., Spusta, S. C., Niemi, E. C., Yenari, M., Nakamura, M. C., and Seaman, W. E. (2009). A role for TREM2 ligands in the phagocytosis of apoptotic neuronal cells by microglia. J. Neurochem. 109, 1144-1156.

Huang, Y., and Mucke, L. (2012). Alzheimer mechanisms and therapeutic strategies. Cell 148, 1204-1222.

Jiang, T., Tan, L., Zhu, X. C., Zhang, Q. Q., Cao, L., Tan, M. S., Gu, L. Z., Wang, H. F., Ding, Z. Z., Zhang, Y. D., et al. (2014). Upregulation of TREM2 Ameliorates Neuropathology and Rescues Spatial Cognitive Impairment in a Transgenic Mouse Model of Alzheimer's Disease. Neuropsychopharmacology.

Jonsson, T., Stefansson, H., Steinberg, S., Jonsdottir, I., Jonsson, P. V., Snae-dal, J., Bjornsson, S., Huttenlocher, J., Levey, A. I., Lah, J. J., et al. (2013). Variant of TREM2 associated with the risk of Alzheimer's disease. N. Engl. J. Med. 368, 107-116.

Kaku, M., Tsutsui, K., Motokawa, M., Kawata, T., Fujita, T., Kohno, S., Tohma, Y., Ohtani, J., Tenjoh, K., and Tanne, K. (2003). Amyloid beta protein deposition and neuron loss in osteopetrotic (op/op) mice. Brain Res. Brain Res. Pro-toc. 12, 104-108.

Kiialainen, A., Hovanes, K., Paloneva, J., Kopra, O., and Peltonen, L. (2005). Dap12 and Trem2, molecules involved in innate immunity and neurodegener-ation, are co-expressed in the CNS. Neurobiol. Dis. 18, 314-322.

Kim, J., Basak, J. M., and Holtzman, D. M. (2009). The role of apolipoprotein E in Alzheimer's disease. Neuron 63, 287-303.

Kleinberger, G., Yamanishi, Y., Suarez-Calvet, M., Czirr, E., Lohmann, E., Cuyvers, E., Struyfs, H., Pettkus, N., Wenninger-Weinzierl, A., Mazaheri, F., et al. (2014). TREM2 mutations implicated in neurodegeneration impair cell surface transport and phagocytosis. Sci Transl Med 6, 243ra286.

Maim, T. M., Koistinaho, M., Parepalo, M., Vatanen, T., Ooka, A., Karlsson, S., and Koistinaho, J. (2005). Bone-marrow-derived cells contribute to the recruitment of microglial cells in response to beta-amyloid deposition in APP/PS1 double transgenic Alzheimer mice. Neurobiol. Dis. 18, 134-142.

McGeer, P. L., Itagaki, S., Tago, H., and McGeer, E. G. (1987). Reactive micro-glia in patients with senile dementia of the Alzheimer type are positive for the histocompatibility glycoprotein HLA-DR. Neurosci. Lett. 79, 195-200.

McLaurin, J., and Chakrabartty, A. (1996). Membrane disruption by Alzheimer beta-amyloid peptides mediated through specific binding to either phospho-lipids or gangliosides. Implications for neurotoxicity. J. Biol. Chem. 271, 26482-26489.

Mildner, A., Schlevogt, B., Kierdorf, K., Bottcher, C., Erny, D., Kummer, M. P., Quinn, M., Bruck, W., Bechmann, I., Heneka, M. T., et al. (2011). Distinct and non-redundant roles of microglia and myeloid subsets in mouse models of Alz-heimer's disease. J. Neurosci. 31, 11159-11171.

Mitrasinovic, O. M., Vincent, V. A., Simsek, D., and Murphy, G. M., Jr. (2003). Macrophage colony stimulating factor promotes phagocytosis by murine microglia. Neurosci. Lett. 344, 185-188.

Nagarathinam, A., Hoflinger, P., Buhler, A., Schafer, C., McGovern, G., Jeffrey, M., Staufenbiel, M., Jucker, M., and Baumann, F. (2013). Membrane-anchored Abeta accelerates amyloid formation and exacerbates amyloid-associated toxicity in mice. J. Neurosci. 33, 19284-19294.

Oakley, H., Cole, S. L., Logan, S., Maus, E., Shao, P., Craft, J., Guillozet-Bon-gaarts, A., Ohno, M., Disterhoft, J., Van Eldik, L., et al. (2006). Intraneuronal beta-amyloid aggregates, neurodegeneration, and neuron loss in transgenic mice with five familial Alzheimer's disease mutations: potential factors in am-yloid plaque formation. J. Neurosci. 26, 10129-10140.

Otero, K., Turnbull, I. R., Poliani, P. L., Vermi, W., Cerutti, E., Aoshi, T., Tassi, I., Takai, T., Stanley, S. L., Miller, M., et al. (2009). Macrophage colony-stimulating factor induces the proliferation and survival of macrophages via a pathway involving DAP12 and beta-catenin. Nat. Immunol. 10, 734-743.

Otero, K., Shinohara, M., Zhao, H., Cella, M., Gilfillan, S., Colucci, A., Faccio, R., Ross, F. P., Teitelbaum, S. L., Takayanagi, H., and Colonna, M. (2012). TREM2 and 13-catenin regulate bone homeostasis by controlling the rate of os-teoclastogenesis. J. Immunol. 188, 2612-2621.

Paloneva, J., Manninen, T., Christman, G., Hovanes, K., Mandelin, J., Adolfs-son, R., Bianchin, M., Bird, T., Miranda, R., Salmaggi, A., et al. (2002). Mutations in two genes encoding different subunits of a receptor signaling complex result in an identical disease phenotype. Am. J. Hum. Genet. 71, 656-662.

Peng, Q., Malhotra, S., Torchia, J. A., Kerr, W. G., Coggeshall, K. M., and Humphrey, M. B. (2010). TREM2- and DAP12-dependent activation of PI3K requires DAβ10 and is inhibited by SHIP1. Sci. Signal. 3, ra38.

Perlmutter, L. S., Barron, E., and Chui, H. C. (1990). Morphologic association between microglia and senile plaque amyloid in Alzheimer's disease. Neuro-sci. Lett. 119, 32-36.

Ransohoff, R. M., and Cardona, A. E. (2010). The myeloid cells of the central nervous system parenchyma. Nature 468, 253-262.

Rayaprolu S, Mullen B, Baker M, Lynch T, Finger E, Seeley W W, Hatanpaa K J, Lomen-Hoerth C, Kertesz A, Bigio E H, Lippa C, Josephs K A, Knopman D S, White C L 3rd, Caselli R, Mackenzie I R, Miller B L, Boczarska-Jedynak M, Opala G, Krygowska-Wajs A, Barcikowska M, Younkin S G, Petersen R C, Ertekin-Taner N, Uitti R J, Meschia J F, Boylan K B, Boeve B F, Graff-Radford N R, Wszolek Z K, Dickson D W, Rademakers R, Ross O A. TREM2 in neurodegeneration: evidence for association of the p.R47H variant with frontotemporal dementia and Parkinson's disease. Mol Neurodegen. 2013 Jun. 21; 8:19.

Schmid, C. D., Sautkulis, L. N., Danielson, P. E., Cooper, J., Hasel, K. W., Hil-bush, B. S., Sutcliffe, J. G., and Carson, M. J. (2002). Heterogeneous expression of the triggering receptor expressed on myeloid cells-2 on adult murine micro-glia. J. Neurochem. 83, 1309-1320.

Sessa, G., Podini, P., Mariani, M., Meroni, A., Spreafico, R., Sinigaglia, F., Co-lonna, M., Panina, P., and Meldolesi, J. (2004). Distribution and signaling of TREM2/DAP12, the receptor system mutated in human polycystic lipomembraneous osteodysplasia with sclerosing leukoencephalopathy dementia. Eur. J. Neurosci. 20, 2617-2628.

Simard, A. R., Soulet, D., Gowing, G., Julien, J. P., and Rivest, S. (2006). Bone marrow-derived microglia play a critical role in restricting senile plaque formation in Alzheimer's disease. Neuron 49, 489-502.

Stalder, M., Phinney, A., Probst, A., Sommer, B., Staufenbiel, M., and Jucker, M. (1999). Association of microglia with amyloid plaques in brains of APP23 transgenic mice. Am. J. Pathol. 154, 1673-1684.

Stalder, A. K., Ermini, F., Bondolfi, L., Krenger, W., Burbach, G. J., Deller, T., Coomaraswamy, J., Staufenbiel, M., Landmann, R., and Jucker, M. (2005). Invasion of hematopoietic cells into the brain of amyloid precursor protein trans-genic mice. J. Neurosci. 25, 11125-11132.

Stanley, E. R., and Chitu, V. (2014). CSF-1 receptorsignalingin myeloid cells. Cold Spring Harb. Perspect. Biol. 6 dx.doi.org/10.1101/cshperspect.a021857.

Streit, W. J., and Xue, Q. S. (2009). Life and death of microglia. J. Neuroimmune Pharmacol. 4, 371-379.

Streit, W. J., Sammons, N. W., Kuhns, A. J., and Sparks, D. L. (2004). Dystrophic microglia in the aging human brain. Glia 45, 208-212.

Takahashi, K., Rochford, C. D., and Neumann, H. (2005). Clearance of apoptotic neurons without inflammation by microglial triggering receptor expressed on myeloid cells-2. J. Exp. Med. 201, 647-657.

Takahashi, K., Prinz, M., Stagi, M., Chechneva, O., and Neumann, H. (2007). TREM2-transduced myeloid precursors mediate nervous tissue debris clearance and facilitate recovery in an animal model of multiple sclerosis. PLoS Med. 4, e124.

Tanzi, R. E. (2013). A brief history of Alzheimer's disease gene discovery. J. Alzheimers Dis. 33 (Suppl 1), S5-S13.

Thrash, J. C., Torbett, B. E., and Carson, M. J. (2009). Developmental regulation of TREM2 and DAP12 expression in the murine CNS: implications for Nasu-Hakola disease. Neurochem. Res. 34, 38-45.

Turnbull, I. R., Gilfillan, S., Cella, M., Aoshi, T., Miller, M., Piccio, L., Hernandez, M., and Colonna, M. (2006). Cutting edge: TREM-2 attenuates macrophage activation. J. Immunol. 177, 3520-3524.

Ulrich, J. D., Finn, M. B., Wang, Y., Shen, A., Mahan, T. E., Jiang, H., Stewart, F. R., Piccio, L., Colonna, M., and Holtzman, D. M. (2014). Altered microglial response to A13 plaques in APPPS1-21 mice heterozygous for TREM2. Mol. Neurodegener. 9, 20.

Zou, W., Reeve, J. L., Liu, Y., Teitelbaum, S. L., and Ross, F. P. (2008). DAP12 couples c-Fms activation to the osteoclast cytoskeleton by recruitment of Syk. Mol. Cell 31, 422-431.

Heng, T. S., and Painter, M. W.; Immunological Genome Project Consortium (2008). The Immunological Genome Project: networks of gene expression in immune cells. Nat. Immunol. 9, 1091-1094.

Huang, W. C., Yen, F. C., Shie, F. S., Pan, C. M., Shiao, Y. J., Yang, C. N., Huang, F. L., Sung, Y. J., and Tsay, H. J. (2010). TGF-beta1 blockade of microglial chemo-taxis toward Abeta aggregates involves SMAD signaling and down-regulation of CCL5. J. Neuroinflammation 7, 28.

Reich, M., Liefeld, T., Gould, J., Lerner, J., Tamayo, P., and Mesirov, J. P. (2006). GenePattern 2.0. Nat. Genet. 38, 500-501.

Styren, S. D., Hamilton, R. L., Styren, G. C., and Klunk, W. E. (2000). X-34, a fluorescent derivative of Congo red: a novel histochemical stain for Alzheimer's disease pathology. J. Histochem. Cytochem. 48, 1223-1232

---

What is claimed is:

1. A method of activating a microglia cell in a subject with reduced or absent TREM2 intracellular signaling, the method comprising administering to the subject a composition comprising an isolated polypeptide comprising at least one TREM2 or fragment thereof and a targeting moiety, wherein the targeting moiety is an Fc fragment and wherein the Fc fragment binds to an Fc receptor on the microglia thereby activating the microglia by triggering intracellular signaling similar to those induced by DAP12.

2. The method of claim 1, wherein the TREM2 is the extracellular domain of TREM2.

3. The method of claim 1, wherein the extracellular domain of TREM2 comprises the amino acid sequence selected from the group consisting of SEQ ID NO:1 and SEQ ID NO:2.

4. A method for preventing a disease or condition associated with reduced or absent expression or activity of TREM2 in a microglial cell in a subject, the method comprising administering to the subject a composition comprising an isolated polypeptide comprising at least one TREM2 or fragment thereof and a targeting moiety, wherein the targeting moiety is an Fc fragment and wherein the Fc fragment binds to an Fc receptor on the microglia thereby triggering intracellular signaling similar to those induced by DAP12.

5. The method of claim 4, wherein the disease or condition is associated with loss-of-function of TREM2.

6. The method of claim 5, wherein the loss-of-function of TREM2 is due to an R47H mutation relative to SEQ ID NO:4.

7. The method of claim 4, wherein the disease or disorder is a neurodegenerative disease selected from the group consisting of Alzheimer's disease, frontotemporal dementia, Huntington's disease, Parkinson's disease, amyotrophic lateral sclerosis and Nasu-Hakola disease.

* * * * *